United States Patent [19]

Daniels

[11] 4,000,261
[45] Dec. 28, 1976

[54] 5-EPI-4,6-DI-O-(AMINOGLYCOSYL)-2-DEOXYSTREPTAMINES, METHODS FOR THEIR MANUFACTURE AND INTERMEDIATES USEFUL THEREIN, METHODS FOR THEIR USE AS ANTIBACTERIAL AGENTS AND COMPOSITIONS USEFUL THEREFOR

[75] Inventor: Peter J. L. Daniels, Cedar Grove, N.J.

[73] Assignee: Schering Corporation, Kenilworth, N.J.

[22] Filed: Sept. 8, 1975

[21] Appl. No.: 611,289

Related U.S. Application Data

[63] Continuation-in-part of Ser. No. 528,593, Nov. 29, 1974, abandoned.

[52] U.S. Cl. .............................. 424/180; 536/17; 536/10
[51] Int. Cl.$^2$ ................ A61K 31/71; C07H 15/22
[58] Field of Search .... 260/210 AB, 210 R, 210 K; 424/180

[56] References Cited
UNITED STATES PATENTS

| | | | |
|---|---|---|---|
| 3,828,021 | 8/1974 | Beattie et al. | 260/210 AB |
| 3,920,628 | 11/1975 | Daniels | 260/210 AB |

*Primary Examiner*—Johnnie R. Brown
*Attorney, Agent, or Firm*—Mary S. King

[57] ABSTRACT

5-Epi-4,6-di-O-(aminoglycosyl)-2-deoxystreptamines and 1-N-alkyl-5-epi-4,6-di-O-(aminoglycosyl)-2-deoxystreptamines, valuable as antibacterial agents, are prepared from the corresponding 5-O-hydrocarbonsulfonyl (or substituted hydrocarbonsulfonyl)-4,6-di-O-(aminoglycosyl)-2-deoxystreptamine wherein amino and hydroxyl functions are protected by groups susceptible to reductive cleavage or to basic or mild acid hydrolysis, by the reaction thereof with dimethylformamide at elevated temperatures, followed by removal of the protecting groups. Alternatively, 5-epi-4,6-di-O-(aminoglycosyl)-2-deoxystreptamines and their 1-N-alkyl derivatives are prepared by oxidation of the corresponding 4,6-di-O-(aminoglycosyl)-2-deoxystreptamine wherein the amino and hydroxyl functions other than the 5-hydroxyl function are protected by groups susceptible to reductive cleavage or to basic or mild acid hydrolysis, with ruthenium tetroxide, chromic acid in acetone or chromium trioxide-pyridine complex in methylene chloride, thence reaction of the thereby produced 5-dehydro-4,6-di-O-(aminoglycosyl)-2-deoxystreptamine or 1-N-alkyl derivative thereof (novel intermediates) with an alkali metal borohydride followed by removal of the amino and hydroxyl protecting groups.

In addition to the foregoing, methods are described whereby the 1-N-alkyl-5-epi-4,6-di-O-(aminoglycosyl)-2-deoxystreptamines are prepared from the corresponding 1-N-unsubstituted-5-epi-4,6-di-O-(aminoglycosyl)-2-deoxystreptamines.

Pharmaceutical compositions comprising 5-epi-4,6-di-O-(aminoglycosyl)-2-deoxystreptamines or 1-N-alkyl-5-epi-4,6-di-O-(aminoglycosyl)-2-deoxystreptamines elicit an antibacterial response in a warm blooded animal having a susceptible bacterial infection.

33 Claims, No Drawings

ID# 5-EPI-4,6-DI-O-(AMINOGLYCOSYL)-2-DEOXYS-
TREPTAMINES, METHODS FOR THEIR
MANUFACTURE AND INTERMEDIATES USEFUL
THEREIN, METHODS FOR THEIR USE AS
ANTIBACTERIAL AGENTS AND COMPOSITIONS
USEFUL THEREFOR

CROSS REFERENCE TO RELATED APLICATIONS

This application is a continuation-in-part of copending application Ser. No. 528,593, filed Nov. 29, 1974, now abandoned.

FIELD OF INVENTION

This invention relates to novel compositions-of-matter, to methods for their manufacture and intermediates useful therein, to pharmaceutical formulations and to methods for their use as antibacterial agents.

More specifically, this invention relates to novel 5-epi-4,6-di-O-(aminoglycosyl)-2-deoxystreptamines and the 1-N-alkyl derivatives thereof having antibacterial activity, to methods for their manufacture, to pharmaceutical compositions thereof and to methods for their use in treating bacterial infections.

In particular, this invention relates to 5-epi-derivatives of 4,6-di-O-(aminoglycosyl)-2-deoxystreptamine antibacterial agents including the gentamicins, verdamicin, tobramycin, the kanamycins, Antibiotics G-418, 66-40B, 66-40D, JI-20A, JI-20B and G-52 and the 1-N-alkyl derivatives thereof.

This invention also relates to intermediates useful in the manufacture of the antibacterial agents of the invention; in particular to the 5-dehydro-4,6-di-O-(aminoglycosyl)-2-deoxystreptamines and the 1-N-alkyl derivatives thereof having hydroxyl functions and amino functions protected by groups susceptible to reductive cleavage or to basic or mild acid hydrolysis.

This invention also relates to the processes for preparing the foregoing 5-epi-4,6-di-O-(aminoglycosyl)-2-deoxystreptamines and their 1-N-alkyl derivatives, to pharmaceutical compositions comprising said 5-eip-4,6-di-O-(aminoglycosyl)-2-deoxystreptamines and their 1-N-alkyl derivatives, and to the method of using said pharmaceutical compositions to elicit an antibacterial response in a warm blooded animal having a susceptible bacterial infection.

PRIOR ART

Known in the art are broad spectrum antibacterial agents which may be classified chemically as 4,6-di-O-(aminoglycosyl)-1,3-diaminocyclitols. Valuable antibacterial agents of this group are those wherein the aminocyclitol is 2-deoxystreptamine. Particularly valuable antibacterials of the 4,6-di-O-(aminoglycosyl)-2-deoxystreptamines are those wherein the aminoglycosyl group at the 6-position is a garosaminyl radical. Within the class of 4-O-aminoglycosyl-6-O-garosaminyl-2-deoxystreptamines are antibiotics such as gentamicins B, $B_1$, $C_1$, $C_{1a}$, $C_2$, $C_{2a}$, $C_{2b}$ and $X_2$; verdamicin, sisomicin, Antibiotic G-418, Antibiotic G-52, Antibiotic JI-20A and Antibiotic JI-20B.

Also known in the art are 1-N-alkyl derivatives of the aforementioned 4,6-di-O-(aminoglycosyl)-1,3-diaminocyclitols which, in general, exhibit broad spectrum antibacterial activity and possess enhanced activity against compounds resistant to the 1-N-unsubstituted antibacterial agent.

By my invention I have discovered methods whereby the hydroxyl function at the 5-position of the 2-deoxystreptamine or derivative thereof in a 4,6-di-O-(aminoglycosyl)-2-deoxystreptamine is converted to the 5-epimer. I have discovered also that 5-epi-4,6-di-O-(aminoglycosyl)-2-deoxystreptamines, their 1-N-alkyl derivatives and acid addition salts thereof are valuable broad spectrum antibacterial agents possessing improved antibacterial activities compared to the parent antibiotics. Preferred compounds of my invention include 5-epi-4,6-di-O-(aminoglycosyl)-2-deoxystreptamins and 1-N-alkyl derivatives thereof wherein the 6-O-aminoglycosyl group is 6-O-garosaminyl, which derivatives exhibit an improved antibacterial spectrum over that of the parent compound.

GENERAL DESCRIPTION OF THE INVENTION

COMPOSITION-OF-MATTER ASPECT

Included among the antibacterially active compositions-of-matter of this invention are 5-epi-4,6-di-O-(aminoglycosyl)-2-deoxystreptamines selected from the group consisting of 5-epigentamicin A, 5-epigentamicin B, 5-epigentamicin $B_1$, 5-epigentamicin $C_1$, 5-epigentamicin $C_{1a}$, 5-epigentamicin $C_2$, 5-epigentamicin $C_{2a}$, 5-epigentamicin $C_{2b}$, 5-epigentamicin $X_2$, 5-epiverdamicin, 5-epitobramycin, 5-epitobramycin, 5-epi-Antibiotic G-418, 5-epi-Antibiotic 66-B, 5-epi-Antibiotic 66-40D, 66-40D, 5-epi-Antibiotic 66-40JI-20A, 5-epi-Antibiotic JI-20B, 5-epi-Antibiotic G-52, 5-epi-3',4'-dideoxykanamycin B, 5-epikanamycin A and 5-epi kanamycin B;

the 1-N-K derivatives of the foregoing,
wherein K is an alkyl substituent selected from the group consisting of alkyl, alkyl cycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom;

and the pharmaceutically acceptable acid addition salts thereof.

Particularly useful antibacterial agents of my invention include 5-epi-4,6-di-O-(aminoglycosyl)-2-deoxystreptamines wherein the aminoglycoside radical at the 6-position is garosaminyl. Typical 5-epi-4-O-aminoglycosyl- 6-O-garosaminyl-2-deoxystreptamines of this invention are 5-epigentamicin B, 5-epigentamicin $B_1$, 5-epigentamicin $C_1$, 5-epigentamicin $C_{1a}$, 5-epigentamicin $C_2$5-epigentamicin-$C_{2b}$, 5-epigentamicin $C_{2b}$, 5-epigentamicin $X_2$, 5-epiverdamicin, 5-epi-Antibiotic G-418, 5-epi-Antibiotic JI-20A, 5-epi-Antibiotic JI-20B, 5-epi-Antibiotic G-52, and the 1-N-alkyl derivatives thereof, which compounds are defined by the following structural formula I:

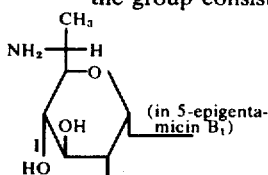
(in 5-epigenta-micin B)

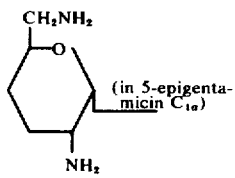
(in 5-epigenta-micin B₁)

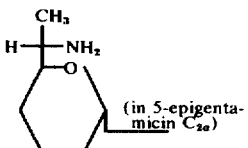
(in 5-epigenta-micin C₁)

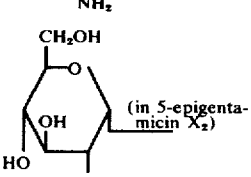
(in 5-epigenta-micin C₁ₐ)

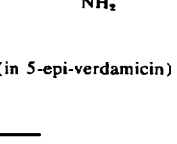
(in 5-epigenta-micin C₂)

(in 5-epigenta-micin C₂ₐ)

(in 5-epigenta-micin C₂ᵦ)

(in 5-epigenta-micin X₂)

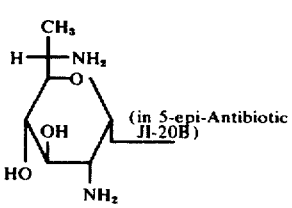
(in 5-epi-verdamicin)

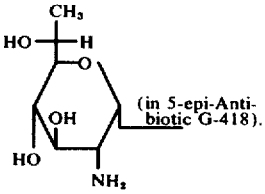
(in 5-epi-Antibiotic JI-20A)

(in 5-epi-Antibiotic JI-20B)

(in 5-epi-Antibiotic G-52), and (in 5-epi-Antibiotic G-418).

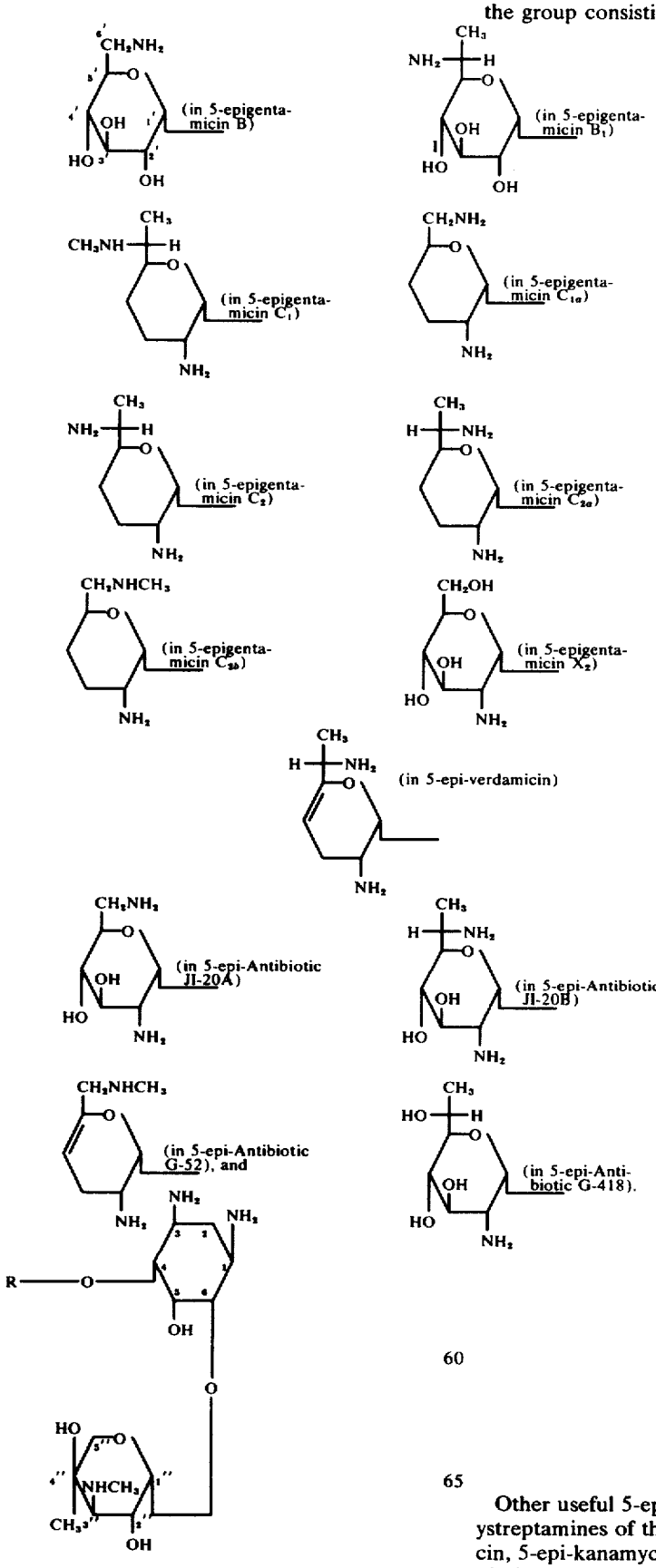

and the 1-N-K derivatives thereof, K being as hereinabove defined;

wherein R is an aminoglycosyl function selected from the group consisting of:

Other useful 5-epi-4,6-di-O-(aminoglycosyl)-2-deoxystreptamines of this invention include 5-epi-tobramycin, 5-epi-kanamycin A, 5-epi-kanamycin B and 5-epi-3',4'-dideoxykanamycin B of following formula II:

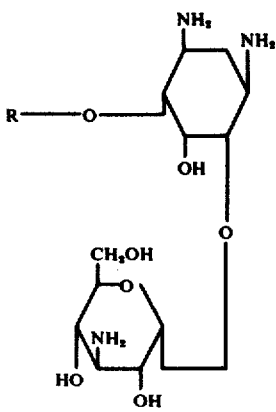

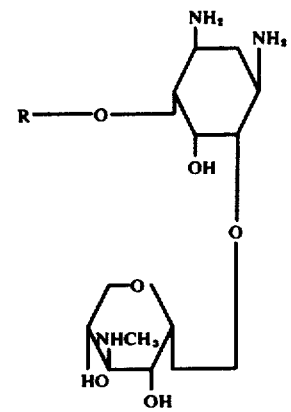

and the 1-N-K derivatives thereof, K being as hereinabove defined;
wherein R is an aminoglycosyl function selected from the group consisting of:

and the 1-N-K derivatives thereof, K being as hereinabove defined;
wherein R is an aminoglycosyl function selected from the group consisting of

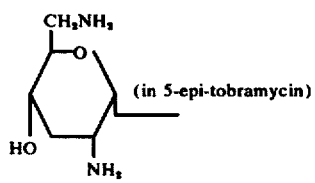

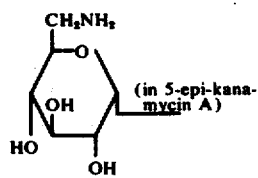

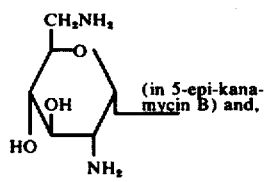

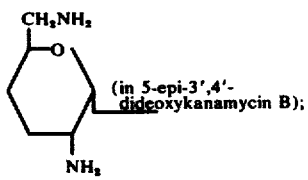

5-Epi-Antibiotic 66-40D of following formula III:

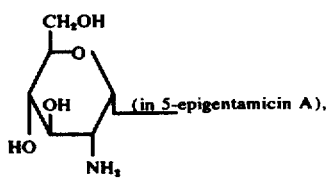

and

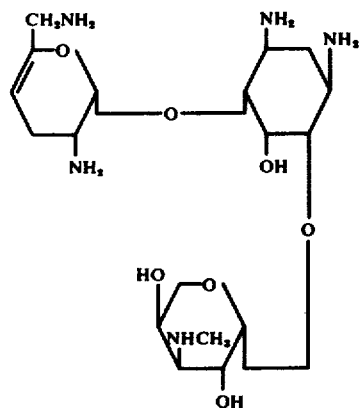

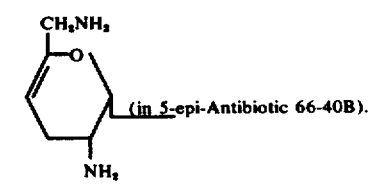

and the 1-N-K derivatives thereof, K being as hereinabove defined;
and 5-epigentamicin A, 5-epi-Antibiotic 66-40B of the following formula IV:

The 5-epi-4,6-di-O-(aminoglycosyl)-2-deoxystreptamines of this invention as defined by formulae I, II, III and IV and their 1-N-alkyl derivatives are characterized by being white amorphous powders.

Also included within the composition-of-matter aspect of this invention are pharmaceutically acceptable acid addition salts of the 5-epi-4,6-di-O-(aminoglycosyl)-2-deoxystreptamines such as defined by formulae I, II, III and IV and their 1-N-alkyl derivatives, which salts are made according to known procedures such as by neutralizing the free base with the appropriate acid, usually to about pH 5. Suitable acids for this purpose include acids such as hydrochloric, sulfuric, phosphoric, hydrobromic and the like. The physical embodiments of the acid addition salts of the 5-epi-4,6-di-O-(aminoglycosyl)-2-deoxystreptamines are characterized by being white solids which are soluble in water and insoluble in most polar and non-polar organic solvents.

The 5-epi-4,6-di-O-(aminoglycosyl)-2-deoxystreptamines, such as defined by formulae, I, II, III and IV and their 1-N-alkyl derivatives, particularly those wherein the 6-O-aminoglycosyl is 6-O-garosaminyl, and their non-toxic, pharmaceutically acceptable acid addition salts, in general, exhibit broad spectrum antibacterial activity and possess an improved antibacterial spectrum compared to that of the parent antibiotics. This improved spectrum consists of enhanced potency of the claimed compounds against organisms resistant to the parent compound. Thus, for example, compounds of this invention, e.g. 5-epi-4-O-aminoglycosyl-6-O-garosaminyl-2-deoxystreptamines, are more active against organisms which inactivate the parent antibiotics by acetylation of the 3-amino group and/or by adenylylation of the 2"-hydroxyl group. Of these, some also exhibit antiprotozoal, anti-amoebic and anthelmintic properties. The 1-N-alkyl derivatives of this invention, particularly the 1-N-ethyl-5-epi-4-O-aminoglycosyl-6-O-garosaminyl-2-deoxystreptamines also exhibit improved potency against Pseudomonas as compared to their 1-N-unsubstituted precursors having the normal configuration at C-5.

Particularly valuable compounds of this invention are 5-epi-4-O-aminoglycosyl-6-O-garosaminyl-2-deoxystreptamines of formula I, particularly the 5-epi- derivatives of gentamicin $C_1$, gentamicin $C_{1a}$, gentamicin $C_2$, gentamicin $C_{2a}$, gentamicin $C_{2b}$, verdamacin, Antibiotic G-52, as well as 5-epi-Antibiotic 66-40D of formula III, which derivatives are broad spectrum antibacterial agents, being active against gram positive bacteria (e.g. *Staphylococcus aureus*) and gram negative bacteria (e.g. *Escherichia coli* and *Pseudomonas aeruginosa*) as determined by standard dilution tests, including bacteria resistant to the parent compounds. Additionally, the 1-N-ethyl derivatives of the foregoing 5-epiaminoglycosides possess improved potency against Pseudomonas.

Other composition-of-matter aspects of this invention include O- and N-protected-5-dehydro derivatives of the 4,6-di-O-(aminoglycosyl)-2-deoxystreptamines of formulae I, II,III an IV and the 1-N-alkyl derivatives thereof wherein all hydroxyl functions and amino functions are protected by groups susceptible to reductive cleavage (such as by treatment with hydrogen in the presence of a catalyst or by treatment with an alkali metal in liquid ammonia) or to basic or mild acid hydrolysis (such as with aqueous sodium hydroxide or aqueous acetic acid0), which compounds are useful as intermediates in preparing the antibacterially active 5-epi-aminoglycosides of formulae I, II, III and IV and the 1-N-alkyl derivatives thereof.

Useful amino protecting groups (designated by "Y" in Formulae V to XII shown hereinbelow) for the intermediates of this invention include lower alkoxycarbonyls (preferably having up to 8 carbon atoms, e.g. methoxycarbonyl, ethoxycarbonyl, n-propyloxycarbonyl, iso-propyloxycarbonyl, n-butyloxycarbonyl, tert.-butoxycarbonyl, octyloxycarbonyl and the like), substituted benzyloxycarbonyl (including o, m and p-methoxybenzyloxycarbonyl, mesityloxycarbonyl and the like) and, preferably, benzyloxycarbonyl. Lower alkanoyls preferably having up to 8 carbon atoms (e.g. acetyl, propionyl, valeryl, caprylyl) are also useful amino protecting groups (Y), particularly for intermediates derived from antibacterials which cannot form a 3",4"-N,O-carbonyl derivative (e.g. intermediates not having a 6-O-garosaminyl substituent such as gentamicin A and the kanamycins).

The foregoing amino protecting groups are removable by treatment with base (e.g. with sodium hydroxide) or, in the case of benzyloxycarbonyl, by reductive cleavage methods known in the art. Benzyloxycarbonyl is a preferred amino protecting group for the intermediates of this invention since, in aminoglycosides having a cis-hydroxyl function adjacent to an amino function, such as at positions 3" and 4" in the 6-O-garosaminyl radical of the aminoglycosides of formula I, the N-benzyloxycarbonyl derivative (e.g. the 3"-N-benzyloxycarbonyl derivatives of compounds of formula I) when subjected to basic conditions (such as with sodium hydride in dimethylformamide) forms an oxazolidinone with the adjacent hydroxyl function (e.g. a 3",4"-N,O-carbonyl derivative of compounds of formula I) with concomitant formation of benzyl alcohol. Similarly, N-alkoxycarbonyl derivatives will form oxazolidinones with an adjacent cis-hydroxyl function. In the case where a starting compound has a 1-N-alkyl (i.e. a 1-N-K-) substituent which has a hydroxyl group alpha or beta to an amino-protecting group, Y, which is a benzyloxycarbonyl or alkoxycarbonyl, the hydroxy group together with said protecting group Y will form an oxazolidinone or a tetrahydro-1,3-oxazin-2-one, respectively.

Hydroxyl functions in the intermediates of this invention are conveniently protected by O-acyl radicals of hydrocarboncarboxylic acids preferably having up to 8 carbon atoms (said radicals being designated as "Z" in Formulae V to XII hereinbelow) or by O-hydrocarbonylidene radicals of ketones and aldehydes preferably having up to 8 carbon atoms to form ketals and acetals, respectively, including cyclic ketals (said hydrocarbonylidene radicals being designated as "W" in Formulae V to XII hereinbelow).

In general, neighboring hydroxyl groups in the aminoglycoside precursors of the intermediates of this invention are conveniently protected by cyclic ketals and acetals. By "neighboring hydroxyl groups" are contemplated vicinal and non-vicinal hydroxyl groups which are situated so that together they form a cyclic ketal cyclic acetal function with ketones and aldehydes or their derivatives, respectively. Exemplary of such "neighboring hydroxyl groups" are the 2',3'-hydroxyl groups in gentamicins B and $B_1$ and in kanamycin A (which form 2',3'-O-hydrocarbonylidene derivatives), the 4',6'-hydroxyl groups in gentamicins A and $X_2$ and in Antibiotic G-418 (which form 4',6'-O-hydrocarbonylidene derivatives, the 3',4'-hydroxyl groups in Antibiotics JI-20A and JI-20B and in kanamycin A (which form 3',4'-O-hydrocarbonylidene derivatives) and the 4",6"-hydroxyl groups in tobramycin, kanamycins A and B, and 3',4'-dideoxykanamycin B (which form 4",6"-O-hydrocarbonylidene derivatives).

The cyclic ketal and acetal derivatives of said neighboring hydroxyl groups of this invention include O-alkylidene (e.g. O-iso-propylidene), O-cycloalkylidene (e.g. O-cyclohexylidene), and O-arylalkylidene (e.g.

O-benzylidene) derivatives, all of which are removable upon treatment with dilute aqueous acid (e.g. by 50 to 80% acetic acid). The nature of the hydrocarbon "ylidene" radicals of the cyclic ketals and acetals is immaterial since these radicals act only as "blocking groups", do not enter into the process of the invention, and are subsequently removed so that the free hydroxyls are regenerated in their original form.

In the 5-dehydro-per-N-protected-per-O-protected intermediates of this invention, isolated hydroxyl groups other than the 5-hydroxyl group, such as the 2''-hydroxy present in all the aminoglycoside precursors of this invention, the 4'-hydroxy in tobramycin, and the 4''-hydroxy in Antibiotic 66-40B and in gentamicin A as well as hydroxyl groups which are not protected by cyclic ketal or acetal functions (e.g. the 3'-hydroxy in gentamicin A and the 2' and 4'-hydroxyl in kanamycin A) are conveniently protected by hydrocarboncarbonyl radicals (designated as "Z" in formulae V to XII hereinbelow), said hydrocarbon preferably having up to 8 carbon atoms. Useful hydrocarbonylcarbonyl radicals are acyl radicals derived from lower alkanoic acids having up to 8 carbon atoms including acetyl, propionyl, n-butyryl, valeryl, and caprylyl, as well as acyl radicals derived from aralkanoic acids such as phenylacetyl and from arylcarboxylic acids such as o, m and p-toluoyl, mesityloyl, and preferably benzoyl. These groups are removable by treatment with base.

Included among the 5-dehydro-per-N-protected-per-O-protected intermediates of this invention are 1,3,2',6'-tetra-N-Y-5-dehydro-2''-O-Z-3'',4''-N-O-carbonyl-Antibiotic 66-40D of following formula V:

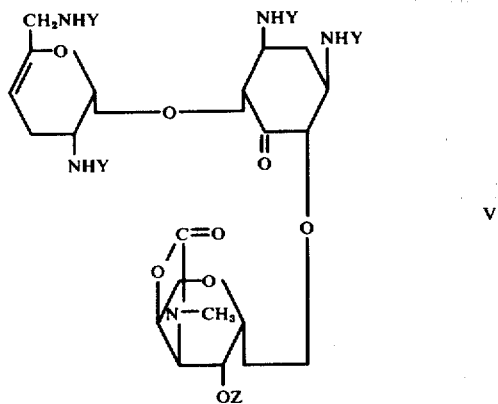

and 1,3,2',6'-tetra-N-Y-5-dehydro-2''O-Z-3'',4''N,O-carbonyl-4,6-di-O-(aminoglycosyl)-2-deoxystreptamines of following formula VI:

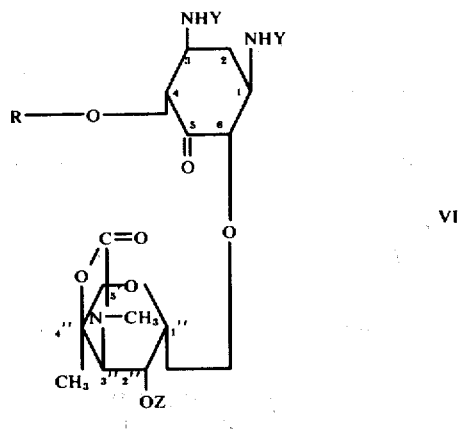

and the 1-N-K'' derivatives thereof wherein K'' is as hereinabove defined for K but wherein any amino function is substituted by a group Y, and any hydroxyl function is converted to an ester OZ or, when said hydroxyl group is alpha or beta to an amino-protecting group Y, which is benzyloxycarbonyl or alkoxycarbonyl, the hydroxyl group together with said protecting group Y is converted to an oxazolidinone or a tetrahydro-1,3-oxazin-2-one, respectively, Y and Z being as defined hereinbelow:

wherein Y is a member selected from the group consisting of benzyloxycarbonyl, substituted benzyloxycarbonyl and alkoxycarbonyl, and Z is a hydrocarboncarbonyl, said hydrocarbon having up to 8 carbon atoms; and R is an aminoglycosyl function selected from the group consisting of:

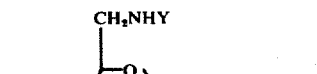

(in 5-dehydro-gentamicin C₁)

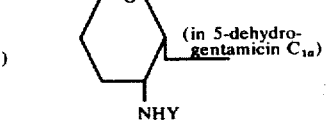

(in 5-dehydro-gentamicin C₁ₐ)

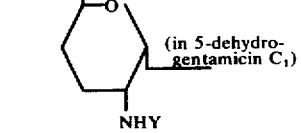

(in 5-dehydro-gentamicin C₂)

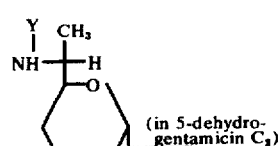

(in 5-dehydro-gentamicin C₂ₐ)

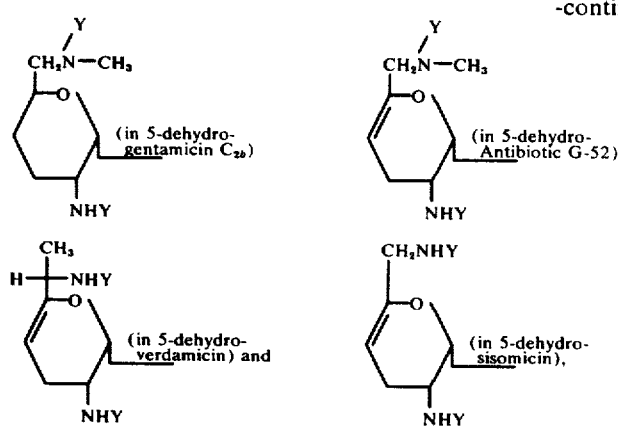

wherein Y is as hereinabove defined.

Other 5-dehydro-per-N-protected-per-O-protected intermediates of this invention include 1,3,2',6',3''-penta-N-Y'-5-dehydro-4',2''-di-O-Z-4'',6''-O-W-tobramycin, 1,3,6',3''-tetra-N-Y'-5-dehydro-2',2''-O-Z-3',4';4'',6''-di-O-W-kanamycin A, 1,3,6',3''-tetra-N-Y'-5-dehydro-4',2''-di-O-Z-2',3';4'',6''di-O-W-kanamycin A, 1,3,2',6',3''-penta-N-Y'-5-dehydro-3',4';4'',6''-di-O-W-2''-O-Z-kanamycin B, and 1,3,2',6',-3''-penta-N-Y'-5-dehydro-2''-O-Z-4'',6''-O-W-3',4'- and the 1-N-K''-derivatives thereof wherein K'' is as hereinabove defined; and wherein W is a hydrocarbonylidene having up to 8 carbon atoms selected from the group consisting of alkylidene, cycloalkylidene and arylalkylidene;

Y' is lower alkanoyl, benzyloxycarbonyl, substituted benzyloxycarbonyl or alkoxycarbonyl;

Z is as defined for formulae V and VI, and R is a member selected from the group consisting of:

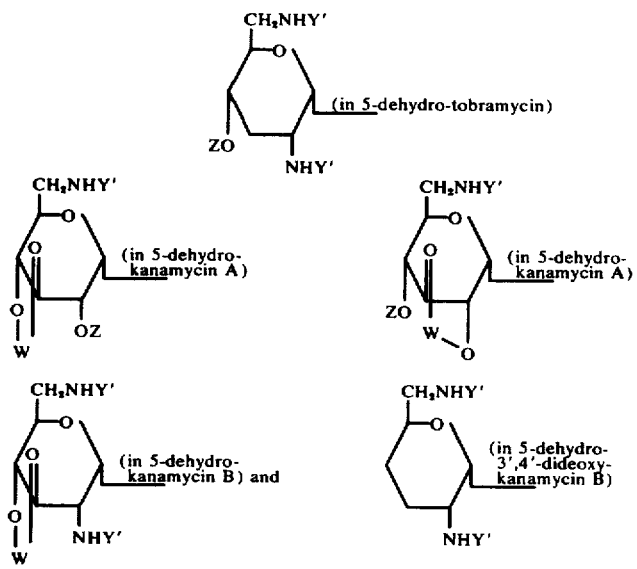

dideoxykanamycin B of formula VII:

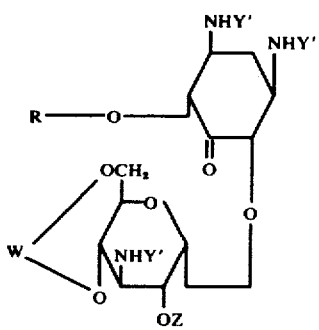

VII wherein W, Y' and Z are as hereinabove defined;
1,3-di-N-Y-5-dehydro-2',3'-O-W-6',4';3'',4''-di-N,O-carbonyl-2''-O-Z-derivatives of gentamicins B and B₁ of following formula VIII:

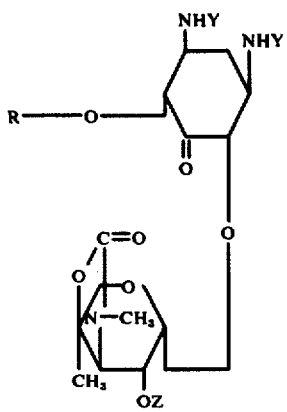

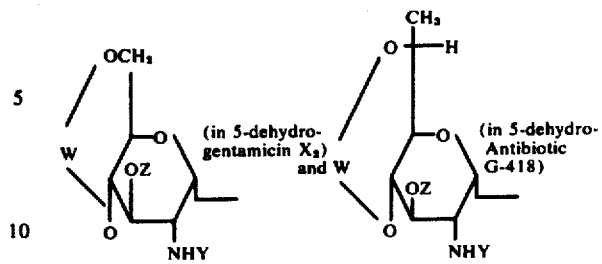

W, Y and Z being as hereinabove defined;
1,3,2',6',3''-penta-N-Y'-5-dehydro-2''',4''-di-O-Z-Antibiotic 66-40B of following formula X:

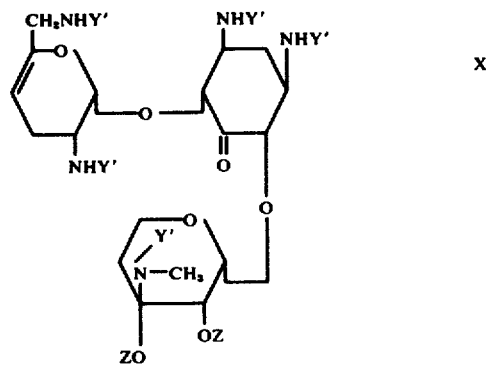

and the 1-N-K'' derivatives thereof wherein K is as hereinabove defined; and
wherein Y and Z are as hereinabove defined, and R is an aminoglycosyl function selected from the group consisting of:

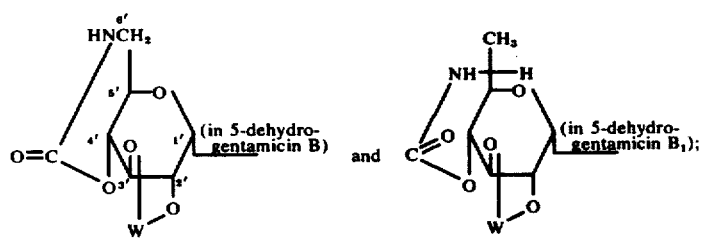

W being as above defined;
1,3,2'-tri-N-Y-5-dehydro-3',2''di-O-Z-4',6'O-W-3'',4''-N,O-carbonyl derivatives of gentamicin $X_2$ and Antibiotic G-418 of following formula IX:

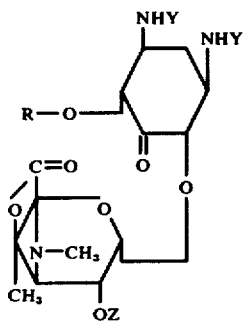

and the 1-N-K'' derivatives thereof wherein K is as hereinabove defined; and
wherein Y and Z are as hereinabove defined and R is an aminoglycosyl function selected from the group consisting of:

and the 1-N-K'' derivatives thereof wherein K is as hereinabove defined; and wherein
Y' and Z are as hereinabove defined;
1,3,2',3'''-tetra-N-Y'-5-dehydro-3',2''',4''-tri-O-Z-4',6'-O-W-gentamicin A of following formula XI:

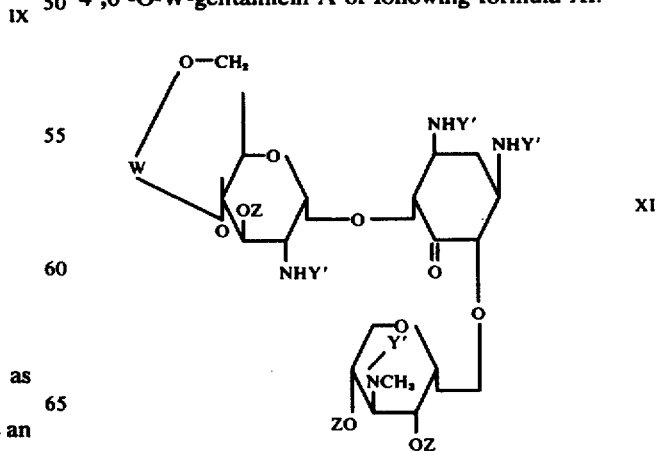

and the 1-N-K'' derivatives thereof wherein K is as hereinabove defined; and wherein W, Y' and Z are as hereinabove defined;

and 1,3,2',6'-tetra-N-Y-5-dehydro-3',4'-O-W-2''-O-Z-3'',4''-N,O-carbonyl derivatives of Antibiotics JI-20A and JI-20B of following formula XII:

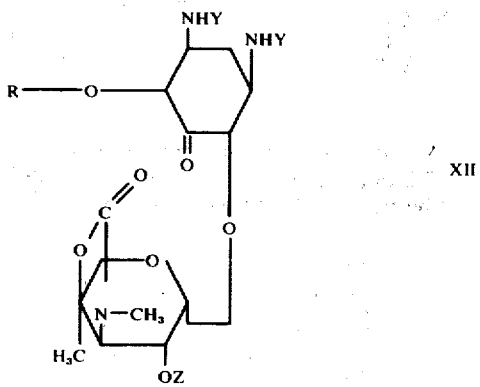

and the 1-N-K'' derivatives thereof wherein K is as hereinabove defined; and wherein Y and Z are as hereinabove defined and R is an aminoglycosyl function selected from the group consisting of:

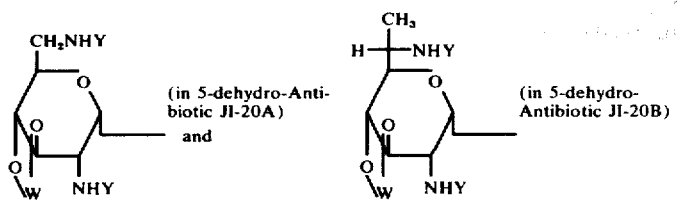

The 5-dehydro-per-N-protected-per-O-protected-4,6-di-O-(aminoglycosyl)-2-deoxystreptamine intermediates of this invention as defined by formulae V - XII and their 1-N-alkyl derivatives are characterized by being white solids. Their preparation is described in the general description of the process aspect of this invention set forth hereinbelow.

GENERAL DESCRIPTION OF THE PROCESS ASPECTS OF THE INVENTION

In one process of this invention, the antibacterially active 5-epi-4,6-di-O-(aminoglycosyl)-2-deoxystreptamines of this invention, e.g. as defined by formulae I, II, III and IV, and the 1-N-alkyl derivatives thereof are prepared by the reaction of the corresponding 5-O-hydrocarbonsulfonyl (or substituted hydrocarbonsulfonyl)-per-N-protected-per-O-protected-4,6-di-O-(aminoglycosyl)-2-deoxystreptamine (e.g. compounds similar to those defined by formulae V - XII and their 1-N-alkyl derivatives but having a hydrocarbonsulfonyloxy function at C-5 instead of an oxo function) with dimethylformamide, preferably in the presence of a tetraalkylammonium alkanoate, usually tetra-n-butylammonium acetate, at elevated temperatures, usually in the range of from about 80° C to about 155° C (preferably from about 100° C to reflux temperature (i.e. about 153° C)); thence removal of the protecting groups by reaction of the resulting N-protected-O-protected intermediate with aqueous base or, when protecting groups susceptible to reductive cleavage are present, by reaction with a reducing agent selected from the group consisting of hydrogen in the presence of a catalyst or with an alkali metal in liquid ammonia, followed by treatment with aqueous base; thence, when acetals or ketals are present, by treatment of the thereby formed 5-epi-4,6-di-O-(aminoglycosyl)-2-deoxystreptamine derivative with aqueous acid.

The treatment of a 5-O-hydrocarbonsulfonyl intermediate with dimethylformamide alone is often carried out at reflux temperature (i.e. about 153° C) since the rate of reaction is usually greater than when the reaction is carried out at lower temperatures; when carried out in the presence of a tetraalkylammonium alkanoate, however, the reaction proceeds well at lower temperatures (e.g. 100°–140° C) to produce good yields of a purer product. Tetra-n-butylammonium acetate is usually the reagent of choice, but other tetraalkylammonium alkanoates may be used, e.g. tetraethylammonium acetate, tetramethylammonium acetate, tetraethylammonium formate, tetra-n-butylammonium formate, and the like. The molar quantity of tetraalkylammonium alkanoate per mole of aminoglycoside is usually from about 1.5 to about 5 moles.

The intermediates produced upon reaction of the N-protected-O-protected-5-O-hydrocarbonsulfonyl (or substituted hydrocarbonsulfonyl)-4,6-di-O-(aminoglycosyl)-2deoxystreptamine with dimethylformamide upon hydrolysis produces a 5-epi-4,6-di-O-(aminoglycosyl)-2-deoxystreptamine of this invention. When tetra-n-butylammonium acetate is used together with dimethylformamide, the intermediate produced is the corresponding N-protected-O-protected-5-epi-O-acetyl derivative which, upon hydrolysis, produces a 5-epi- compound of this invention.

Protecting groups susceptible to reductive cleavage are frequently preferentially used in carrying out my process since they can be removed with ease via reductive techniques after epimerization at the 5-position. Other protecting groups will remain after the reduction step, however, e.g. N,O-carbonyl groups which are removed upon treatment with aqueous base at elevated temperatures. Additionally, to remove acetals or ketals, acid hydrolysis is required.

When removing protecting groups susceptible to reductive cleavage from the intermediates produced in this process, reduction with hydrogen in the presence of a catalyst is preferred when the 4,6-di-O-(aminoglycosyl)-2-deoxystreptamine-N-protected-O-protected intermediates produced are devoid of unsaturation, such as the intermediates derived by treatment with dimethylformamide of O- and N-protected derivatives of gentamicins A, B, $B_1$, $C_1$, $C_{1a}$, $C_2$, $C_{2a}$, $C_{2b}$ and $X_2$, of tobramycin, kanamycins A and B, 3',4'-dideoxykanamycin B, and Antibiotics G-418, JI-20A and JI-20B. On the other hand, when removing protecting groups susceptible to reductive cleavage from N- protected-O-protected-4,6-di-O-(aminoglycosyl)-2-deoxystreptamine intermediates in which a double bond is present, such as those derived from sisomicin, verdamicin, Antibiotic G-52. Antibiotics 66-40B and 66-40D, reduction by means of an alkali metal in liquid ammonia is preferable in order to avoid reduction of the double bond.

When deblocking an intermediate with hydrogen in the presence of a catalyst, the catalyst most frequently employed is palladium, preferably palladium on charcoal.

The hydrogenolysis of protecting groups is usually carried out at room temperatures in lower alkanoic acids, preferably acetic acid, although other solvents such as lower alkanols may be used. The hydrogenation is continued until there is no further discernible drop in hydrogen pressure and the 5-epi-4,6-O-(aminoglycosyl)-2-deoxystreptamine of this invention is then usually isolated by removing the solvent such as by distillation, and thence treating the N- and O-protected-5-epi-2-deoxystreptamine intermediate thereby formed with base, and when acetals or ketals are also present, with aqueous acid to remove the remaining protecting groups.

In a typical mode of carrying out this process, a 5-O-hydrocarbonsulfonyl-per-N-protected-per-O-protected-intermediate similar to those of formulae V and VI and their 1-N-alkyl derivatives but having a hydrocarbonsulfonyloxy group at C-5 rather than an oxo-function, e.g. 1,3,2',6'-tetra-N-benzyloxycarbonyl-5-O-methanesulfonyl-2''-O-benzoyl-3'',4''-N,O-carbonylgentamicin $C_1$, is dissolved in dimethylformamide and heated at reflux temperature for 18 hours, then the solution is evaporated to a residue of a 5-epi-N-protected-O-protected-4,6-di-O-(aminoglycosyl)-2-deoxystreptamine intermediate which is dissolved in acetic acid and hydrogenated at room temperature at 60 pounds per square inch (psi) starting hydrogen pressure in the presence of 30% palladium on charcoal catalyst. When no further drop in hydrogen pressure is discernible, the catalyst is removed by filtration, and the solvent removed by distillation in vacuo to produce a residue which, upon treatment with 2 N sodium hydroxide at elevated temperatures (e.g. 100° C) followed by neutralization with acetic acid, thence isolation and purification utilizing known techniques yields 5-epigentamicin $C_1$, a novel antibacterial agent of this invention.

In another preferred mode of carrying out this process, a 5-O-hydrocarbonsulfonyl-per-N-protected-per-O-protected intermediate, e.g. 1,3,2',6'-tetra-N-benzyloxycarbonyl-5-O-methanesulfonyl-2''-O-benzoyl-3'',4''-N,O-carbonylsisomicin and 1-N-ethyl-1,3,2',6'-tetra-N-benzyloxycarbonyl-5-O-methanesulfonyl-2''-O-benzoyl-3'',4''-N,O-carbonylsisomicin, in dimethylformamide to which tetra-n-butylammonium acetate has been added, is heated at 120° C for 16 hours and the solution evaporated to give the corresponding 5-epiacetyl derivative, e.g. 1,3,2',6'-tetra-N-benzyloxycarbonyl-5-epi-O-acetyl-2''-O-benzoyl-3'',4''-N,O-carbonylsisomicin and the corresponding 1-N-ethyl derivative, which, upon treatment with aqueous potassium hydroxide followed by neutralization, thence isolation and purification via chromatographic techniques yields a 5-epi- compound, e.g. 5-episisomicin and 1-N-ethyl-5-episisomicin.

Any acetal or ketal protecting groups in the intermediates are removed after removal of the N-protecting groups by treatment with dilute aqueous acid, e.g. with dilute mineral acids, dilute trifluoroacetic acid, or usually with dilute alkanoic acids, such as acetic acid.

When removing carbobenzyloxy protecting groups from a per-N-protected-per-O-protected aminoglycoside intermediate having a double bond (e.g. the intermediate derived from 1,3,2',6'-tetra-N-benzyloxycarbonyl-2''-O-benzoyl-3'',4''-N,O-carbonylverdamicin, upon treatment with dimethylformamide) by reaction thereof with an alkali metal (e.g. potassium, lithium, and preferably, sodium) in liquid ammonia, the intermediate is usually dissolved in a mixture of a co-solvent such as tetrahydrofuran and liquid ammonia to which the alkali metal (e.g. sodium) is added and the reaction mixture stirred for a few hours. After allowing the ammonia to evaporate, any remaining O- and N-protecting groups (such as the 3'',4''-N,O-carbonyl and the 2''-O-benzoyl group) are removed by addition of water to the reaction mixture affording sodium hydroxide and heating at elevated temperatures (e.g. 100° C). Purification of the resulting product is effected via chromatographic techniques to obtain an antibacterially active 5-epi-aminoglycoside of this invention, e.g. 5-epiverdamicin.

Alternatively, in my process, the protecting groups may be removed from the N- and O-protected intermediate produced upon treatment with dimethylformamide of an N- and O-protected 5-O-hydrocarbonsulfonyl-4,6-di-O-(aminoglycosyl)-2-deoxystreptamine, by reaction thereof with base at elevated temperatures, and, when acetals or ketals are present, by treatment with aqueous acid.

The 5-O-hydrocarbonsulfonyl and 5-O-substituted hydrocarbonsulfonyl ester intermediates useful in this process are those derived from hydrocarbonsulfonic acids having up to 8 carbon atoms including ethanesulfonic acid, benzenesulfonic acid, p-toluenesulfonic acid, and preferably methanesulfonic acid; also those derived from nitrobenzenesulfonic acids (e.g. o, m, and p-nitrobenzenesulfonic acids) and those derived from halogenohydrocarbonsulfonic acids (e.g. trifluoromethane sulfonic acid, p-chlorobenzenesulfonic acid, o or p-bromobenzenesulfonic acids and the like). The 5-O-hydrocarbonsulfonyl and 5-O-substituted hydrocarbonsulfonyl intermediates are prepared from the corresponding per-N-protected-per-O-protected-aminoglycosides having a free 5-hydroxyl group (i.e. compounds of formulae V - XII and 1-N-alkyl derivatives thereof devoid of the 5-oxo-function but having a 5-hydroxyl function) by treatment thereof with a hydrocarbonsulfonyl halide (preferably methanesulfonylchloride) in a tertiary amine (usually triethylamine).

The per-N-protected-per-O-protected-5-O-hydrocarbonsulfonyl-4,6-di-O-(aminoglycosyl)-2-deoxystreptamine precursors for the process are derived from known, unprotected-4,6-di-O-(aminoglycosyl)-2-deoxystreptamines including 4-O-aminoglycosyl-6-O-garosaminyl-2-deoxystreptamine antibiotics such as gentamicin B, gentamicin $B_1$, gentamicin $C_1$, gentamicin $C_{1a}$, gentamicin $C_2$, gentamicin $C_2a$, gentamicin $C_2b$, gentamicin $X_2$, sisomicin, verdamicin, Antibiotic G-418, Antibiotic JI-20A, Antibiotic JI-20B, and Antibiotic G-52; and 4,6-di-O-(aminoglycosyl)-2-deoxystreptamines such as gentamicin A, tobramycin, Antibiotic 66-40B and Antibiotic 66-40D, kanamycin A, kanamycin B and 3',4'-dideoxykanamycin B. Of the foregoing, preferred starting antibiotic precursors are gentamicins $C_1$, $C_{1a}$, $C_2$, $C_{2a}$, $C_{2b}$, Antibiotic 66-40D, verdamicin, Antibiotic G-52, and sisomicin, all of which are most easily converted to preferred compounds of this invention, i.e. to the corresponding 5-epimers.

The aforementioned 4,6-di-O-(aminoglycosyl)-2-deoxy-streptamine antibiotics are known. Of the gentamicins, the starting compound referred to herein as gentamicin $X_2$ is also known in the art as gentamicin X. The starting compound referred to herein as gentamicin $C_2a$ is isolated and characterized as set forth herein in Preparation 1.

The starting compound referred to herein as gentamicin $C_2b$, isolated and characterized as set forth in Preparation 2, and having the structural formula shown herein, is named in some prior art as gentamicin $C_2a$.

When preparing the 1-N-K-5-epi-4,6-di-O-(aminoglycosyl)-2-deoxystreptamines of this invention, the 1-N-K per-N-protected-per-O-protected-5-O-hydrocarbonsulfonyl-4,6-di-O-(aminoglycosyl)-2-deoxystreptamine precursors are also derived from the 1-N-alkyl (i.e. the 1-N-K) derivatives of the aforedescribed 1-N-unsubstituted-4,6-di-O-(aminoglycosyl)-2-deoxystreptamines. The 1-N-K-aminoglycosides are known compounds being described in Belgian Patent No. 818,431 and in co-pending application U.S. Ser. No. 492,998 filed July 30, 1974 of John J. Wright et al of common assignee as the instant application.

Included among the alkyl substituents contemplated for the moiety "K" in the starting compounds and in the novel 1-N-K-5-epi-4,6-di-O-(aminoglycosyl)-2-deoxystreptamines of this invention are straight and branched chain alkyl groups such as ethyl, n-propyl, n-butyl, $\beta$-methylpropyl, n-pentyl, $\beta$-methylbutyl, $\gamma$-methylbutyl and $\beta,\beta$-dimethylpropyl: n-hexyl, $\delta$-methylpentyl, $\beta$-ethylbutyl, $\gamma$-ethylbutyl, n-heptyl, $\epsilon$-methylheptyl, $\beta$-ethylpentyl, $\gamma$-ethylpentyl, $\delta$-ethylpentyl, $\gamma$-propylbutyl, n-octyl, iso-octyl, $\beta$-ethylhexyl, $\delta$-ethylhexyl, $\epsilon$-ethylhexyl, $\beta$-propylpentyl, $\gamma$-propylpentyl; alkyl cycloalkyl groups such as cyclopropylmethyl, cyclopentylmethyl, cyclohexylmethyl and cyclopentylethyl; alkenyl groups such as $\beta$-propenyl, $\beta$-methylpropenyl, $\beta$-butenyl, $\beta$-methyl-$\beta$-butenyl, $\beta$-ethyl-$\beta$-hexenyl: aralkyl groups such as benzyl, o-tolyl, m-tolyl, p-tolyl and phenylethyl: hydroxy substituted straight and branched chain alkyl groups such as $\epsilon$-hydroxypentyl, $\beta$-hydroxy-$\gamma$-methylbutyl, $\beta$-hydroxy-$\beta$-methylpropyl, $\delta$-hydroxybutyl, $\beta$-hydroxypropyl, $\gamma$-hydroxypropyl, $\omega$-hydroxyoctyl: amino substituted straight and branched chain alkyl groups such as $\epsilon$-aminopentyl, $\beta$-aminopropyl, $\gamma$-aminopropyl, $\delta$-aminobutyl, $\beta$-amino-$\gamma$-methylbutyl and $\omega$-aminooctyl and mono-N-alkylated derivatives thereof such as the N-methyl, N-ethyl, and N-propyl derivatives, e.g. $\epsilon$-methylaminopentyl, $\beta$-methylaminopropyl, $\beta$-ethylaminopropyl, $\delta$-methylaminobutyl, $\beta$-methylamino-$\gamma$-methylbutyl, and $\omega$-methylaminobutyl: amino and hydroxy disubstituted straight and branched chain alkyl groups such as $\beta$-hydroxy-$\epsilon$-aminopentyl, $\gamma$-hydroxy-$\gamma$-methyl-$\delta$-aminobutyl, $\beta$-hydroxy-$\delta$-aminobutyl, $\beta$-hydroxy-$\gamma$-aminopropyl, and $\beta$-hydroxy-$\beta$-methyl-$\gamma$-aminopropyl: and mono-N-alkylated derivatives thereof such as $\beta$-hydroxy-$\epsilon$-methylaminopentyl, $\gamma$-hydroxy-$\gamma$-methyl-$\delta$-methylaminobutyl, $\beta$-hydroxy-$\delta$-methylaminobutyl, $\beta$-hydroxy-$\gamma$-ethylaminopropyl, and $\beta$-hydroxy-$\beta$-methyl-$\gamma$-methyl aminopropyl.

Of the foregoing alkyl substituents contemplated for the moiety K, preferred are lower alkyl substituents having up to 4 carbon atoms, especially those having 2 to 4 carbon atoms, particularly valuable derivatives being 1-N-ethyl- and 1-N-propyl-5-epi-4,6-di-O-(aminoglycosyl)-1,3-diaminocyclitols of this invention.

When preparing the per-N-protected-per-O-protected-5-O-hydrocarbonsylfonyl-4,6-di-O-(aminoglycosyl)-2-deoxystreptamine starting compounds for my process, the amino groups are usually protected first by formation of amides susceptible to reductive cleavage or basic hydrolysis. For the processes of this invention, I prefer to protect the amino groups by forming N-benzyloxycarbonyl derivatives thereof (e.g. 1,3,2',6',3'-penta-N-benzyloxycarbonylgentamicin $C_{1a}$ and 1,3,6',3''-tetra-N-benzyloxycarbonylgentamicin B).

The per-N-protected aminoglycosides thereby formed which have a garosaminyloxy radical at C-6 are then treated with an alkali metal hydride usually sodium hydride in dimethylformamide, whereby the 3''-N-benzyloxycarbonyl protecting group is cyclized with the 4''-hydroxy function to form an oxazolidinone derivative, i.e. a 3'',4''-N,O-carbonyl derivative. In aminoglycosides wherein other amino groups are adjacent to a hydroxyl group (such as the 6'-amino and 4'-hydroxyl groups in gentamicin B), other N,O-carbonyl derivatives will be formed. Thus, upon reaction of each of 1,3,2',6',3''-penta-N-benzyloxycarbonylgentamicin $C_{1a}$ and of 1,3,6',3''-tetra-N-benzyloxycarbonylgentamicin B with sodium hydride in dimethylformamide, there are formed oxazolidinone derivatives, i.e. 1,3,2',6'-tetra-N-benzyloxycarbonyl 3'',4''-N,O-carbonylgentamicin $C_{1a}$ and 1,3-di-N-benzyloxycarbonyl-6',4';3'',4''-di-N,O-carbonylgentamicin B.

Alternatively, when protecting amino groups from antibacterial agents which cannot form a 3'',4''-N,O-carbonyl derivative (e.g. intermediates not having a 6-O-garosaminyl substituent such as gentamicin A and 3',4'-dideoxykanamycin B), the amino groups are conveniently protected by lower alkanoyl groups such as acetyl and propionyl by treatment of the antibacterial agent with the corresponding acid anhydride in ethanol whereby is produced the corresponding per-N-lower alkanoyl aminoglycoside. Thus, for example, treatment of gentamicin A with acetic anhydride in ethanol yields per-N-acetylgentamicin A.

I usually next protect adjacent hydroxyl groups which will form a ketal or acetal group upon treatment with a ketone or aldehyde or derivative thereof in dimethylformamide in the presence of catalytic amounts of a strong acid such as p-toluenesulfonic acid utilizing known techniques. Thus, 1,3-di-N-benzyloxycarbonyl-6',4';3'',4''-N,O-carbonylgentamicin B, upon treatment with 1,1-dimethoxycyclohexane in dimethylformamide in the presence of p-toluenesulfonic acid, yields the ketal of the hydroxyl groups at C-2' and C-3' to produce 1,3-di-N-benzyloxycarbonyl-2',3'-O-cyclohexylidene-6',4';3'',4''-di-N,O-carbonylgentamicin B. Finally, any isolated hydroxyl functions (except the 5-hydroxyl group) remaining in the partially protected aminoglycoside derivatives are converted to the corresponding hydrocarboncarbonyl derivatives by treatment thereof with an acid chloride of the hydrocarboncarboxylic acid in a tertiary amine (preferably triethylamine), the molar quantity of acid halide reagent being based upon the number of hydroxyl groups to be esterified. If only one hydroxyl group other than the 5-hydroxy remains in the molecule (e.g. the 2''-hydroxy) an equivalent quantity of acid halide to the molar quantity of aminoglycoside is used; if two hydroxyl groups remain to be protected, two molar equivalents of acid halide are used per mole of aminoglycoside. Acyl halides of hydrocarboncarboxylic acids having up to 8 carbon atoms are preferentially used, including acid chlorides of lower alkanoic acids such as acetic, propionic, valeric, and caprylic acids; of aralkanoic acids such as phenylacetic acid and arylcarboxylic acids such as toluic and, preferably benzoic acids. Thus, each of the aforenamed intermediates of gentamicin $C_1$ and B upon treatment with equimolar quantities of benzoylchloride in pyridine, yields the corresponding 2''-O-benzoyl derivatives, i.e. 1,3,2',6'-tetra-N-benzyloxycarbonyl-2''-O-benzoyl-3'',4''-N,O-carbonylgentamicin $C_1$ and 1,3-di-N-benzyloxycarbonyl-2',3'-O-cyclohexylidene-6',4';3'',4''-di-N,O-carbonyl-2''-O-benzoylgentamicin B, both of which, upon treatment with methanesulfonylchloride in triethylamine yields the corresponding 5-O-methanesulfonyl derivatives, requisite starting compounds for the foregoing process of this invention.

It is apparent from the foregoing that, by my invention, known 4,6-di-O-(aminoglycosyl)-2-deoxystreptamine antibacterial agents and their 1-N-alkyl derivatives are converted to the corresponding N-protected-O-protected-4,6-di-O-(aminoglycosyl)-2-deoxystreptamine having a free 5-hydroxyl group which, in turn, are converted to the corresponding 5-O-hydrocarbonsulfonyl derivatives. Treatment of the 5-O-hydrocarbonsulfonyl-N-protected-O-protected precursor with dimethylformamide, preferably in the presence of tetra-n-butylammonium acetate, at temperatures in the range of 80° to 153° C, yields an N-protected-O-protected-5-epi-4,6-di-O-(aminoglycosyl)-2-deoxystreptamine intermediate which, upon treatment at elevated temperatures with aqueous base and, when acetals or ketals are present, also with dilute aqueous acid, yields the antibacterially active 5-epi-4,6-di-O-(aminoglycosyl)-2-deoxystreptamines of formulae I–IV and the 1-N-alkyl derivatives thereof. Alternatively, when groups susceptible to reductive cleavage are present, treatment of the intermediate with a reducing agent selected from the group consisting of hydrogen in the presence of a catalyst, or with an alkali metal in liquid ammonia followed by treatment of the product thereby formed with aqueous base at elevated temperatures, and optionally, when acetals or ketals are present, with aqueous acid, yields the antibacterially active 5-epi-4,6-di-O-(aminoglycosyl)-2-deoxystreptamines of formulae I – IV and 1-N-alkyl derivatives thereof.

In another process aspect of this invention, the antibacterially active 5-epi-4,6-di-O-(aminoglycosyl)-2-deoxystreptamines of formulae I, II, III and IV and their 1-N-alkyl derivatives are prepared from the corresponding 4,6-di-O-(aminoglycosyl)-2-deoxystreptamine having a free hydroxyl group at C-5 and having all other hydroxyl functions and all amino functions protected by groups susceptible to reductive cleavage or to basic or mild acid hydrolysis, by reaction thereof with an oxidizing agent, e.g. ruthenium tetroxide, chromic acid in acetone; or chromium trioxide-pyridine complex in methylene chloride; thence reaction of the thereby formed 5-dehydro-4,6-di-O-(aminoglycosyl)-2-deoxystreptamine having O- and N-protecting groups (novel intermediates such as defined by formulae V to XII hereinabove and their 1-N-alkyl derivatives with an alkali metal borohydride; followed by removal of the protecting groups by reaction of the resulting per-N-protected-per-O-protected-5-epi-4,6-di-O-(aminoglycosyl)-2-deoxystreptamine with aqueous base or, when protecting groups susceptible to reductive cleavage are present, by treatment with hydrogen in the presence of a catalyst or with an alkali metal in liquid ammonia followed by treatment with base, thence, when acetals or ketals are present, removal of the remaining O-protecting groups with aqueous acid.

The oxidation step of this process is usually carried out in an organic solvent such as acetone when chromic acid is used, or a halogenated hydrocarbon, preferably methylene chloride, when chromium trioxide-pyridine complex or ruthenium tetroxide is used as oxidizing agent, at temperatures in the range of from about 0° C to about 40° C, preferably at 20° C to 40° C.

In the second step of this process whereby the per-N- and O-protected-5-dehydro-4,6-di-O-(aminoglycosyl) intermediate is reduced to produce the corresponding 5-epi intermediate, hindered alkali metal borohydrides are preferred reagents, e.g. sodium, potassium or lithium tri-sec-butyl borohydrides, although any alkali metal borohydride may be used, e.g. sodium or potassium borohydride. The reaction is usually carried out in a lower alkanol (e.g. methanol) or ether (e.g. dioxane or preferably tetrahydrofuran) at temperatures in the range of from about 0° C to about 50° C (preferably at 0° C to 25° C) under conditions known in the art for carrying out alkali metal borohydride reductions.

In a typical mode of carrying out this process aspect of my invention a per-N-protected-O-protected-4,6-di-O-(aminoglycosyl)-2-deoxystreptamine (e.g. 1,3,2',6',-3''-penta-N-benzyloxycarbonyl-2''-O-acetylgentamicin $C_{1a}$), dissolved in methylene chloride is treated with chromium trioxide-pyridine complex at room temperature until the reaction is complete as determined by thin layer chromatographic analysis of an aliquot of the reaction mixture (usually about 28 hours reaction time). The resulting 5-keto intermediate, i.e. the O-protected-per-N-protected-5-dehydro-4,6-di-O-(aminoglycosyl)-2-deoxystreptamine, e.g. 1,3,2',6',3''-penta-N-benzyloxycarbonyl-5-dehydro-2''-O-acetylgentamicin $C_{1a}$, is conveniently isolated by extraction with ether, evaporating the solvent, and purifying the residue via chromatographic techniques. The 5-keto-intermediate is then dissolved in a lower alkanol or ether, preferably tetrahydrofuran and an alkali metal hydride (e.g. lithium tri-sec.-butyl borohydride) added (usually 2 to 4 moles of metal borohydride is used per mole of aminoglycoside intermediate) and the reaction mixture stirred at room temperature for about 20 hours. The N-protected-O-protected-5-epi-aminoglycoside thereby formed is usually isolated by adding saline to the reaction mixture extracting with ethyl acetate, thence evaporating the solvent. The N- and O-protecting groups in the 5-epi-aminoglycoside intermediate are then removed, for example, by treatment with sodium in liquid ammonia to remove the benzyloxycarbonyl groups followed by treatment with sodium hydroxide at elevated temperatures.

OTHER METHODS OF PREPARING 1-N-ALKYL-5-EPI-4,6-DI-O-(AMINOGLYCOSYL-1,3-DIAMINOCYCLITOLS

In addition to the foregoing processes of this invention, the 1-N-K-5-epi-4,6-di-O-(aminoglycosyl)-2-deoxystreptamines of this invention may be prepared from the corresponding 1-N-unsubstituted-5-epi-4,6-di-O-(aminoglycosyl)-2-deoxystreptamine via methods similar to those described in Belgian Patent No.

818,431 and in co-pending application U.S. Ser. No. 492,998 filed July 30, 1974 of John J. Wright et al of common assignee as the instant application.

In one of these processes, the 1-N-K derivatives of the 5-epi-4,6-di-O-(aminoglycosyl)-1,3-diaminocyclitols of formulae I, II, III and IV are prepared by treating an acid addition salt of the corresponding 1-N-unsubstituted-4,6-di-(aminoglycosyl)-1,3-diaminocyclitol antibacterial agent with about one molar equivalent of a hydride-donor reducing agent in an inert solvent (preferably a protic solvent in the presence of water) and in the presence of at least one molar equivalent of an aldehyde having the formula K'CHO wherein K' is a member selected from the group consisting of hydrogen and an alkyl substituent selected from the group consisting of alkyl, alkenyl, cycloalkyl, aralkyl, hydroxyalkyl, aminoalkyl, alkylaminoalkyl, aminohydroxyalkyl, and alkylaminohydroxyalkyl, said alkyl substituent having up to 7 carbon atoms, and, when said alkyl substituent is substituted by both hydroxyl and amino functions, only one of said functions can be attached to any one carbon atom, and wherein any amino function in said alkyl substituent is preferably protected with an acyl group.

This process, whereby the 1-amino function in an acid addition salt of a 1-N-unsubstituted-5-epi-4,6-di-O-(aminoglycosyl)-1,3-diaminocyclitol antibacterial agent is selectively condensed with an aldehyde and concomitantly reduced in situ to form a 1-N-alkyl-5-epi-4,6-di-O-(aminoglycosyl)-1,3-diaminocyclitol antibacterial agent, is usually carried out at room temperature in the presence of air, although it may be advantageously carried out under an inert atmosphere (e.g. argon or nitrogen).

Hydride-donor reducing agents include dialkylaminoboranes (e.g. dimethylaminoborane, diethylaminoborane and preferably morpholinoborane), tetraalkylammonium cyanoborohydride (e.g. tetrabutylammonium cyanoborohydride), alkali metal borohydride (e.g. sodium borohydride) and preferably, alkali metal cyanoborohydride (e.g. lithium cyanoborohydride and sodium cyanoborohydride).

This process is conveniently carried out at ambient temperatures in an inert solvent. By "inert solvent" is meant any organic or inorganic solvent in which the 5-epi-4,6-di-O-(aminoglycosyl)-1,3-diaminocyclitol starting compounds and the reagents are soluble, and which will not interfere with the process under the reaction conditions thereof so there are produced a minimum of competing side reactions. Although anhydrous aprotic solvents may sometimes advantageously be employed in this process (such as tetrahydrofuran when utilizing morpholinoborane as hydride-donor reducing agent) this process is usually carried out in protic solvents e.g. in a lower alkanol or, preferably, in water or in an aqueous lower alkanol (e.g. aqueous methanol, aqueous ethanol), although other water-miscible co-solvent systems may be employed such as aqueous dimethylformamide, aqueous hexamethylphosphoramide, aqueous tetrahydrofuran and aqueous ethylene glycol dimethyl ether.

The acid addition salts of the 1-N-unsubstituted-5-epi-4,6-di-O-(aminoglycosyl)-1,3-diaminocyclitols, requisite starting compounds, may be derived from any organic acid such as acetic acid, trifluoroacetic acid, or p-toluenesulfonic acid or from any inorganic acid such as hydrochloric acid, sulfuric acid, phosphoric acid, or nitric acid. It is usually most convenient to use the addition salts derived from sulfuric acid. Optimum results are achieved when all amino groups present in the molecule are fully neutralized; however, this process may be carried out using 5-epi-4,6-di-O-(aminoglycosyl)-1,3-diaminocyclitol acid addition salts which are not fully protonated or, alternatively, on fully protonated compounds in the presence of excess acid. It is usually convenient to prepare the requisite acid addition salt starting compound in situ by adding the desired acid (e.g. sulfuric acid) to a solution or suspension of the 5-epi-4,6-di-O-(aminoglycosyl)-1,3-diaminocyclitol (e.g. 5-episisomicin) in a protic solvent (e.g. water) until the pH of the solution is in the range of from about 2 to about 5, preferably from about pH 2.5 to about pH 3.5. This process proceeds best within this range, but may be carried out at pH values in the range of from about pH 1 to about pH 11.

The starting acid addition salts of this process can be derived from any 5-epi-4,6-di-O-(aminoglycosyl)-1,3-diaminocyclitol which has a free amino group at the 1-position and which exhibits antibacterial activity against gram positive and/or gram negative organisms as determined by conventional in vitro techniques such as broth dilution tests, agar dilution tests, disc diffusion tests, and the like. A 4,6-di-O-(aminoglycosyl)-1,3-diaminocyclitol which inhibits bacteria at concentrations equal to or less than about 50 to about 100 mcg./ml. is considered to be an antibacterial agent.

Typical aldehydes of the formula K' CHO wherein K' is as above defined which are useful in this process include straight and branched chain alkyl aldehydes such as formaldehyde, acetaldehyde, n-propanal, n-butanal, 2-methylpropanal, n-pentanal, 2-methylbutanal, 3-methylbutanal, 2,2-dimethylpropanal, n-hexenal, 2-ethylbutanal, n-heptanal and n-octanal: cycloalkylaldehydes such as cyclopropanecarboxaldehyde, cyclopentanecarboxaldehyde, cyclopentaneacetaldehyde, and cyclohexanecarboxaldehyde: alkenyl aldehydes such as propenal, 2-methylpropenal, 2-butenal, 2-methyl-2-butenal, 2-ethyl-2-hexenal: aralkyl aldehydes such as benzaldehyde, o,m, and p-tolualdehydes and phenylacetaldehyde: hydroxy substituted straight and branched chain alkyl aldehydes such as 5-hydroxypentanal, 2-hydroxy-3-methylbutanal, 2-hydroxy-2-methylpropanal, 4-hydroxybutanal, 2-hydroxypropanal and 8-hydroxyoctanal: amino substituted straight and branched chain alkyl aldehydes such as 5-aminopentanal, 2-aminopropanal, 3-aminopropanal, 4-aminobutanal, 2-amino-3-methylbutanal, 8-aminooctanal and mono-N-alkyl derivatives thereof; and amino and hydroxy disubstituted straight and branched chain alkyl aldehydes such as 2-hydroxy-5-aminopentanal, 3-hydroxy-3-methyl-4-aminobutanal, 2-hydroxy-4-aminobutanal, 2-hydroxy-3-aminopropanal, 2-hydroxy-2-methyl-3-aminopropanal, 2-amino-3-hydroxyoctanal, and mono-N-alkyl derivatives thereof.

In this process, if the aldehyde possesses a chiral center, one can use each enantiomer separately or together as a racemate and there will be obtained the respective diastereoisomers or a mixture thereof, respectively.

The aldehyde reagents useful in this process are either known compounds or are easily prepared from known compounds utilizing procedures well known in the art. Thus, for example, alkylaldehydes substituted by both hydroxyl and amino functions (e.g. 2-hydroxy-5-aminopentanal) may be prepared from an aminoaldehyde acetal (e.g. 4-aminobutanal diethylacetal)

by protecting the amino function therein as an acetamido or phthalimido group utilizing known procedures followed by removal of the acetal function by acid hydrolysis thereby obtaining an N-protected aminoaldehyde (e.g. by converting 4-aminobutanal diethylacetal to the corresponding N-phthalimido derivative which upon acid hydrolysis yields 4-phthalimidobutanal). Treatment of the N-protected aminoaldehyde with hydrocyanic acid yields the corresponding N-protected-aminoalkyl hydroxynitrile (e.g. 2-hydroxy-5-phthalimidovaleronitrile) which upon catalytic reduction (e.g. hydrogen in the presence of palladium) or by hydride reduction (e.g. with diisobutylaluminum hydride) yields an N-protected amino-hydroxy aldehyde (e.g. 2-hydroxy-5-phthalimido-pentanal) which is an aldehyde reagent used in this process.

When carrying out this process, in order to minimize competing side reactions when an aminoaldehyde is used as reagent, it is preferable to protect the amino function in the aldehyde, e.g. with an acyl blocking group such as acetamido, phthalimido, or the like, prior to carrying out this process, and thence removing the N-protecting group in the 5-epi-1-N-(protected aminoalkyl)-4,6-di-O-(aminoglycosyl)-1,3-diaminocyclitol thereby produced. It may also be advantageous to protect the hydroxyl group in hydroxyl-containing aldehydes when carrying out this process; however, it is not generally necessary.

A convenient method of carrying out this process comprises preparing a solution of a 1-N-unsubstituted-5-epi-4,6-di-O-(aminoglycosyl)-1,3-diaminocyclitol antibacterial agent (e.g. 5-episisomicin) in a protic solvent, (preferably water), and adjusting the pH of the solution to from about pH 2 to about pH 5 with an acid (usually dilute sulfuric acid) thereby preparing the requisite acid addition salt of the starting compound. When the pH of the solution is at about pH 5, the acid addition salt thereby produced usually contains about one equivalent of acid for each amino function in the 5-epi-4,6-di-O-(aminoglycosyl)-1,3-diaminocyclitol (e.g. per mole of 5-episisomicin there is present 2.5 moles of sulfuric acid). After the acid addition salt solution is prepared, there is added at least a molar equivalent, and preferably a large molar excess of the desired aldehyde (e.g. acetaldehyde) followed within a short time (usually in about 5 minutes) by the addition of about a molar equivalent (based upon the starting 4,6-di-(aminoglycosyl)-1,3-diaminocyclitol) of a hydride-donor reducing reagent, preferably an alkali metal cyanoborohydride, usually sodium cyanoborohydride. The reaction is frequently completed in less than 30 minutes as determined by thin layer chromatography and there is obtained the corresponding 5-epi-1-N-alkyl-4,6-di-O-(aminoglycosyl)-1,3-diaminocyclitol (e.g. 1-N-ethyl-5-episisomicin) having enhanced antibacterial activity. Isolation and purification of the 1-N-alkyl derivative thereby produced is effected utilizing known techniques such as precipitation, extraction and, preferably, chromatographic techniques.

Alternatively, in the foregoing process, partially N-protected intermediates may be utilized. Thus, for example, one may utilize as starting compound a 1-N-unsubstituted-5-epi-4,6-di-O-(aminoglycosyl)-1,3-diaminocyclitol wherein the amino function at the 6'-carbon is N-protected (e.g. the sulfuric acid addition salt of 6'-N-t-butoxycarbonyl-5-episisomicin) or a 1-N-unsubstituted-5-epi-4,6-di-O-(aminoglycosyl)-1,3-diaminocyclitol wherein the amino functions at C-2' and C-3 are N-protected (e.g. the sulfuric acid addition salt of 2',3-di-N-trifluoroacetyl-5-epigentamicin $C_1$) and there will be formed the corresponding partially N-protected-1-N-alkyl derivative (e.g. 1-N-ethyl-6'-N-t-butoxycarbonyl-5-episisomicin and 1-N-ethyl-2',3-di-N-trifluoroacetyl-5-epigentamicin $C_1$, respectively) which upon removal of the N-protecting groups, according to known methods, yields 1-N-alkyl-5-epi compounds of this invention, e.g. 1-N-ethyl-5-episisomicin and 1-N-ethyl-5-epigentamicin $C_1$, respectively.

Additionally, the 1-N-alkyl-5-epi-4,6-di-O-(aminoglycosyl)-1,3-diaminocyclitols are prepared by reducing a Schiff base derivative of the 1-amino function in a partially N-protected-5-epi-4,6-di-O-(aminoglycosyl)-1,3-diaminocyclitol followed by removal of the N-protecting groups. Thus, for example, 2',3-di-N-trifluoroacetyl-5-epigentamicin $C_1$ upon reaction with an aldehyde (e.g. benzaldehyde, phenylacetaldehyde or acetaldehyde) is converted to the corresponding 3'',4''-oxazolidine-1-ylidene Schiff base (e.g. 1,N-3'',4''-N,O-di-benzylidene-2',3-di-N-trifluoroacetyl-5-epigentamicin $C_1$, 1,N-3'',4''-N,O-di-phenethylidene-2',3-di-N-trifluoroacetyl-5-epigentamicin $C_1$ and 1,N,3'',4''-N,O-diethylidene-2',3-di-N-trifluoroacetyl-5-epigentamicin $C_1$) which, upon reduction with sodium borohydride and methanolic sodium methoxide yields the corresponding 1-N-alkyl-3'',4''-oxazolidine (e.g. 1-N-benzyl-3''-N-4''-O-benzylidene-5-epigentamicin $C_1$, 1-N-phenethyl-3''-N-4''-O-phenethylidene-5-epigentamicin $C_1$ and 1-N-ethyl-3''-N-4''-O-ethylidene-5-epigentamicin $C_1$, respectively) which upon treatment with acid yields a 1-N-alkyl-5-epi compound of our invention, (e.g. 1-N-benzyl-5-epigentamicin $C_1$, 1-N-phenethyl-5-epigentamicin $C_1$ and 1-N-ethyl-5-epigentamicin $C_1$, respectively.

In these processes, suitable as N-protecting groups are those groups known in the art to be easily removable after preparation of the 1-N-alkyl-5-epi-4,6-di-O-(aminoglycosyl)-1,3-diaminocyclitol of our invention without affecting the 1-N-alkyl substituents therein. Exemplary of such amino protecting groups are 2,4-dinitrophenyl; acyl groups such as acetyl, propionyl and benzoyl; alkoxycarbonyl groups such as methoxycarbonyl ethoxycarbonyl, 2,2,2-trichloroethoxycarbonyl, t-butoxycarbonyl and 2-iodoethoxycarbonyl; and arylalkoxycarbonyl groups such as benzyloxycarbonyl and 4-methoxybenzyloxycarbonyl groups.

Another process for the preparation of 1-N-substituted derivatives of the 5-epi-4,6-di-O-(aminoglycosyl)-1,3-diaminocyclitols listed above wherein the substituent is straight chain alkyl having up to five carbon atoms and of the pharmaceutically acceptable acid addition salts thereof comprises reacting one of the aforementioned 5-epi-4,6-di-O-(aminoglycosyl)-1,3-diaminocyclitols, which possesses amino-protecting groups at all positions other than position 1, and wherein the 1-amino group may be activated, with an alkylating agent containing the straight chain alkyl group having up to five carbon atoms and a leaving group, removing the protecting groups and, if required, the activating group or groups present in the molecule, and isolating the derivative as such or as a pharmaceutically acceptable acid addition salt.

Examples of alkylating agents advantageously used in this process are alkyl iodide, alkyl bromide, dialkyl sulfate, alkyl fluorosulphonate and alkyl p-toluenesulfonate wherein the alkyl group is the required straight chain alkyl group having up to five carbon atoms. Other alkylating agents, wherein the alkyl group preferably has one or two carbon atoms, are trialkylanilinium hydroxide, trialkyloxonium fluoroborate, trialkylsulfonium fluoroborate, or trialkylsulfoxonium fluoroborate. All of these alkylating agents contain a good leaving group, such as $Br^-$, $I^-$, $OSO_2F^-$, dialkylaniline or dialkylether.

The amino group in position 1 of the 5-epi-4,6-di-O-(aminoglycosyl)-1,3-diaminocyclitol can be free or activated. An example of an activating group is trifluoromethylsulfonyl. These activating groups may be introduced into the molecule by reacting a 4,6-di-(aminoglycosyl)-1,3-diaminocyclitol which possesses amino-protecting groups at any position other than position 1, e.g. 3''-N-4''-O-carbonyl-2',3,6'-tri-N-t-butoxycarbonyl-5-episisomicin, with a compound providing the activating group, such as trifluoromethylsulfonyl chloride.

The 1-amino group can also be alkylated by way of the corresponding di-(2-cyanoethyl)-derivative which is derived by treatment with acrylonitrile of the 4,6-di-(aminoglycosyl)-1,3-diaminocyclitol which possesses amino protecting groups at any position other than position 1. The 1-N-di-(2-cyanoethyl)derivative thus prepared is then alkylated with one of the above listed alkylating agents followed by removal of the cyanoethyl groups.

The process of the invention is carried out under conditions similar to those employed in the well-known direct alkylation procedures of amines.

Yet other processes for the preparation of 1-N-substituted derivatives of the 5-epi-4,6-di-O-(aminoglycosyl)-1,3-diaminocyclitols listed above, wherein the substituent is methyl, and of the pharmaceutically acceptable acid addition salts thereof, comprise reacting one of these 5-epi-4,6-di-O-(aminoglycosyl)-1,3-diaminocyclitols which possesses amino-protecting groups at all positions other than position 1, either with formaldehyde and a cyclic imide, preferably succinimide, and treating the so-obtained compound with a hydride-donor reducing agent, preferably sodium borohydride.

A process for the preparation of a 1-N-substituted derivative of the 5-epi-4,6-di-O-(aminoglycosyl)-1,3-diaminocyclitols listed above, wherein the substituent is 2-hydroxyethyl, and of the pharmaceutically acceptable acid addition salts thereof comprises reacting one of these 5-epi-4,6-di-O-(aminoglycosyl)-1,3-diaminocyclitols which possesses amino protecting groups at all positions other than position 1, with ethylene oxide, removing all protecting groups present in the molecule and isolating the derivatives as such or as a pharmaceutically acceptable acid addition salt.

Another method for preparing the 1-N-alkyl derivatives of the 5-epi-4,6-di-O-(aminoglycosyl)-1,3-diaminocyclitols such as defined by formulae I, II, III and IV, comprises treating with an amide-reducing hydride reagent, in a non-reactive organic solvent, the corresponding 1-N-acyl-5-epi-4,6-di-O-(aminoglycosyl)-1,3-diaminocyclitol, said acyl having the formula K'-CO- wherein K' is a member selected from the group consisting of hydrogen and an alkyl substituent selected from the group consisting of alkyl, cycloalkyl, alkenyl, aralkyl, hydroxyalkyl, aminoalkyl, alkylaminoalykl, aminohydroxyalkyl, and alkylaminohydroxyalkyl, said alkyl substituent having up to 7 carbon atoms, and, when said alkyl substituent is substituted by both hydroxyl and amino functions, only one of said functions can be attached to any one carbon atom.

By non-reactive organic solvents are contemplated solvents in which the 1-N-acyl-5-epi-4,6-di-O-(aminoglycosyl)-1,3-diaminocyclitol and the amide-reducing reagent are soluble and which will not react with the reagent so there is produced a minimum of competing side reactions. Non-reactive organic solvents which are most useful in our reduction process are ethers such as dioxane, tetrahydrofuran, DYGLYME (i.e. diethyleneglycol dimethyl ether) and the like.

Preferred amide-reducing hydride reagents are aluminum hydrides and borohydrides including lithium aluminum hydride, lithium trimethoxy aluminum hydride, aluminum hydride, diborane, di-isoamylborane, and 9-BBN (i.e. 9-borabicyclo[3.3.1]nonane).

In general, diborane is preferably used as the amidereducing agent except when the starting compound possesses a double bond, e.g. as in 1-N-acyl-5-episisomicin, 1-N-acyl-5-epiverdamicin, 1-N-acyl-5-epi-Antibiotic 66-40B, 1-N-acyl-5-epi-Antibiotic 66-40D, and 1-N-acyl-5-epi-Antibiotic G-52, which compounds are conveniently reduced by means of lithium aluminum hydride.

In this process whereby a 1-N-acyl-5-epi-4,6-di-O-(aminoglycosyl)-1,3-diaminocyclitol is reduced to the corresponding 1-N-alkyl derivative of the invention, if the acyl side chain of the 1-N-acyl-5-epi- intermediate possesses a chiral center, one can use each stereoisomer separately or a mixture thereof, and there will be obtained the corresponding diastereoisomers of a mixture thereof, respectively.

The 1-N-acyl-5-epi-4,6-di-O-(aminoglycosyl)-1,3-diaminocyclitol intermediates of this process, i.e. the 1-N-(OCK')-5-epi-4,6-di-O-(aminoglycosyl)-1,3-diaminocyclitols wherein K' is as hereinabove defined (e.g. 1-N-acetyl-5-episisomicin) are prepared by treating the corresponding 1-N-unsubstituted-5-epi-4,6-di-O-(aminoglycosyl)-1,3-diaminocyclitol of formulae I, II, III and IV which may have amino-protecting groups at any position other than at position 1, with an acid of the formula

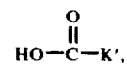

K' being hydrogen or an alkyl substituent as defined for K', and wherein any amino or hydroxy group present may be protected, in the presence of a carbodiimide such as dicyclohexylcarbodiimide, or with a reactive derivative of above said acid, and, if required, removing all protecting groups present in the molecule, the last process step being followed by isolating the derivative as such or as a pharmaceutically acceptable acid addition salt.

Amino protecting groups useful in the above process must be removeable under conditions which will not affect the 1-N-acyl group of the 1-N-acyl-5-epi-4,6-di-O-(aminoglycosyl)-2-deoxystreptamine, preferred protecting groups being trifluoroacetyl, t-butoxycarbonyl and benzyloxycarbonyl.

The 5-epi-4,6-di-O-(aminoglycosyl)-1,3-diaminocyclitol starting compounds of this process may have free amino groups or protected amino groups. If amino groups are protected in the 5-epi-4,6-di-O-(aminoglycosyl)-1,3-diaminocyclitols 5-epigentamicin B, 5- epigentamicin $C_{1a}$, 5-epi-Antibiotic JI-20A, 5-epi-Antibiotic 66-40B, 5-epi-Antibiotic 66-40D, 5-episisomicin, it is usually the 6'-amino group being protected. 5-Epigentamicin $C_1$ may be protected at positions 2' and 3. The 5-epi-4,6-di-O-(aminoglycosyl)-1,3-diaminocyclitol starting compounds may be used as a free nitrogen base (with or without N-protecting groups) or, as a compound wherein 1 to $n$ amino groups of the 5-epi-4,6-di-O-(aminoglycosyl)-1,3-diaminocyclitol are neutralized by formation of an acid addition salt whereby n is the number of amino groups in the molecule. The acid addition salt may also contain N-protecting groups. In a preferred method of the acylating process, $(n-1)$ amino groups are neutralized by formation of an acid addition salt. For example, one equivalent of 5-epigentamicin $C_1$ having five amino groups ($n=5$) requires five equivalents of acid to form the "per" acid addition salt. In the preferred method, as acid addition salt of 5-epigentamicin $C_1$ is used having $(n-1)$, i.e. four, amino groups which are protonated. The term "acid addition salt" embraces such salts as may be formed between the basic antibiotic and an acid without regard to whether the acid may be termed inorganic or organic. Exemplary of acids embraced by the term are sulfuric, hydrochloric, phosphoric, nitric, trifluoroacetic or the like.

If it is desired to use as a starting material an acid addition salt, wherein $(n-1)$ amino groups are protonated, this compound is advantageously produced in situ thereby reacting a "per" acid addition salt with an equivalent of strong base, e.g. triethylamine.

In general, the use of reactive derivatives of the acid

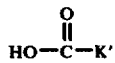

as acylating agents is preferred. Reactive derivatives of the acid comprise esters, azides, imidazole derivatives or anhydrides. In those instances wherein K' is unsubstituted, one of the preferred reactive derivatives is the anhydride of the requisite acid. In other instances it may be preferably to use the N-hydroxy-succinimidyl ester of the acid.

When carrying out the process whereby a reactive derivative of an acid containing an amino function is used, it is preferable to protect the amino function prior to carrying out the process and then removing the N-protecting group in the compound thereby formed. It may also be advantageous to protect a hydroxy group present in the acylating agent, however, it is not generally necessary.

1-N-acyl-5-epi-4,6-di-O-(aminoglycosyl)-2-deoxystreptamines, i.e. the 1-N-COK' derivatives of formulae I, II, III and IV, K' being as hereinabove defined, in addition to being intermediates in the preparation of 1-N-alkyl derivatives of formulae I-IV, are also valuable in that they exhibit broad spectrum antibacterial activity per se, the 1-N-acetyl derivatives being particularly useful compounds. Thus, the pharmaceutically acceptable acid addition salts of the 1-N-acylated compound, are also included within my invention.

The processes described hereinabove are illustrated in detail hereinbelow in the Preparations and Examples but should not be construed as limiting the scope of my invention, obvious equivalents of which will be apparent to those skilled in the art and are considered as within the scope of this invention.

PREPARATION 1

GENTAMICIN $C_{2a}$

A. Separation of Gentamicin $C_{2a}$ from Co-produced Antibiotics

Dissolve 96 gms. of gentamicin base (prepared from the sulfate salt obtained by the procedure of Example 4 of U.S. Pat. No. 3,091,572) in 400 ml. of the upper phase which results when methanol, chloroform and 17% ammonium hydroxide are mixed in the volume ratio of 1:2:1. Add one tenth of the solution to each of the first ten tubes in a 500 × 80 ml. tube counter current extractor. Fill all of the tubes including the first ten to capacity with the lower phase of the abovedescribed solvent mixture. Set the solvent reservoir to deliver 40 ml. of upper phase to tube one (1) for each transfer. Set the apparatus for 500 transfers. When the transfers are complete, sample every eighth tube for chromatography (in duplicate) on Schleicher and Schuell Paper No. 589 using the lower phase of the above-described solvent mixture. Permit the chromatograms to develop for about 16 hours, then dry the papers. Place one paper on an agar plate seeded with *Staphylococcus aureus* (A.T.C.C. 6538P), spray the duplicate with the conventional ninhydrin solution and heat to develop. Incubate the agar plate at 37° C overnight and combine the solution from tubes containing the material that migrates like gentamicin $C_1$ (i.e. tubes 290–360).

Replace tubes 290–360 with fresh tubes containing 40 ml. of upper phase and 40 ml. of lower phase. Reset the apparatus for an additional 2800 transfers and repeat the chromatographic procedure performed above. Combine tubes 1–16 and concentrate in vacuo to obtain 1.3 gms. of gentamicin $C_{2a}$ having the following properties:

a. a molecular weight of 463 as determined by mass spectrometry which is consistent with an empirical formula of $C_{20}H_{41}N_5O_7$;

b. a proton magnetic resonance (pmr) spectrum as follows: pmr (ppm) ($D_2O$): δ0.99 (3H, d, J=6.5Hz, CH—C$H_3$); 1.17 (3H, s, C—C$H_3$); 2.47 (3H, s, N—C$H_3$); 2.51 (1H, d, J=10.5Hz, H-3''); 3.75 (1H, q, J=10.5, 4Hz, H-2''); 4.00 (1H, d, J=12Hz, H-5'' eq); 5.04 (1H, d, J=4Hz, H-1''); 5.13 (1H, d, J=3.5Hz, H-1').

Irradiation of the secondary methyl group at δ 0.99 ppm reveals H-6' as a doublet (J=6.5Hz) at δ 2.81 ppm.

B. Biological Activity

Gentamicin $C_{2a}$ exhibits substantially the same antibacterial spectrum in vitro as do gentamicin $C_1$, $C_{1a}$ and $C_2$. It exhibits (as the free base) about 74% of the activity of the gentamicin C complex. Thus, the antibiotic is useful for substantially the same antibacterial indications and in the same manner as disclosed in U.S. Pat. No. 3,091,572. For example, it is useful in wash solutions, for sanitary purposes, as in the washing of hands and the cleaning of equipment in contaminated rooms.

In Table 1, set forth below is shown the in vitro minimal inhibitory concentration (MIC) of gentamicin $C_{2a}$ against representative gram-positive and gram-negative bacteria. The results are derived using the standard tube dilution method in Mueller-Hinton broth.

TABLE 1

| Organism | | MIC (mcg/ml) |
|---|---|---|
| Escherichia coli | ATCC 10536 | 0.3 |
| | LA 290/R55 | 17.5* |
| | JR66 | 7.5* |
| Pseudomonas acruginosa | 762 | 0.8 |
| | 3223 | 0.3 |
| | 20 | 3.0 |
| | St 138 | >25* |
| | Travers | >25* |
| Klebsiella pneumoniae | 17 | 0.8 |
| | 3694 | 17.5* |
| Salmonella typhi. B. | | 0.3 |
| Staphylococcus aureus | 6538P | 0.3 |
| | Ziegler | 0.3 |
| | 59N | 0.3 |
| Streptococcus pyogenes C | | 7.5 |
| Bacillus subtilis 663 | | 0.1 |
| *Gentamicin resistant | | |

The acute intravenous $LD_{50}$ of gentamicin $C_{2a}$ is 110 mg/kg when determined in male CF-1 (Carworth Farms) mice weighing 20 grams each.

PREPARATION 2

GENTAMICIN $C_{2b}$

A. Separation of Gentamicin $C_{2b}$ from Co-produced Antibiotics

Separate the major gentamicin C components ($C_1$, $C_2$ and $C_{1a}$) as described in U.S. Pat. No. 3,651,042, Example 2, and combine those fractions containing predominantly overlaps of gentamicins $C_1$ and $C_2$ free base (500 g. of gentamicin C mixture gives 53.4 g. of overlaps). Apply 1.5 g. of this gentamicin $C_1$ and $C_2$ mixture of a column containing 50 g. of silica gel made up in a solvent system comprising chloroform:methanol:15% ammonium hydroxide (1:2:1). Elute the column with the same solvent system and monitor the eluted fractions by thin layer chromatography on silica gel plates using the solvent system chloroform:methanol:22% ammonium hydroxide (1:2:1) as developer. Combine those fractions containing a mixture of gentamicins $C_1$ and $C_2$ together with gentamicin $C_{2b}$ (Fractions 39–57 (410 mg.)). Rechromatograph fractions 39-57 over silica gel using a chloroform:methanol:7% ammonium hydroxide (1:2:1) solvent system and combine those fractions (98–130) containing pure gentamicin $C_{2b}$ as determined by thin layer chromatography (yield 45 mg.) having the following constants $[\alpha]_D^{26}$ + 165° (C=0.3%, $H_2O$); Mass spectrum: m/e 463 (M+1)$^+$, 446, 445, 433, 350, 332, 322, 304, 333, 305, 287, 191, 173, 163, 145, 160, 142; 118, 143; pmr (ppm) ($D_2O$): δ 1.25 (3H, s, C—C$\underline{H}_3$); 2.40 (3H, s, N—C$\underline{H}_3$); 2.55 (3H, s, N—C$\underline{H}_3$); 5.12 (1H, d, J=4Hz, H-1″); 5.22 (1H, d, J=3Hz, H-1′).

Pure gentamicin $C_{2b}$ can be differentiated from gentamicin $C_1$ and $C_2$ by its mobility on thin layer chromatography using silica gel plates and a chloroform:methanol:22% ammonium hydroxide (1:2:1) solvent system as developer. The approximate Rf values in this system are as follows:

| | |
|---|---|
| Gentamicin $C_1$ | 0.47 |
| Gentamicin $C_2$ | 0.47 |
| Gentamicin $C_{2b}$ | 0.35 |

B. Biological Activity

Gentamicin $C_{2b}$ exhibits substantially the same antibacterial spectrum in vitro as do gentamicin $C_1$, $C_{1a}$ and $C_2$. Thus, the antibiotic is useful for substantially the same antibacterial indications and in the same manner as disclosed in U.S. Pat. No. 3,091,572.

In Table 2, set forth below is shown the in vitro minimal inhibitory concentration (MIC) of gentamicin $C_{2b}$ against representative gram-positive and gram-negative bacteria. The results are derived using the standard tube dilution method in Mueller-Hinton broth.

TABLE 2

| Organism | | MIC (mcg/ml) |
|---|---|---|
| Escherichia coli | ATCC 10536 | 0.075 |
| | LA 290/R55 | >25.0* |
| | JR66 | 7.5* |
| Pseudomonas aeruginosa | 762 | 0.3 |
| | 3223 | 0.075 |
| | 20 | 0.3 |
| | St 138 | 17.5* |
| | Travers | >25* |
| Klebsiella pneumoniae | 17 | 0.075 |
| | 3694 | 17.5* |
| Salmonella typhi. B. | | 0.3 |
| Staphylococcus aureus | wood | 0.075 |
| | Ziegler | 0.075 |
| | 59N | 0.075 |
| Streptococcus pyogenes | C | 3.0 |
| Bacillus subtilis 663 | | <0.05 |
| *Gentamicin resistant | | |

EXAMPLE I

PER-N-BENZYLOXYCARBONYLAMINOGLYCOSIDES

A. 1,3.2′, 6′,3″-Penta-N-benzyloxycarbonylgentamicin $C_{1a}$

Dissolve 40 gms. of gentamicin $C_{1a}$ in 200 ml. of methanol and 20 ml. of saturated sodium bicarbonate and cool the solution to 0° C. While stirring the solution, add dropwise over a period of 2 hours, 88 ml of carbobenzyloxy chloride keeping the reaction temperature between 0° C to 5° C. Stir the mixture overnight while allowing the reaction temperature to come to room temperature. Add 500 ml of chloroform to the reaction mixture which will then separate into 2 layers. Wash the organic phase with 4 × 100 ml of water and dry over 100 gms of sodium sulfate. Evaporate the organic phase under vacuum at a temperature of less than 40° C. Dissolve the resultant crude protect in 100 ml chloroform and add dropwise to 250 ml of 75% hexane/ether. Filter the resultant precipitate and wash with 100 ml hexane and air dry to obtain 87 grms (87%) of 1,3,2′, 6′,3″-Penta-N-benzyloxycarbonylgentamicin $C_{1a}$ melting point = 185°–190° C, $[\alpha]_D^{26}$ + 71.2 ($CH_3OH$), Infrared (IR) (KCl): 3300, 3500 cm$^{-1}$, PMR ($CDCl_3$): δ 1.2 (C—Me), 3.0 (N—Me), 7.25 (aromatic N)

B. In a similar manner subject to the process described in Example IA equivalent quantities of the following antibiotics:

1. gentamicin $C_1$
2. gentamicin $C_2$
3. gentamicin $C_{2a}$
4. gentamicin $C_{2b}$
5. Antibiotic G-52
6. verdamicin
7. Antibiotic 66-40D Isolate the resultant products in the manner described in Example IA to obtain, respectively:
1. 1,3,2',6',3''-Penta-N-benzyloxycarbonylgentamicin $C_1$,
2. 1,3,2',6',3''-Penta-N-benzyloxycarbonylgentamicin $C_2$,
3. 1,3,2',6',3''-Penta-N-benzyloxycarbonylgentamicin $C_{2a}$,
4. 1,3,2',6',3''-Penta-N-benzyloxycarbonylgentamicin $C_{2b}$,
5. 1,3,2',6',3''-Penta-N-benzyloxycarbonyl-Antibiotic G-52,
6. 1,3,2',6',3''-Penta-N-benzyloxycarbonylverdamicin, and
7. 1,3,2',6',3''-Penta-N-benzyloxycarbonyl-Antibiotic 66-40D.

C. 1,3,2',6',3''-Penta-N-benzyloxycarbonylsisomicin

Dissolve 25 gms. of sisomicin and 13 gms. of sodium carbonate in 625 ml. of water. While stirring the solution add 100 ml. of carbobenzyloxy chloride at 25° C. Stir the mixture for 16 hours and then filter off the solid, washing thoroughly with water. Dry the solid in vacuo and then wash with hexane and air dry to obtain 62 gms. of 1,3,2',6',3''-penta-N-benzyloxycarbonylsisomicin. Melting point = 165°–173° C; $[\alpha]_D^{26}$ + 96.2 ($CH_3OH$), Infrared (IR) = $\nu$max ($CHCl_3$), 3600, 1720, 1515, 1215, 1050, 695 cm$^{-1}$; PMR $\delta(CDCl_3)$ 1.03 (3H, broad singlet, 4''-C-$CH_3$), 3.02 (3H, broad singlet, 3''-N $CH_3$), 5.02 (10H, broad singlet-$CH_2C_6H_5$), 3.28, 3.30 ppm. (25 H, broad singlets, —$CH_2C_6H_5$).

D. In a manner similar to that described in Example 1A, treat each of the following aminoglycosides with carbobenzyloxy chloride in methanol: tobramycin, 3'4'-dideoxkanamycin B, gentamicin B, gentamicin $B_1$, gentamicin $X_2$, Antibiotic G-418, gentamicin A, Antibiotic 66-40B, Antibiotic JI-20A, Antibiotic JI-20B kanamycin A and kanamycin B. Isolate and purify each of the resultant products in a manner similar to that described in Example 1A to obtain, respectively,
1. 1,3,2',6',3''-penta-N-benzyloxycarbonyltobramycin,
2. 1,3,2',6',3''-penta-N-benzyloxycarbonyl-3',4'-dideoxykanamycin B,
3. 1,3,6',3''-tetra-N-benzyloxycarbonylgentamicin B,
4. 1,3,6',3''-tetra-N-benzyloxycarbonylgentamicin $B_1$,
5. 1,3,2',3''-tetra-N-benzyloxycarbonylgentamicin $X_2$,
5. 1,3,2',3''-tetra-N-benzyloxycarbonyl-Antibiotic G-418,
7. 1,3,2',3''-tetra-N-benzyloxycarbonylgentamicin A,
8. 1,3,2',6',3''-penta-N-benzyloxycarbonyl-Antibiotic 66-40B,
9. 1,3,2',6',3''-penta-N-benzyloxycarbonyl-Antibiotic JI-20A,
10. 1,3,2',6',3''-penta-N-benzyloxycarbonyl-Antibiotic JI-20B,
11. 1,3,6',3''-tetra-N-benzyloxycarbonylkanamycin A, and
12. 1,3,2',6',3''-penta-N-benzyloxycarbonylkanamycin B.

EXAMPLE II

PER-N-BENZYLOXYCARBONYL-3'',4''-N,O,-CARBONYLAMINOGLYCOSIDES

A.

1,3,2',6'-tetra-N-benzyloxycarbonyl-3'',4''-N,O-carbonylgentamicin $C_{1a}$

To a stirred mixture of 60 mg sodium hydride in 5 ml of dry dimethylformamide add a solution of 2 gms of the product of Example IA in 50 ml of dry dimethylformamide over ½ hour at room temperature under nitrogen. Stir the reaction mixture for 2 hours and then filter off insolubles. To the filtrate add 100 ml of chloroform and wash the organic phase with 3 × 50 ml. of water. Dry the organic phase over 25 gm. sodium sulfate and then evaporate under reduced pressure. Dissolve the resultant residue in 15 ml. of chloroform and add dropwise to 75% hexane:ether (15 ml.). Filter the precipitate and wash with 25 ml. hexane to obtain 1.82 gm. (> 95%) of 1,3,2',6'-tetra-N-benzyloxycarbonyl-3'',4''-N,O-carbonylgentamicin $C_{1a}$. melting point = 215° C (dec.) $[\alpha]_D^{26}$ + 63.4. Infrared (IR)-(KCl) = 3300, 3500, 1680, 1545, PMR ($CDCl_3$) $\delta$ 1.28 (C-Me), 2.58 (N—Me), 7.25 (aromatic H).

B. In a similar manner, subject to the process described in Example IIA equivalent quantities of the products of Example IB and isolate each of the resultant products to obtain, respectively,
1. 1,3,2',6'-tetra-N-benzyloxycarbonyl-3'',4''-N,O-carbonylgentamicin $C_1$,
2. 1,3,2',6'-tetra-N-benzyloxycarbonyl-3'',4''-N,O-carbonylgentamicin $C_2$,
3. 1,3,2',6'-tetra-N-benzyloxycarbonyl-3'',4''-N,O-carbonylgentamicin $C_{2a}$,
4. 1,3,2',6'-tetra-N-benzyloxycarbonyl-3'',4''-N,O-carbonylgentamicin $C_{2b}$,
5. 1,3,2',6'-tetra-N-benzyloxycarbonyl-3'',4''-N,O-carbonylAntibiotic G-52,
6. 1,3,2',6'-tetra-N-benzyloxycarbonyl-3'',4''-N,O-carbonylverdamicin, and
7. 1,3,2',6'-tetra-N-benzyloxycarbonyl-3'',4''-N,O-carbonylAntibiotic 66-40D.

C.

1,3,2',6'-Tetra-N-Benzyloxycarbonyl-3'',4''-N,O-Carbonylsisomicin

To a stirred solution of 5 gms. of the product of Example IC in 50 ml. of dimethylformamide add 250mg. of sodium hydride. Stir the reaction mixture under argon for 2 hours at room temperature. Filter and add 2 ml. glacial acetic acid to the filtrate. Concentrate the filtrate in vacuo and extract the residue with 200 ml. of chloroform (purified by passage through basis alumina). Wash the chloroform extracts with water and dry ever sodium sulfate and evaporate to obtain 3.5 gms. of 1,3,2',6'-tetra-N-benzyloxycarbonyl-3'',4''-N,O-carbonylsisomicin; melting point 210°–213° C; $[\alpha]_D^{26}$ + 68.8 (c 0.22) Infrared (IR) $\nu$max (nujol) 3550, 1760, 1580 cm$^{-1}$ PMR $\delta(CDCl_3)$ 1.34 (3H, singlet-4''-$CH_3$), 2.68 (3H, singlet-3''-N-$CH_3$), 5.04 (8H, broad singlet-$CH_2C_6H_5$).

D. In a manner similar to that described in Example IIA, treat each of the following benzyloxycarbonylaminoglycosides of Example ID with sodium hydride in dimethylformamide.
1. 1,3,6',3''-tetra-N-benzyloxycarbonylgentamicin B,
2. 1,3,6',3''-tetra-N-benzyloxycarbonylgentamicin $B_1$, 3. 1,3,2',3''-tetra-N-benzyloxycarbonylgentamicin $X_2$,
4. 1,3,2',3''-tetra-N-benzyloxycarbonyl-Antibiotic G-418,
5. 1,3,2',6',3''-penta-N-benzyloxycarbonyl-Antibiotic JI-20A,
6. 1,3,2',6',3''-penta-N-benzyloxycarbonyl-Antibiotic JI-20B.

Isolate and purify each of the resultant products in a manner similar to that described in Example IIA to obtain, respectively, 1. 1,3-di-N-benzyloxycarbonyl-6',4';3'',4''-di-N,O-carbonylgentamicin B,
2. 1,3-di-N-benzyloxycarbonyl-6',4';3'',4''-di-N,O-carbonylgentamicin $B_1$,
3. 1,3,2'-tri-N-benzyloxycarbonyl-3'',4''-N,O-carbonylgentamicin $X_2$,
4. 1,3,2'-tri-N-benzyloxycarbonyl-3'',4''-N,O-carbonyl-Antibiotic G-418,
5. 1,3,2',6'-tetra-N-benzyloxycarbonyl-3'',4''-N,O-carbonylAntibiotic JI-20A,
6. 1,3,2',6'-tetra-N-benzyloxycarbonyl-3'',4''-N,O-carbonylAntibiotic JI-20B.

EXAMPLE III

PER-N-BENZYLOXYCARBONYL-2''-O-HYDROCARBONCARBONYL-3'',4''-N,O-CARBONYLAMINOGLYCOSIDES

A.

1,3,2',6'-tetra-N-benzyloxycarbonyl-2''-O-Benzoyl-3'',4''-N,O-carbonylgentamicin $C_{1a}$ To a stirred solution of 10 gm of 1,3,2',6'-tetra-N-benzyloxycarbonyl-3'',4''-N,O-carbonylgentamicin $C_{1a}$ in 50 ml of dry pyridine add dropwise over a period 10–15 minutes under an atmosphere of nitrogen, 2 ml benzoyl chloride. Stir the reaction mixture for ½ hour and then remove the pyridine via a rotary evaporator keeping the bath temperature at less than 30° C. Dissolve the residual pale yellow oil in 100 ml of chloroform. Wash this organic phase with 3 × 50 ml water and then dry over 25 gm sodium sulfate. Evaporate the chloroform under vacuum. Triturate the residual yellow foam with a small volume of ether to obtain 11.0 gms. (>95%) 1,3,2',6'-tetra-N-benzyloxycarbonyl-2''-O-benzoyl-3'',4''-N,O-carbonylgentamicin $C_{1a}$. Melting point = 120°–123° C $[\alpha]_D^{26}$ + 73.8.

B. In a similar manner, subject to the process described in Example IIIA, equivalent, quantities of the products of Example IIB and isolate the resultant products to obtain respectively:

1. 1,3,2',6'-tetra-N-benzyloxycarbonyl-2''-O-Benzoyl-3'',4''-N,O-carbonylgentamicin $C_1$,
2. 1,3,2',6'-tetra-N-benzyloxycarbonyl-2''-O-Benzoyl-3'',4''-N,O-carbonylgentamicin $C_2$,
3. 1,3,2',6'-tetra-N-benzyloxycarbonyl-2''-O-Benzoyl-3'',4''-N,O-carbonylgentamicin $C_{2a}$,
4. 1,3,2',6'-tetra-N-benzyloxycarbonyl-2''-O-Benzoyl-3'',4''-N,O-carbonylgentamicin $C_{2b}$,
5. 1,3,2',6'-tetra-N-benzyloxycarbonyl-2''-O-Benzoyl-3'',4''-N,O-carbonyl-Antibiotic G-52,
6. 1,3,2',6'-tetra-N-benzyloxycarbonyl-2''-O-Benzoyl-3'',4''-N,O-carbonylverdamicin, and
7. 1,3,2',6'-tetra-N-benzyloxycarbonyl-2''-O-Benzoyl-3'',4''-N,O-carbonyl-Antibiotic 66-40D.

C.

1,3,2',6'-Tetra-N-Benzyloxycarbonyl-2''-O-Benzoyl-3'',4''-N,O-Carbonylsisomicin

To a stirred solution of 3 gms. of the product of Example IIC in 20 ml. of dry pyridine at 25° C under an atmosphere of argon add 1.7 ml. of benzoylchloride over a 10 minute period. Stir at room temperature until all the starting material reacts (monitor by thin layer chromatography). Evaporate the mixture at room temperature under high vacuum; extract the solid residue with 100 ml. chloroform (previously passed through basic alumina). Wash the chloroform extracts with 5% aqueous sodium bicarbonate, water and then dry over sodium sulfate. Evaporate the solvent to obtain 2.8 gms. 1,3'',2',6'-tetra-N-benzyloxycarbonyl-2''-O-benzoyl-3'',4''-N,O-carbonylsisomicin; melting point 157°–160° C, $[\alpha]_D^{26}$ + 86, (c 0.2) Infrared (IR) $\nu$max (nujol) 3325, 1780, 1680, 1560 cm$^{-1}$ PMR $\delta$ (CDCl$_3$) 1.35 (4''-C-CH$_3$), 2.74 (3''-N-CH$_3$), 5.03 (CH$_2$-C$_6$H$_5$).

D.

1,3,2',6'-tetra-N-benzyloxycarbonyl-2''-O-acetyl-3'',4''-N,O-carbonylgentamicin $C_{1a}$

1.

1,3,2',6',3''-penta-N-benzyloxycarbonyl-2''-O-acetylgentamicin $C_{1a}$

To a stirred solution of 10 gms. of 1,3,2',6',3''-penta-N-benzyloxycarbonylgentamicin $C_{1a}$ in 50 ml. of dry pyridine, add dropwise over a period of 10–15 minutes under an atmosphere of nitrogen, 1.4 ml. of acetic anhydride. Stir the reaction mixtre for ½ hour and then remove the pyridine via a rotary evaporator, keep bath temperature at less than 30° C. Dissolve the resultant residue in 100 ml. of acid-free chloroform. Wash this organic solution with 3 × 50 ml. water, then dry over sodium sulfate and evaporate in vacuo. Purify the resultant residue by trituration with small volumes of ether to obtain 1,3,2',6',3''-penta-N-benzyloxycarbonyl-2''-O-acetylgentamicin $C_{1a}$.

2.

1,3,2',6'-tetra-N-benzyloxycarbonyl-2''-O-acetyl-3'',4''-N,O-carbonylgentamicin $C_{1a}$ In a manner similar to that described in Example IIA treat 1,3,2',6',3''-penta-N-benzyloxycarbonyl-2''-O-acetylgentamicin $C_{1a}$ in dry dimethylformamide with sodium hydride. Isolate and purify the resultant product in a manner similar to that described in Example IIA to obtain 1,3,2',6'-tetra-N-benzyloxycarbonyl-2''-O-acetyl-3'',4''-N,O-carbonylgentamicin $C_{1a}$.

E.

1,3,2',6'-tetra-N-benzyloxycarbonyl-2''-O-acetylaminoglycosides

1. In a manner similar to that described in Example IIID(1) treat each of the products of Example IB with acetic anhydride in pyridine. Isolate and purify each of the resultant products to obtain, respectively, 1. 1,3,2',6',3''-penta-N-benzyloxycarbonyl-2''-O-acetylgentamicin $C_1$,
2. 1,3,2',6',3''-penta-N-benzyloxycarbonyl-2''-O-acetylgentamicin $C_2$,
3. 1,3,2',6',3''-penta-N-benzyloxycarbonyl-2''-O-acetylgentamicin $C_{2a}$,
4. 1,3,2',6',3''-penta-N-benzyloxycarbonyl-2''-O-acetylgentamicin $C_{2b}$, 5. 1,3,2',6',3''-penta-N-benzyloxycarbonyl-2''-O-acetyl-Antibiotic G-52,
6. 1,3,2',6',3''-penta-N-benzyloxycarbonyl-2''-O-acetylverdamicin,
7. 1,3,2',6',3''-penta-N-benzyloxycarbonyl-2''-O-acetyl-Antibiotic 66-40D.

2. In a manner similar to that described in Example IIA treat each of the products obtained in Example IIIE(1) with sodium hydride in dry dimethylformamide. Isolate and purify each of the resultant products in a manner similar to that described in Example IIA to obtain, respectively, 1. 1,3,2',6'-tetra-N-benzyloxycarbonyl-2''-O-acetyl-3'',4''-N,O-carbonylgentamicin $C_1$,
2. 1,3,2',6'-tetra-N-benzyloxycarbonyl-2''-O-acetyl-3'',4''-N,O-carbonylgentamicin $C_2$,
3. 1,3,2',6'-tetra-N-benzyloxycarbonyl-2''-O-acetyl-3'',4''-N,O-carbonylgentamicin $C_{2a}$,
4. 1,3,2',6'-tetra-N-benzyloxycarbonyl-2''-O-acetyl-3'',4''-N,O-carbonylgentamicin $C_{2b}$,
5. 1,3,2',6'-tetra-N-benzyloxycarbonyl-2''-O-acetyl-3'',4''-N,O-carbonyl-Antibiotic G-52,
6. 1,3,2',6'-tetra-N-benzyloxycarbonyl-2''-O-acetyl-3'',4''-N,O-carbonylverdamicin,
7. 1,3,2',6'-tetra-N-benzyloxycarbonyl-2''-O-acetyl-3'',4''-N,O-carbonyl-Antibiotic 66-40D.

F.
1,3,2',6'-Tetra-N-Benzyloxycarbonyl-2''-O-Acetyl-3'',4''-N,O-Carbonylsisomicin 1. In a manner similar to that described in Example IIID(1) treat 1,3,2',6',3''-penta-N-benzyloxycarbonylsisomicin with acetic anhydride in pyridine. Isolate and purify the resultant product in a manner similar to that described in Example IIID(1) to obtain 1,3,2',6'-tetra-N-benzyloxycarbonyl-2''-O-acetylsisomicin.

2. In a manner similar to that described in Example IIC treat 1,3,2',6',3''-penta-N-benzyloxycarbonyl-2''-O-acetylsisomicin with sodium hydride in dimethylformamide. Isolate and purify the product in a manner similar to that described in Example IIC to obtain 1,3,2',6'-tetra-N-benzyloxycarbonyl-2''-O-acetyl-3'',4''-N,O-carbonylsisomicin.

EXAMPLE IV

PER-N-BENZYLOXYCARBONYL-2''-O-HYDROCARBONCARBONYL-5-O-HYDROCARBONSULFONYL-3'',4''-N,O-CARBONYLAMINOGLYCOSIDES

A.
1,3,2',6'-Tetra-N-Benzyloxycarbonyl-5-O-Methanesulfonyl-2''-O-Benzoyl-3'',4''-N,O-Carbonylgentamicin $C_{1a}$ Cool a solution of 1 gm. of 1,3,2',6'-tetra-N-benzyloxycarbonyl-2''-O-benzoyl-3'',4''-N,O-carbonylgentamicin $C_{1a}$ in 5 ml. of triethylamine and 15 ml. tetrahydrofuran to below 0° C. Stir the solution and to it add, over a period of 15 minutes, a solution of 1 ml. of methanesulfonyl chloride in 5 ml. of tetrahydrofuran. Stir the reaction mixture for 2 hours at 0° C. Pour the reaction mixture into 25 ml. of water and 25 ml. of chloroform. Wash the organic phase with 2 × 15 ml of water and then dry the organic phase over sodium sulfate. Evaporate the chloroform and triturate the resulting yellow foam with small amounts of ether to obtain 1.2 gm (>95%) of the 1,3,2',6'-tetra-N-benzyloxycarbonyl-5-O-methanesulfonyl-2''-O-benzoyl-3'',4''-N,O-carbonylgentamicin $C_{1a}$. Melting point = 130° C $[\alpha]_D^{26} + 53.4$ (CHCl$_3$) PMR (CDCl$_3$) δ1.35 (C—Me), 2.74 (N—Me), 2.99 (OSO$_2$CH$_3$), 7.28 (4×Cbz and benzoyl).

In similar manner treat 1,3,2',6'-tetra-N-benzyloxycarbonyl-2''-O-acetyl-3'',4''-N,O-carbonylgentamicin $C_{1a}$ in triethylamine and tetrahydrofuran with methanesulfonylchloride to obtain 1,3,2',6'-tetra-N-benzyloxycarbonyl-5-O-methanesulfonyl-2''-O-acetyl-3'',4''-N,O-carbonylgentamicin $C_{1a}$.

B. In a similar manner, subject to the process described in Example IVA equivalent quantities of the products of Example IIIB and isolate the resultant products to obtain, respectively, 1. 1,3,2',6'-tetra-N-benzyloxycarbonyl-5-O-methanesulfonyl-2''-O-benzoyl-3'',4''-N,O-carbonylgentamicin $C_1$,
2. 1,3,2',6'-tetra-N-benzyloxycarbonyl-5-O-methanesulfonyl-2''-O-benzoyl-3'',4''-N,O-carbonylgentamicin $C_2$,
3. 1,3,2',6'-tetra-N-benzyloxycarbonyl-5-O-methanesulfonyl-2''-O-benzoyl-3'',4''-N,O-carbonylgentamicin $C_{2a}$,
4. 1,3,2',6'-tetra-N-benzyloxycarbonyl-5-O-methanesulfonyl-2''-O-benzoyl-3'',4''-N,O-carbonylgentamicin $C_{2b}$,
5. 1,3,2',6'-tetra-N-benzyloxycarbonyl-5-O-methanesulfonyl-2''-O-benzoyl-3'',4''-N,O-carbonyl-Antibiotic G-52,
6. 1,3,2',6'-tetra-N-benzyloxycarbonyl-5-O-methanesulfonyl-2''-O-benzoyl-3'',4''-N,O-carbonylverdamicin, and
7. 1,3,2',6'-tetra-N-benzyloxycarbonyl-5-O-methanesulfonyl-2''-O-benzoyl-3'',4''-N,O-carbonyl-Antibiotic 66-40D.

C.
1,3,2',6'-Tetra-N-Benzyloxycarbonyl-5-O-Methanesulfonyl-2''-Q-Benzoyl-3'',4''-N,O-Carbonylsisomicin Dissolve 2.5 gms. of the product of Example IIIC in 15 ml. of dry pyridine. Cool the solution to 10° C and add 4 ml. of methanesulfonyl chloride over a period of 10 minutes, allow the reaction mixture to stand overnight, then concentrate the reaction mixture under vacuum at 25° C. Extract the residue with 150 ml. of acid-free chloroform. Wash the chloroform extracts with water and dry over sodium sulfate. Evaporate the chloroform to give 2.4 gm. of 1,3,2',6'-tetra-N-benzyloxycarbonyl-5-O-methanesulfonyl-2''-O-benzoyl-3'',4''-N,O-carbonylsisomicin; melting point 84°–88° C, $[\alpha]_D^{26}$ 21.3 (c 0.29) Infrared (IR) ν max (nujol) 3325, 1750, 1540 cm$^{-1}$; PMR δ (CDCl$_3$) 1.32 (4''-C-CH$_3$), 2.68 (3''-N-CH$_3$),

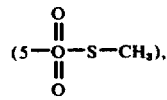

5.00 (—CH$_2$C$_6$H$_5$).

EXAMPLE V

PER-N-BENZYLOXYCARBONYL-O-YLIDENE AMINOGLYCOSIDES

A.

1,3,2',6',3''-Penta-N-benzyloxycarbonyl-4'',6''-O-Benzylidene-Tobramycin

To a solution of 5 gms. of 1,3,2',6',3''-penta-N-benzyloxycarbonyltobramycin in 25 ml. of anhydrous dimethylformamide add 1 ml. of benzaldehyde and 300 mg. of dry para-toluenesulfonic acid. Heat in a sealed flask at 110° C for four hours, cool the solution, then treat the cooled solution with 6 ml. of Amberlite IR-401S resin in the hydroxide form. Filter off the resin and evaporate the filtrate in vacuo to a residue comprising 1,3,2',6', 3''-penta-N-benzyloxycarbonyl-4'',-6''-O-benzylidenetobramycin.

B. In a manner similar to that described in above Example VA, treat each of the following per-N-benzyloxycarbonylamino glycosides with benzaldehyde in dimethylformamide in the presence of para-toluenesulfonic acid.

1. 1,3,2',6',3''-penta-N-benzyloxycarbonyl-3',4'-dideoxykanamycin B.
2. 1,3,2',6'-tetra-R-benzyloxycarbonyl-3'',4''-N,O-carbonyl-Antibiotic JI-2CA.
3. 1,3,2',6'-tetra-N-benzyloxycarbonyl-3'',4''-N,O-carbonyl-Antibiotic JI-20B,
4. 1,3,2',3''-tetra-N-benzyloxycarbonylgentamicin A,
5. 1,3,6',3''-tetra-N-benzyloxycarbonylkanamycin A,
6. 1,3,2',6',3''-penta-N-benzyloxycarbonylkanamycin B.

Isolate and purify each of the resultant products in a manner similar to that described in Example VA to obtain, respectively, 1. 1,3,2',6',3''-penta-N-benzyloxycarbonyl-4'',6''-O-benzylidene-3',4'-dideoxykanamycin B,
2. 1,3,2',6'-tetra-N-benzyloxycarbonyl-3',4'-O-benzylidene-3'',4''-N,O-carbonyl-Antibiotic JI-20A,
3. 1,3,2',6'-tetra-N-benzyloxycarbonyl-3',4'-O-benzylidene-3'',4''-N,O-carbonyl-Antibiotic JI-20B,
4. 1,3,2',3''-tetra-N-benzyloxycarbonyl-4',6'-O-benzylidene-gentamicin A,
5. 1,3,6',3''-tetra-N-benzyloxycarbonyl-2',3';4'',6''-di-O-benzylidenekanamycin A in admixture with 1,3,6',3''-tetra-N-benzyloxycarbonyl-3',4';4'',6''-di-O-benzylidenekanamycin A,
6. 1,3,2',6',3''-penta-N-benzyloxycarbonyl-3',4';4'λ',6''-di-O-benzylidenekanamycin B.

C.

1,3-Di-N-Benzyloxycarbonyl-2',3'-O-Cyclohexylidene-6',4';3'',4''-Di-N,O-Carbonylgentamicin B To a solution of 5 gms. of 1,3-di-N-benzyloxycarbonyl-6',4';3'',4''-di-N,O-carbonylgentamicin B in 25 ml. of anhydrous dimethylformamide add 5 ml. of 1,1-dimethoxycyclohexane and 300 mg. of dry para-toluenesulfonic acid. Heat in a sealed flask at 110° C for 4 hours. Cool the solution and then treat the cooled solution with 6 ml. of Amberlite IR-401S resin in the hydroxide form. Filter off the resin and evaporate the filtrate in vacuo to a residue comprising 1,3-di-N-benzyloxycarbonyl-2',3'-O-cyclohexylidene-6',4';3'',4''-di-N,O-carbonylgentamicin B.

D. In a manner similar to that described in Example VC treat each of the following per-N-benzyloxycarbonylaminoglycosides with 1,1-dimethoxycyclohexane and para-toluenesulfonic acid in dimethylformamide.

1. 1,3-di-N-benzyloxycarbonyl-6',4';3'',4''-di-N,O-Carbonylgentamicin $B_1$,
2. 1,3,2'-tri-N-benzyloxycarbonyl-3'',4''-N,O-carbonylgentamicin $X_2$,
3. 1,3,2'-tri-N-benzyloxycarbonyl-3'',4''-N,O-carbonyl-Antibiotic G-418, Isolate and purify each of the resultant products in a manner similar to that described in Example VC to obtain, respectively, 1. 1,3-di-N-benzyloxycarbonyl-2',3'-O-cyclohexylidene-6',4';3'', 4''-di-N,O-carbonylgentamicin $B_1$,
2. 1,3,2'-tri-N-benzyloxycarbonyl-4',6'-O-cyclohexylidene-3'',4''-N,O-carbonylgentamicin $X_2$,
3. 1,3,2',tri-N-benzyloxycarbonyl-4',6'-O-cyclohexylidene-3'',4''-N,O-carbonyl-Antibiotic G-418.

EXAMPLE VI

2''-O-BENZOYL-PER-N-BENZYLOXYCARBONYL-O-YLIDENE-AMINOGLYCOSIDES

In a manner similar to that described in Example IIIA, treat each of the following aminoglycosides with one equivalent of benzoylchloride in pyridine.

1. 1,3,2',6',3''-penta-N-benzyloxycarbonyl-4'',6''-O-benzylidene-3',4'-dideoxykanamycin B,
2. 1,3-di-N-benzyloxycarbonyl-2',3'-O-cyclohexylidene-6',4'; 3'',4''-di-N,O-carbonylgentamicin B,
3. 1,3-di-N-benzyloxycarbonyl-2',3'-O-cyclohexylidene-6',4';3'', 4''-di-N,O-carbonylgentamicin $B_1$,
4. 1,3,2',6'-tetra-N-benzyloxycarbonyl-3',4'-benzylidene-3'',4''-N,O-carbonyl-Antibiotic JI-20A,
5. 1,3,2',6'-tetra-N-benzyloxycarbonyl-3',4'-O-benzylidene-3'',4''-N,O-carbonyl-Antibiotic JI-20B,
6. 1,3,2',6',3''-penta-N-benzyloxycarbonyl-3',4';4'λ',6''-di-O-benzylidenekanamycin B.

Isolate and purify each of the resultant products in a manner similar to that described in Example IIIA to obtain, respectively, 1. 1,3,2',6',3''-penta-N-benzyloxycarbonyl-2''-O-benzoyl-4'',6''-O-benzylidene-3',4'-dideoxykanamycin B,
2. 1,3-di-N-benzyloxycarbonyl-2',3'-O-cyclohexylidene-6',4'; 3'',4''-di-N,O-carbonyl-2''-O-benzoylgentamicin B,
3. 1,3-di-N-benzyloxycarbonyl-2',3'-O-cyclohexylidene-6',4'; 3'',4''-di-N,O-carbonyl-2''-O-benzoylgentamicin $B_1$,
4. 1,3,2',6'-tetra-N-benzyloxycarbonyl-3',4'-O-benzylidene-2''-O-benzoyl-3'',4''-N,O-carbonyl-Antibiotic JI-20A,
5. 1,3,2',6'-tetra-N-benzyloxycarbonyl-3',4'-O-benzylidene-2''-O-benzoyl-3'',4''-N,O-carbonyl-Antibiotic JI-20B,
6. 1,3,2',6',3''-penta-N-benzyloxycarbonyl-3',4';4'λ',6''-di-O-benzylidene-2''-O-benzoylkanamycin B.

B. In a manner similar to that described in Example IIIA, treat each of the following aminoglycosides with two equivalents of benzoylchloride in pyridine.

1. 1,3,2',6',3''-penta-N-benzyloxycarbonyl-4'',6''-O-benzylidenetobramycin,
2. 1,3,2',6',3''-penta-N-benzyloxycarbonyl-Antibiotic 66-40B,
3. 1,3,2'-tri-N-benzyloxycarbonyl-4',6'-O-cyclohexylidene-3'',4''-N,O-carbonylgentamicin $X_2$, 4. 1,3,2'-tri-N-benzyloxycarbonyl-4',6'-O-cyclohexylidene-3'',4''-N,O-carbonyl-Antibiotic G-418, 5. 1,3,6',3''-tetra-N-benzyloxycarbonyl-2',3';4'',6''-di-O-benzylidenekanamycin A in admixture with 1,3,6',3''-tetra-N-benzyloxycarbonyl-3',4';4'',6''-di-O-benzylidenekanamycin A.

Isolate and purify each of the resultant products in a manner similar to that described in Example IIIA to obtain 1. 1,3,2',6',3''-penta-N-benzyloxycarbonyl-4',2''-di-O-benzoyl-4'',6''-O-benzylidenetobramycin, 2. 1,3,2',6',3''-penta-N-benzyloxycarbonyl-2'',4''-di-O-benzoyl-Antibiotic 66-40B, 3. 1,3,2'-tri-N-benzyloxycarbonyl-3',2''-di-O-benzoyl-4',6'-O-cyclohexylidene-3'',4''-N,O-carbonylgentamicin $X_2$, 4. 1,3,2'-tri-N-benzyloxycarbonyl-3'',2''-di-O-benzoyl-4',6'-O-cyclohexylidene-3'',4''-N,O-carbonyl-Antibiotic G-418, 5. 1,3,6',3''-tetra-N-benzyloxycarbonyl-2',3';4'',6''-di-O-benzylidene-4',2''-di-O-benzoylkanamycin A in admixture with 1,3,6',3''-tetra-N-benzyloxycarbonyl-2'',2''-di-O-benzoyl-3',4'; 4'',6''-di-O-benzylidenekanamycin A.

C. In a manner similar to that described in Example IIIA, treat 1,3,2',3''-tetra-N-benzyloxycarbonyl-4',6'-O-benzylidenegentamicin A with three equivalents of benzoyl chloride in pyridine. Isolate and purify the resultant product in a manner similar to that described to obtain 1,3,2',3''-tetra-N-benzyloxycarbonyl-3', 2'',4''-tri-O-benzoyl-4',6'-O-benzylidenegentamicin A.

D. In each of procedures VIA, VIB and VIC by substituting for benzoyl chloride an equivalent quantity of acetic anhydride there is obtained the corresponding O-acetyl ester, e.g. by treating 1,3,2',3''-tetra-N-benzyloxycarbonyl-4',6'-O-benzylidenegentamicin A with three equivalents of acetic anhydride in pyridine there is obtained 1,3,2',3''-tetra-N-benzyloxycarbonyl-3',2'λ',4''-tri-O-acetyl-4',6'-O-benzylidenegentamicin A.

EXAMPLE VII

5-O-METHANESULFONYL-2''-O-BENZOYL-O-YLIDENE-N-BENZYLOXYCARBONYLAMINO-GLYCOSIDES

In a manner similar to that described in Example IVA, treat each of the compounds prepared in Example VIA, B and C with methanesulfonylchloride in triethylamine and tetrahydrofuran. Isolate and purify each of the resultant products in a manner similar to that described in Example IVA to obtain 1. 1,3,2',6',3''-penta-N-benzyloxycarbonyl-5-O-methanesulfonyl-2''-O-benzoyl-4'',6''-O-benzylidene-3',4'-dideoxykanamycin B, 2. 1,3-di-N-benzyloxycarbonyl-5-O-methanesulfonyl-2',3'-O-cyclohexylidene-6',4';3'',4''-di-N,O-carbonyl-2''-O-benzoylgentamicin B, 3. 1,3-di-N-benzyloxycarbonyl-5-O-methanesulfonyl-2',3'-O-cyclohexylidene-6',4';3'',4''-di-N,O-carbonyl-2''-O-benzoylgentamicin $B_1$, 4. 1,3,2',6'-tetra-N-benzyloxycarbonyl-5-O-methanesulfonyl-3',4'-O-benzylidene-2''-O-benzoyl-3'',4''-N,O-carbonyl-Antibiotic JI-20A, 5. 1,3,2',6'-tetra-N-benzyloxycarbonyl-5-O-methanesulfonyl-3',4'-O-benzylidene-2''-O-benzoyl-3'',4''-N,O-carbonyl-Antibiotic JI-20B, 6. 1,3,2',6',3''-penta-N-benzyloxycarbonyl-5-O-methanesulfonyl-3',4';4'',6''-di-O-benzylidene-2''-O-benzoylkanamycin B, 7. 1,3,2',6',3''-penta-N-benzyloxycarbonyl-5-O-methanesulfonyl-4',2''-di-O-benzoyl-4'',6''-O-benzylidenetobramycin, 8. 1,3,2',6',3''-penta-N-benzyloxycarbonyl-5-O-methanesulfonyl-2'',4''-di-O-benzoyl-Antibiotic 66-40B, 9. 1,3,2'-tri-N-benzyloxycarbonyl-5-O-methanesulfonyl-3',2''-di-O-benzoyl-4',6'-O-cyclohexylidene-3'',4''-N,O-carbonylgentamicin $X_2$, 10. 1,3,2'-tri-N-benzyloxycarbonyl-5-O-methanesulfonyl-3',2''-di-O-benzoyl-4',6'-O-cyclohexylidene-3'',4''-N,O-carbonyl-Antibiotic C-418, 11. 1,3,6',3''-tetra-N-benzyloxycarbonyl-5-O-methanesulfonyl-2',3'; 4'',6''-di-O-benzylidene-4',2''-di-O-benzoylkanamycin A in admixture with 1,3,6',3''-tetra-N-benzyloxycarbonyl-5-O-methanesulfonyl-2',2''-di-O-benzoyl-3',4';4'',6''-di-O-benzylidenekanamycin A.

12. 1,3,2',3''-tetra-N-benzyloxycarbonyl-5-O-methanesulfonyl-3', 2'',4''-tri-O-benzoyl-4',6'-O-benzylidenegentamicin A.

1-N-ALKYL INTERMEDIATES

In the procedures described in Examples I – VII, by utilizing as starting compounds the 1-N-alkyl derivatives of the starting antibacterial aminoglycosides named therein, there is obtained the corresponding 1-N-alkyl-per-N-protected-per-O-protected-5-O-hydrocarbonsulfonyl aminoglycoside intermediates. Of particular interest are 1-N-alkyl derivatives having up to 4 atoms, including alkyl substituents such as ethyl, n-propyl, n-butyl-, δ-aminobutyl, γ-aminopropyl-, β-hydroxyethyl, S-δ-amino-β-hydroxybutyl and the like. In general, this invention includes 5-epi-4,6-di-O-(aminoglycosyl)-2-deoxystreptamines and intermediates useful in their preparation which have 1-N-alkyl substituents having up to 8 carbon atoms also including alkyl derivatives such as β-methylpropyl, n-octyl, β-propenyl, β-ethyl-β-hexenyl, benzylphenylethyl, cyclohexylmethyl, β-hydroxy-δ-pentenyl-, ω-hydroxyoctyl, β-methyl-β-hydroxy-γ-aminopropyl, S-γ-amino-β-hydroxypropyl, and the like.

PREPARATION OF 5-EPI-4,6-DI-O-(AMINOGLYCOSYL)-2-DEOXYSTREPTAMINES VIA REACTION OF THE 5-O-HYDROCARBONSULFONYL DERIVATIVE WITH DIMETHYLFORMAMIDE

EXAMPLE VIII

5-EPIGENTAMICIN $C_1$

A. Add 2 gms. of 1,3,2',6'-tetra-N-benzyloxycarbonyl-5-O-methanesulfonyl-2''-O-benzoyl-3''',4''-N,O-carbonylgentamicin $C_1$ to 15 ml. of dimethylformamide, heat at reflux temperature for 18 hours then evaporate the solution to a residue comprising an N-protected-O-protected intermediate.

B. Dissolve this residue in acetic acid, add 500 mg. of 30% palladium on charcoal and hydrogenate at room temperature using 60 pounds per square inch starting hydrogen pressure. Remove the catalyst by filtration and evaporate the filtrate to a residue. Dissolve the residue in 25 ml. of 5% sodium hydroxide and heat at 100° C for 4 hours. Cool the solution and pass through an IRC-50 ($H^+$ form) column, wash the resin column well with water, then elute the product with 200 ml. of 1 N ammonium hydroxide. Concentrate the ammonium hydroxide eluate to a residue comprising 5-epigentamicin $C_1$. Purify the product by chromatographing on a silica gel column eluting with the lower phase of a chloroform:methanol:15% ammonium hydroxide (2:1:1) solvent system. Combine the like eluates as determined by thin layer chromatography and lyophilize to a residue to obtain 5-epigentamicin $C_1$ (210 mg.) as a white solid; m.p. 115°–120° C, $[\alpha]_D^{26}$ + 136.5° (c, 0.32 water); Mass Spectrum: $(M)^+$ m/e 477, $(M + 1)^+$ m/e 478;

| Monosaccharides | m/e 157 - purpurosamine A ion |
|---|---|
| | m/e 160, 142 - garosamine ion |
| | m/e 191, 173, 163, 145 -5-epi-2-deoxystreptamine ions |
| Disaccharides | 350, 322, 304, |
| | 347, 319, 301 |
| NMR: δ | (100 MHz, $D_2O$) |
| 5.08, d, J=3.8Hz | H'-1' and H-1'' |
| 4.99, d, J=3 Hz | |
| 4.39, broad singlet | H-5 |
| 3.93 d, J=12.5Hz | H-5'' eq |
| 3.77, dd, J=11, J=~3.6Hz, | H-2'' |
| 3.30, d, J=12.5Hz | H-5'' ax |
| 2.66 d, J=10.5Hz | H-3'' |
| 2.53, singlet | N-CH₃ (3'') |
| 2.33, singlet, | N-CH₃(6') |
| 2.05, m | H-2 eq |
| 1.23, s | C-CH₃(4'') |
| 1.04, d, J=7Hz | CH-CH₃(6') |

C. Alternatively, the N-protecting and O-protecting groups in the intermediates prepared in Example VIII-A are removed by heating the intermediate with 1 to 2 N sodium hydroxide at 100° C until thin layer chromatographic analysis of aliquots of the reaction mixture indicate the protecting groups have been removed (usually 24 to 48 hours). Isolate and purify the resultant product in a manner similar to that described in Example VIII-B.

D. Alternatively, the N-protecting and O-protecting groups may be removed from the intermediate prepared as described in Example VIII-A in the following manner. Dissolve the product of Example VIII-A in a mixture of 10 ml. of tetrahydrofuran and 50 ml. of liquid ammonia. Slowly add 2 gms. of sodium to the stirred mixture and continue to stir for 2 hours. Allow the ammonia to evaporate by warming to room temperature overnight. Dissolve the resultant residue in 10 ml. of 5% sodium hydroxide and heat at 100° C for 4 hours. Cool and pass the solution through IRC-50 ($H^+$) resin. Wash the resin well with water and elute the product with 100 ml. of 1 N ammonium hydroxide. Concentrate the ammonium hydroxide eluate to a residue and purify this residue in a manner similar to that described in Example VIII-B to obtain 5-epigentamicin $C_1$.

EXAMPLE IX

OTHER 5-EPI-4,6-DI-O-(AMINOGLYCOSYL)-2-DEOXYSTREPTAMINES

A. In a manner similar to that described in Examples VIII-A VIII-B treat each of the following aminoglycoside derivatives with dimethylformamide at reflux temperature, thence hydrogenate each of the resulting O-protected-N-protected intermediates thereby formed in acetic acid in the presence of palladium on charcoal, and finally treat each of the resulting 2''-O-benzoyl-3'',4''-N,O-carbonyl-5-epiaminoglycosides with sodium hydroxide at 100° C.

1. 1,3,2',6'-tetra-N-benzyloxycarbonyl-5-O-methanesulfonyl-2''-O-benzoyl-3'',4''-N,O-carbonylgentamicin $C_{1a}$,
2. 1,3,2',6'-tetra-N-benzyloxycarbonyl-5-O-methanesulfonyl-2''-O-benzoyl-3'',4''-N,O-carbonylgentamicin $C_2$,
3. 1,3,2',6'-tetra-N-benzyloxycarbonyl-5-O-methanesulfonyl-2''-O-benzoyl-3'',4''-N,O-carbonylgentamicin $C_{2a}$,
4. 1,3,2',6'-tetra-N-benzyloxycarbonyl-5-O-methanesulfonyl-2''-O-benzoyl-3'',4''-N,O-carbonylgentamicin $C_{2b}$.

Isolate and purify each of the resulting products in a manner similar to that described in Example VIII-B to obtain, respectively, 5-epigentamicin $C_{1a}$, 5-epigentamicin $C_2$, 5-epigentamicin $C_{2a}$, and 5-epigentamicin $C_{2b}$.

2. Alternatively, after treatment of each of the starting materials of Example IX-A with dimethylformamide at reflux temperature the protecting groups in each of the intermediates thereby formed may be removed by treatment with sodium hydroxide according to the procedure of Example VIII-C or by reduction with sodium in ammonia followed by treatment with sodium hydroxide in the manner of Example VIII-D.

B. In a manner similar to that described in Examples VIII-A and VIII-D treat each of the following aminoglycoside derivatives with dimethylformamide at reflux temperature, then treat the resulting N-protected-O-protected intermediate with sodium in liquid ammonia followed by treatment with sodium hydroxide at 100° C.

1. 1,3,2',6'-tetra-N-benzyloxycarbonyl-5-O-methanesulfonyl-2''-O-benzoyl-3'',4''-N,O-carbonylsisomicin,
2. 1,3,2',6'-tetra-N-benzyloxycarbonyl-5-O-methanesulfonyl-2''-O-benzoyl-3'',4''-N,O-carbonylverdamicin,
3. 1,3,2',6'-tetra-N-benzyloxycarbonyl-5-O-methanesulfonyl-2''-O-benzoyl-3'',4''-N,O-carbonyl-Antibiotic G-52,
4. 1,3,2',6'-tetra-N-benzyloxycarbonyl-5-O-methanesulfonyl-2''-O-benzoyl-3'',4''-N,O-carbonyl-Antibiotic 66-40D,
5. 1,3,2',6',3''-penta-N-benzyloxycarbonyl-5-O-methanesulfonyl-2'',4''-di-O-benzoyl-Antibiotic 66-40B.

Isolate and purify each of the resultant products in a manner similar to that described in Example VIII-D to obtain, respectively,
1. 5-episisomicin,
2. 5-epiverdamicin,
3. 5-epi-Antibiotic G-52,
4. 5-epi-Antibiotic 66-40D,
5. 5-epi-Antibiotic 66-40B.

2. Alternatively, after treatment with dimethylformamide at reflux temperature the protecting groups in each of the intermediates thereby formed may be removed by treatment with sodium hydroxide in the manner of Example VIII-C to obtain the corresponding 5-epiaminoglycoside.

C. 1. In a manner similar to that described in Examples VIII-A and VIII-D treat each of the following aminoglycoside derivatives with dimethylformamide at reflux temperature, thence hydrogenate each of the resulting intermediates in acetic acid over palladium on charcoal followed by treatment of the resulting product with sodium hydroxide.

1. 1,3,2',3''-tetra-N-benzyloxycarbonyl-5-O-methanesulfonyl-3',2'',4'''-tri-O-benzoyl-4',6'-O-benzylidene-gentamicin A,
2. 1,3-di-N-benzyloxycarbonyl-5-O-methanesulfonyl-2',3'-O-cyclohexylidene-6',4';3'',4'''-di-N,O-carbonyl-2''-O-benzoylgentamicin B,
3. 1,3-di-N-benzyloxycarbonyl-5-O-methanesulfonyl-2',3'-O-cyclohexylidene-6',4';3'',4'''-di-N,O-carbonyl-2''-O-benzoylgentamicin $B_1$,
4. 1,3,2'-tri-N-benzyloxycarbonyl-5-O-methanesulfonyl-4',6'-O-cyclohexylidene-2''-O-benzoyl-3'',4''-N,O-carbonylgentamicin $X_2$,
5. 1,3,2'-tri-N-benzyloxycarbonyl-5-O-methanesulfonyl-4',6'-O-cyclohexylidene-2''-O-benzoyl-3'',4''-N,O-carbonyl-Antibiotic G-418,
6. 1,3,2',6'-tetra-N-benzyloxycarbonyl-5-O-methanesulfonyl-3',4'-O-benzylidene-2''-O-benzoyl-3'',4''-N,O-carbonyl-Antibiotic JI-20A,
7. 1,3,2',6'-tetra-N-benzyloxycarbonyl-5-O-methanesulfonyl-3',4'-O-benzylidene-2''-O-benzoyl-3'',4''-N,O-carbonyl-Antibiotic JI-20B,
8. 1,3,2',6',3''-penta-N-benzyloxycarbonyl-5-O-methanesulfonyl-3',4';4'',6''-di-O-benzylidene-2''-O-benzoylkanamycin B,
9. 1,3,2',6',3''-penta-N-benzyloxycarbonyl-5-O-methanesulfonyl-4',2''-di-O-benzoyl-4'',6''-O-benzylidene-tobramycin,
10. 1,3,6',3''-tetra-N-benzyloxycarbonyl-5-O-methanesulfonyl-2',3';4'',6''-di-O-benzylidene-4',2''-di-O-benzoylkanamycin A in admixture with 1,3,6',3''-tetra-N-benzyloxycarbonyl-5-O-methanesulfonyl-3',4';4'',6''-di-O-benzylidene-2',2''-di-O-benzoylkanamycin A,
11. 1,3,2',6',3''-penta-N-benzyloxycarbonyl-5-O-methanesulfonyl-2''-O-benzoyl-4'',6''-O-benzylidene-3',4'-dideoxykanamycin B.

2. Dissolve each of the O-ylidene-5-epiaminoglycosides obtained as described in above Example IX-C(1) in 50% aqueous acetic acid and warm the solution on the steam bath for 1 hour. Evaporate the reaction mixture in vacuo to a residue comprising each of the respective 5-epiaminoglycosides. Further purify each of these compounds via chromatographic techniques similar to those described in Example VIII-B to obtain respectively, 1. 5-epigentamicin A,
2. 5-epigentamicin B,
3. 5-epigentamicin $B_1$,
4. 5-epigentamicin $X_2$,
5. 5-epi-Antibiotic G-418,
6. 5-epi-Antibiotic JI-20A,
7. 5-epi-Antibiotic JI-20B,
8. 5-epikanamycin B,
9. 5-epitobramycin,
10. 5-epikanamycin A,
11. 5-epi-3',4'-dideoxykanamycin B.

PREPARATION OF 5-EPI-4,6-DI-O-(AMINOGLYCOSYL)-2-DEOXYSTREPTAMINES VIA OXIDATION OF THE 5-HYDROXYL FUNCTION FOLLOWED BY REDUCTION OF THE RESULTING 5'-OXO GROUP

EXAMPLE X

5-EPIGENTAMICIN $C_{1a}$

A.
1,3,2',6'-tetra-N-benzyloxycarbonyl-2''-O-benzoyl-3'',4''-N,O-carbonyl-5-dehydrogentamicin $C_{1a}$ To a solution of 1.2 gms. of 1,3,2',6'-tetra-N-benzyloxycarbonyl-2''-O-benzoyl-3'',4''-N,O-carbonyl-gentamicin $C_{1a}$ in 5 ml. of acetone at 20° C add over a 20 minute period Jones Reagent prepared from 1 gm. of chromium trioxide in 1 ml. of concentrated sulfuric acid and 1 ml. of water. Continue stirring the solution at room temperature for 16 hours then extract with chloroform, wash the chloroform extract with water, dry over sodium sulfate, and evaporate the solution to a residue (0.619 g.) comprising 1,3,2',6'-tetra-N-benzyloxycarbonyl-2''-O-benzoyl-3'',4''-N,O-carbonyl-5-dehydrogentamicin $C_{1a}$.

B.
1,3,2',6'-tetra-N-benzyloxycarbonyl-2''-O-benzoyl-3'',4''-N,O-carbonyl-5-epigentamicin $C_{1a}$ Dissolve the N-protected-O-protected-5-dehydrogentamicin $C_{1a}$ prepared in Example X-A in 10 ml. of methanol. Add 100 mg. of sodium borohydride and warm the mixture at 40° C for 4 hours. Cool the solution, remove the solvent in vacuo and extract the resultant residue with chloroform. Wash the combined chloroform extracts with water, dry over sodium sulfate and evaporate the solvent to a residue comprising 1,3,2',6'-tetra-N-benzyloxycarbonyl-2''-O-benzoyl-3'',4''-N,O-carbonyl-5-epigentamicin $C_{1a}$.

C.
2''-O-benzoyl-3'',4''-N,O-carbonyl-5-epigentamicin $C_{1a}$

Dissolve the product obtained in Example X-B in 15 ml. of acetic acid and hydrogenate over 200 mg. of 30% palladium on charcoal at room temperature for 18 hours at 60 pounds per square inch starting pressure. Filter and evaporate the filtrate in vacuo to a residue comprising 2''-O-benzoyl-3'',4''-N,O-carbonyl-5-epigentamicin $C_{1a}$.

D. 5-epigentamicin $C_{1a}$

Dissolve the product of Example X-C in 10 ml. of 5% sodium hydroxide and heat at 100° C for 4 hours, cool and pass the solution through IRC-50 (H$^+$) resin, wash the resin well with water, then elute the product with 100 ml. of 1 N ammonium hydroxide. Evaporate the ammonium hydroxide eluate to a residue comprising 5-epigentamicin $C_{1a}$. Purify by chromatographing on a silica gel column eluting with the lower phase of a chloroform:methanol:15% ammonium hydroxide (2:1:1) solvent system. Combine the like eluates as determined by thin layer chromatography and evaporate the combined eluates to a residue comprising 5-epigentamicin $C_{1a}$; m.p. 145°–152° C, $[\alpha]_D^{26} + 149°$ C (c, 0.55, $H_2O$).

2. Alternatively, the compound of this example is prepared as described in following Examples X-E to X-I.

E.
1,3,2',6',3''-penta-N-benzyloxycarbonyl-2''-O-acetyl-5-dehydrogentamicin $C_{1a}$ To a solution of 10 gms. of 1,3,2',6',3''-penta-N-benzyloxycarbonyl-2''-O-acetylgentamicin $C_{1a}$ in 600 ml. of methylene chloride under an atmosphere of argon add 11.2 gms. of chromium trioxide-pyridine complex. Heat the resulting slurry at reflux temperature. Add 12.1 gms. of additional chromium trioxide-pyridine complex after 22 hours and 11.2 gms. of additional chromium trioxide-pyridine complex after 25 hours. When the reaction is complete as indicated by thin layer chromatography (usually about 28 hours) evaporate about 500 ml. of the solvent in vacuo, add 600 ml. of ether to the resulting solution, decant the ethereal solution from the resulting tarry precipitate and wash the precipitate with 200 ml. of ether. Wash the combined ethereal solutions with saturated sodium bicarbonate solution (2 times) with 1 N hydrochloric acid (3 times) and then with water (2 times). Dry over sodium sulfate and evaporate in vacuo to a residue (8.2 gms.) comprising 1,3,2',6',3''-penta-N-benzyloxycarbonyl-2''-O-acetyl-5-dehydrogentamicin $C_{1a}$. Further purify by chromatographing on a 700 gm. silica gel "dry" column. Develop the column with 60% ethyl acetate/40% chloroform, then elute the product with ethyl acetate and evaporate the combined eluates to a residue (4.6 gms.) comprising the 1,3,2',6',3''-penta-N-benzyloxycarbonyl-2''-O-acetyl-5-dehydrogentamicin $C_{1a}$; NMR: ($CDCl_3$—$CD_3OD$, (3:1)); δ 2.93 (N-$CH_3$), 1.90 ($CH_3COO$), 1.04 (C—$CH_3$) ppm, CMR: ($CDCl_3$—$CD_3OD$ (3:1)); 201 ppm (C=O).

In a manner similar to that described hereinabove, treat 1,3,2',6'-tetra-N-benzyloxycarbonyl-2''-O-acetyl-3'',4''-N,O-carbonylgentamicin $C_{1a}$ with chromium trioxide-pyridine complex. Isolate and purify the resultant products in a manner similar to that described to obtain 1,3,2',6'-tetra-N-benzyloxycarbonyl-2''-O-acetyl-3'',4''-N,O-carbonyl-5-dehydrogentamicin $C_{1a}$.

F. To a solution of 2.1 gms. of 1,3,2',6',3''-penta-N-benzyloxycarbonyl-2''-O-acetyl-5-dehydrogentamicin $C_{1a}$ in 40 ml. of dry tetrahydrofuran under an atmosphere of argon add 8 ml. of 1 M "L-Selectride" (lithium tri-sec-butyl borohydride in tetrahydrofuran). Stir the mixture under an atmosphere of nitrogen at room temperature for 20 hours, pour into 400 ml. of aqueous sodium chloride and extract with 3 × 80 ml. portions of ethyl acetate. Wash the combined ethyl acetate extract 3 times with water (containing some sodium chloride). Dry over sodium sulfate and evaporate in vacuo to a residue (2.2 gms.) comprising a 1,3,2',6'-tetra-N-benzyloxycarbonyl-3'',4''-N,O-carbonyl derivative of gentamicin $C_{1a}$, which is used without further purification in the the procedure of Example X-G. Alternatively, the above procedure may be carried out on 1,3,2',6'-tetra-N-benzyloxycarbonyl-2''-O-acetyl-3'',4''-N,O-carbonyl-5-dehydrogentamicin $C_{1a}$ to obtain the same product obtained in the paragraph above.

G. 3'',4''-N,O-carbonyl-5-epigentamicin $C_{1a}$

Dissolve the product (2.2 gms.) obtained in the first paragraph of above Example X-F in 20 ml. of dry tetrahydrofuran, cool the solution to −75° to −85° C and condense 300 ml. of ammonia into the reaction vessel. Add 2.2 gms. of sodium metal and stir the reaction mixture vigorously for 2.5 hours. Slowly add 20 ml. of water to the mixture and allow the ammonia to evaporate with warming to room temperature. Absorb the residual solution on a BioRex 70 cation exchange resin (100 ml., $H^+$ form). Wash the neutral impurities off with water (400 ml.) then elute the product with 1.5 N ammonium hydroxide. Combine the like ammonium hydroxide eluates as determined by thin layer chromatography and evaporate in vacuo to a residue comprising 3'',4''-N,O-carbonyl-5-epigentamicin $C_{1a}$, which is used without further purification in the procedure of Example X-H.

H. 5-epigentamicin $C_{1a}$

Dissolve 143 mgs. of 3'',4''-N,O-carbonyl-5-epigentamicin $C_{1a}$ prepared as described in Example X-G in 20 ml. of 2 N sodium hydroxide. Heat the solution at reflux temperature for 4 hours then cool to room temperature and place on a BioRex 70 cation exchange resin column (100 ml., $H^+$ form). Wash off the neutral salts with 200 ml. of water, then elute with 200 ml. of 1.5 N ammonium hydroxide. Concentrate the combined ammonium hydroxide eluate in vacuo to a residue comprising 5-epigentamicin $C_{1a}$, yield 139 mg. Purify by chromatographing on a 33 gm. silica gel column eluting with the lower phase of a chloroform:methanol:concentrated ammonium hydroxide solvent system (1:1:1). Combine the like fractions as determined by thin layer chromatography and evaporate in vacuo to give purified 5-epigentamicin $C_{1a}$, yield 72 mg.; Mass Spectrum: m/e 450 (M + H)$^+$; 322, 304, 160, 129.

I. Alternatively, the compound of this example is prepared as follows. Treat 1,3,2',6'-tetra-N-benzyloxycarbonyl-2''-O-benzoyl-3'',4''-N,O-carbonyl-5-epigentamicin $C_{1a}$ or 1,3,2',6',3''-penta-N-benzyloxycarbonyl-5-epigentamicin $C_{1a}$ with sodium hydroxide in a manner similar to that described in Example VIII-C and isolate each of the respective products in a manner similar to that described to obtain 5-epigentamicin $C_{1a}$.

EXAMPLE XI

OTHER 5-EPI-4,6-DI-O-(AMINOGLYCOSYL)-2-DEOXYSTREPTAMINES PREPARED VIA THE PROCEDURE OF EXAMPLE X

A. (1) Treat each of the following -N-protected-O-protected-aminoglycosides with chromium trioxide-pyridine complex in methylene chloride in a manner similar to that described in Example X-E 1. 1,3,2',6',3''-penta-N-benzyloxycarbonyl-2''-O-acetylgentamicin $C_1$,
2. 1,3,2',6',3''-penta-N-benzyloxycarbonyl-2''-O-acetylgentamicin $C_2$,
3. 1,3,2',6',3''-penta-N-benzyloxycarbonyl-2''-O-acetylgentamicin $C_{2a}$,
4. 1,3,2',6',3''-penta-N-benzyloxycarbonyl-2''-O-acetylgentamicin $C_{2b}$,
5. 1,3,2',6',3''-penta-N-benzyloxycarbonyl-2''-O-acetyl-Antibiotic G-52, 6. 1,3,2',6',3''-penta-N-benzyloxycarbonyl-2''-O-acetylverdamicin, 7. 1,3,2',6',3''-penta-N-benzyloxycarbonyl-2''-O-acetylsisomicin, 8. 1,3,2',6',3''-penta-N-benzyloxycarbonyl-2'',4''-di-O-acetyl-Antibiotic 66-40D, 9. 1,3,2',3''-tetra-N-benzyloxycarbonyl-3',2'',4''-tri-O-acetyl-4',6'-O-benzylidenegentamicin A, 10. 1,3,-di-N-benzyloxycarbonyl-2',3'-O-cyclohexylidene-6',4';3'',4''-di-N,O-carbonyl-2''-O-acetylgentamicin B, 11. 1,3-di-N-benzyloxycarbonyl-2',3'-O-cyclohexylidene-6',4';3'',4''-di-N,O-carbonyl-2''-O-acetylgentamicin B₁, 12. 1,3,2',3''-tetra-N-benzyloxycarbonyl-4',6'-O-cyclohexylidene-3',2''-di-O-acetylgentamicin X₂, 13. 1,3,2',3''-tetra-N-benzyloxycarbonyl-4',6'-O-cyclohexylidene-3',2''-di-O-acetyl-Antibiotic G-418, 14. 1,3,2',6',3''-penta-N-benzyloxycarbonyl-3',4'-O-benzylidene-2''-O-acetyl-Antibiotic JI-20A, 15. 1,3,2',6',3''-penta-N-benzyloxycarbonyl-3',4'-O-benzylidene-2''-O-acetyl-Antibiotic JI-20B, 16. 1,3,2',6',3''-penta-N-benzyloxycarbonyl-3',4';-4'',6''-di-O-benzylidene-2''-O-acetylkanamycin B, 17. 1,3,2',6',3''-penta-N-benzyloxycarbonyl-4',2''-di-O-acetyl-4'',6''-O-benzylidene-tobramycin, 18. 1,3,6',3''-tetra-N-benzyloxycarbonyl-2',3';4'',6''-di-O-benzylidene-4',2''-di-O-acetylkanamycin A in admixture with 1,3,6',3''-tetra-N-benzyloxycarbonyl-3',4';4'',6''-di-O-benzylidene-2',2''-di-O-acetylkanamycin A, 19. 1,3,2',6',3''-penta-N-benzyloxycarbonyl-2''-O-acetyl-4',6'-O-benzylidene-3',4'-dideoxykanamycin B.

Isolate and purify each of the resultant products in a manner similar to that described in Example X-E to obtain the following 5-dehydro intermediates, respectively, 1. 1,3,2',6',3''-penta-N-benzyloxycarbonyl-2''-O-acetyl-5-dehydrogentamicin C₁, 2. 1,3,2',6',3''-penta-N-benzyloxycarbonyl-2''-O-acetyl-5-dehydrogentamicin C₂, 3. 1,3,2',6',3''-penta-N-benzyloxycarbonyl-2''-O-acetyl-5-dehydrogentamicin C₂ₐ, 4. 1,3,2',6',3''-penta-N-benzyloxycarbonyl-2''-O-acetyl-5-dehydrogentamicin C₂ᵦ, 5. 1,3,2',6'3''-penta-N-benzyloxycarbonyl-2''-O-acetyl-5-dihydro-Antibiotic G-52, 6. 1,3,2',6',3''-penta-N-benzyloxycarbonyl-2''-O-acetyl-5-dehydroverdamicin, 7. 1,3,2',6',3''-penta-N-benzyloxycarbonyl-2''-O-acetyl-5-dehydrosisomicin, 8. 1,3,2',6',3''-penta-N-benzyloxycarbonyl-2'',4''-di-O-acetyl-5-dehydro-Antibiotic 66-40D, 9. 1,3,2',3''-tetra-N-benzyloxycarbonyl-3',2'',4''-tri-O-acetyl-4',6'-O-benzylidene-5-dehydrogentamicin A, 10. 1,3-di-N-benzyloxycarbonyl-2',3'-O-cyclohexylidene-6',4';3'',4''-di-N,O-carbonyl-2''-O-acetyl-5-dehydrogentamicin B, 11. 1,3-di-N-benzyloxycarbonyl-2',3'-O-cyclohexylidene-6',4';3'',4''-di-N,O-carbonyl-2''-O-acetyl-5-dehydrogentamicin B₁, 12. 1,3,2',3''-tetra-N-benzyloxycarbonyl-4',6'-O-cyclohexylidene-3',2''-di-O-acetyl-5-dehydrogentamicin X₂, 13. 1,3,2',3''-tetra-N-benzyloxycarbonyl-4',6'-O-cyclohexylidene-3',2''-di-O-acetyl-5-dehydro-Antibiotic G-418, 14. 1,3,2',6',3''-penta-N-benzyloxycarbonyl-3',4'-O-benzylidene-2''-O-acetyl-5-dehydro-Antibiotic JI-20A, 15. 1,3,2',6',3''-penta-N-benzyloxycarbonyl-3',4'-O-benzylidene-2''-O-acteyl-5-dehydro-Antibiotic JI-20B, 16. 1,3,2',6',3''-penta-N-benzyloxycarbonyl-3',4';-4'',6''-di-O-benzylidene-2''-O-acetyl-5-dehydrokanamycin B, 17. 1,3,2',6',3''-penta-N-benzyloxycarbonyl-4',2''-di-O-acetyl-4'',6''-O-benzylidene-5-dehydrotobramycin, 18. 1,3,6',3''-tetra-N-benzyloxycarbonyl-2',3';4'',6''-di-O-benzylidene-4',2''-di-O-acetyl-5-dehydrokanamycin A in admixture with 1,3,6',3''-tetra-N-benzyloxycarbonyl-3',4';4'',6''-di-O-benzylidene-2',2''-di-O-acetyl-5-dehydrokanamycin A, 19. 1,3,2',6',3''-penta-N-benzyloxycarbonyl-4',6'-O-benzylidene-2''-O-acetyl-5-dehydro-3',4'-dideoxykanamycin B.

A. (2) Alternatively, compounds of this example are prepared as follows. Treat each of the following 2''-O-benzoyl-N-protected-O-protected-aminoglycosides with chromium trioxide in concentrated sulfuric acid and isolate in a manner similar to that described in Example X-A.

1. 1,3,2',6'-tetra-N-benzyloxycarbonyl-2''-O-benzoyl-3'',4''-N,O-carbonylgentamicin C₁, 2. 1,3,2',6'-tetra-N-benzyloxycarbonyl-2''-O-benzoyl-3'',4''-N,O-carbonylgentamicin C₂, 3. 1,3,2',6'-tetra-N-benzyloxycarbonyl-2''-O-benzoyl-3'',4''-N,O-carbonylgentamicin C₂ₐ, 4. 1,3,2',6'-tetra-N-benzyloxycarbonyl-2''-O-benzoyl-3'',4''-N,O-carbonylgentamicin C₂ᵦ, 5. 1,3,2',6'-tetra-N-benzyloxycarbonyl-2''-O-benzoyl-3'',4''-N,O-carbonyl-Antibiotic G-52, 6. 1,3,2',6'-tetra-N-benzyloxycarbonyl-2''-O-benzoyl-3'',4''-N,O-carbonylverdamicin, 7. 1,3,2',6'-tetra-N-benzyloxycarbonyl-2''-O-benzoyl-3'',4''-N,O-carbonylsisomicin, 8. 1,3,2',6'-tetra-N-benzyloxycarbonyl-2''-O-benzoyl-3'',4''-N,O-carbonyl-Antibiotic 66-40D, 9. 1,3,2',3'-tetra-N-benzyloxycarbonyl-3',2'',4''-tri-O-benzoyl-4',6'-O-benzylidene-gentamicin A, 10. 1,3-di-N-benzyloxycarbonyl-2',3'-O-cyclohexylidine-6',4';3'',4''-di-N,O-carbonyl-2''-O-benzoylgentamicin B, 11. 1,3,di-N-benzyloxycarbonyl-2',3'-O-cyclohexylidene-6',4';3'',4''-di-N,O-carbonyl-2''-O-benzoylgentamicin B₁, 12. 1,3,2'-tri-N-benzyloxycarbonyl-4',6'-O-cyclohexylidene-3',2''-di-O-benzoyl-3'',4''-N,O-carbonylgentamicin X₂, 13. 1,3,2'-tri-N-benzyloxycarbonyl-4',6'-O-cyclohexylidene-3',2''-di-O-benzoyl-3'',4''-N,O-carbonyl-Antibiotic G-418, 14. 1,3,2',6'-tetra-N-benzyloxycarbonyl-3',4'-O-benzylidene-2''-O-benzoyl-3'',4''-N,O-carbonyl-Antibiotic JI-20A, 15. 1,3,2',6'-tetra-N-benzyloxycarbonyl-3',4'-O-benzylidene-2''-O-benzoyl-3'',4''-N,O-carbonyl-Antibiotic JI-20B, 16. 1,3,2',6',3''-penta-N-benzyloxycarbonyl-3',4';-4'',6''-di-O-benzylidene-2''-O-benzoylkanamycin B, 17. 1,3,2',6',3''-penta-N-benzyloxycarbonyl-4',2''-di-O-benzoyl-4'',6''-O-benzylidene-tobramycin, 18. 1,3,6',3''-tetra-N-benzyloxycarbonyl-2',3';4'',-6''-di-O-benzylidene-4',2''-O-benzoyl-kanamycin A in admixture with 1,3,6',3''-tetra-N-benzyloxycarbonyl-3',4';4'',6''-di-O-benzylidine-2',2''-di-O-benzoylkanamycin A, 19. 1,3,2',6',3''-penta-N-benzyloxycarbonyl-2''-O-benzoyl-4'',6''-O-benzylidene-3',4'-dideoxykanamycin B.

Isolate and purify each of the resultant products in a manner similar to that described in Example X-A to obtain each of the respective products listed hereinabove in Example XI-A(1).

The starting intermediates for the above procedure XI-A(2) may contain an acetyl function instead of the benzoyl functions listed hereinabove, and there will be obtained the corresponding 5-dehydro compounds containing an acetyl function in place of the benzoyl function listed therein.

B. Treat each of the 5-dehydro compounds prepared as described in above Example XI-A(1) or XI-A(2) with lithium tri-secondary butyl borohydride in tetrahydrofuran in a manner similar to that described in Example X-F then treat each of the resultant N-protected-O-protected-5-epiaminoglycosides thereby formed with sodium in liquid ammonia in a manner similar to that described in Example X-G to remove the benzyloxycarbonyl protecting groups, then treat each of the resultant intermediates thereby formed with 2 N sodium hydroxide according to the procedure described in Example X-H to obtain, respectively, 1. 5-epigentamicin $C_1$,
2. 5-epigentamicin $C_2$,
3. 5-epigentamicin $C_{2a}$,
4. 5-epigentamicin $C_{2b}$,
5. 5-epi-Antibiotic G-52,
6. 5-epiverdamicin,
7. 5-episisomicin,
8. 5-epi-Antibiotic 66–40D,
9. 4',6'-O-benzylidene-5-epigentamicin A,
10. 2',3'-O-cyclohexylidene-5-epigentamicin B,
11. 2',3'-O-cyclohexylidene-5-epigentamicin $B_1$,
12. 4',6'-O-cyclohexylidene-5-epigentamicin $X_2$,
13. 4',6'-O-cyclohexylidene-5-epi-Antibiotic G-418,
14. 3',4'-O-benzylidene-5-epi-Antibiotic JI-20A,
15. 3',4'-O-benzylidene-5-epi-Antibiotic JI-20B,
16. 3',4';4'',6''-di-O-benzylidene-5-epikanamycin B,
17. 4'',6''-O-benzylidene-tobramycin,
18. 2',3';4'',6''-di-O-benzylidene-5-epikanamycin A in admixture with 3',4';4'',6''-di-O-benzylidene-5-epikanamycin A,
19. 4',6'-O-benzylidene-5-epi-3',4'-dideoxykanamycin B.

C. In a manner similar to that described in Example IX-C(2) treat each of products 9-19 obtained in above Example XI-B with 50% aqueous acetic acid on a steam bath then isolate and purify each of resultant products 9-19 in a manner similar to that described to obtain, respectively, 9. 5-epigentamicin A,
10. 5-epigentamicin B,
11. 5-epigentamicin $B_1$,
12. 5-epigentamicin $X_2$,
13. 5-epi-Antibiotic G-418,
14. 5-epi-Antibiotic JI-20A,
15. 5-epi-Antibiotic JI-20B,
16. 5-epikanamycin B,
17. 5-epitobramycin,
18. 5-epikanamycin A,
19. 5-epi-3',4'-dideoxykanamycin B.

PREPARATION OF 5-EPI-4,6-DI-O-(AMINOGLYCOSYL)-2-DEOXYSTREPTAMINES VIA REACTION OF THE 5-O-HYDROCARBONSULFONYL DERIVATIVE WITH DIMETHYLFORMAMIDE IN PRESENCE OF A TETRAALKYLAMMONIUM ALKANOATE

EXAMPLE XII

5-EPISISOMICIN AND 1-N-ALKYL-5-EPISISOMICIN

A. 5-Episisomicin

1. Add 1.2 gm. of 1,3,2',6'-tetra-N-benzyloxycarbonyl-5-O-methanesulfonyl-2''-O-benzoyl-3'',4''-N,O-carbonylsisomicin and 1.0 gm. of tetra-n-butylammonium acetate to 10 ml. of dimethylformamide. Heat at 120° C for 16 hours, evaporate to a residue and extract the residue with chloroform. Wash the chloroform solution with water, dry over sodium sulfate, then evaporate in vacuo to a residue comprising 1,3,2',6'-tetra-N-benzyloxycarbonyl-5-epi-O-acetyl-2''-O-benzoyl-3'',4''-N,O-carbonylsisomicin.

2. Dissolve the residue obtained in above Example XII-A(1) in 10 ml. of dimethylsulfoxide. Add a solution of 2 gm. of potassium hydroxide in 4 ml. of water and heat at 100° C for 24 hours. Cool the reaction mixture, add 80 ml. of Amberlite IRC-50 ($H^+$), stir the mixture for 1 hour, then separate the resin, wash with water, then elute with 10 N ammonium hydroxide. Concentrate the combined ammonium hydroxide eluates in vacuo and chromatograph the resultant residue over 25 gm. of silica gel eluting with the lower phase of a 2:1:1 chloroform:methanol:10 N ammonium hydroxide solvent system. Combine the like eluates containing 5-episisomicin as determined by thin layer chromatography and evaporate the combined eluates to a residue of 5-episisomicin (yield 143 mg.); m.p. 135°–138° C (dec.); $[\alpha]_D^{26}$ + 187.3 ($D_2O$); Mass Spectrum $(M)^+$ m/e 447, $(M + 1)^+$ m/e 448.

| | | |
|---|---|---|
| Monosaccharides | m/e 160, 127. | |
| 2-Deoxystreptamines | m/e 191, 173, 163, 145. | |
| Disaccharides | m/e 317, 289, 271, | |
| | m/e 350, 322, 304 | |
| PMR (δ) $D_2O$: | | |
| 5.14 | d, J=2.5 Hz | 1'-H |
| 5.07 | d, J=4.0 Hz | 1''-H |
| 4.89 | broad singlet | 4'-H |
| 4.37 | broad singlet | 5-H |
| 3.94 | d, J=12.5 Hz | 5''e-H |
| 3.77 | q. | 2''-H |
| 3.39 | d, J=12.0 Hz | 5''a-H |
| 3.21 (2H) | broad singlet | 6'-H |
| 2.65 | d, J=11 Hz | 3''-H |
| 2.52 | singlet | 3''-N-CH₃ |
| 1.23 | singlet | 4''-C-CH₃ |
| CMR ($D_2O$): | | |

PPM: δ150.3, 102.6, 97.1 (2C), 85.8, 80.9, 73.3, 70.3, 69.7, 68.5, 64.0, 48.1, 47.2, 47.1, 43.2, 37.7, 36.4, 25.6, 22.4.

B. 1-N-Ethyl-5-Episisomicin

1. The requisite intermediate, i.e. 1-N-ethyl-1,3,2',6'-tetra-N-benzyloxycarbonyl-5-O-methanesulfonyl-2''-O-benzoyl-3'',4''-N,O-carbonylsisomicin is prepared by reacting 1-N-ethylsisomicin according to the procedures of Examples I – IV.

In a manner similar to that described in Example XII-A treat 1-N-ethyl-1,3,2',6'-tetra-N-benzyloxycarbonyl-5-O-methanesulfonyl-2''-O-benzoyl-3'',4''-N,O-carbonylsisomicin in dimethylformamide in the presence of tetra-n-butylammonium acetate at 120° C for 16 hours. Isolate the resulting 5-epi-O-acetate derivative in the manner described in Example XII-A(1), then treat this derivative with aqueous potassium hydroxide in the manner of Example XII-A(2) followed by purification via chromatographic techniques as described to obtain 1-N-ethyl-5-episisomicin; m. p. 118°–122° C (dec.); Mass Spectrum (M)$^+$ m/e 475, (M + 1)$^+$ m/e 476.

| Monosaccharides | m/e 160, 127. | |
|---|---|---|
| 2-Deoxystreptamines | m/e 219, 201, 191, 173. | |
| Disaccharides | m/e 345, 317, 299, | |
|  | m/e 378, 350, 322. | |
| PMR (δ) D$_2$O: | | |
| 5.14 | d, J=2.5 Hz | 1'-H |
| 5.00 | d, J=4.1 Hz | 1''-H |
| 4.9 | broad singlet | 4'-H |
| 4.38 | broad singlet | 5-H |
| 3.93 | d, J=12.5 Hz | 5''e-H |
| 3.78 | q. | 2''-H |
| 3.38 | d, J=12.5 Hz | 5''a-H |
| 3.21 (1H) | broad singlet | 6'-H |
| 2.65 | d, J=11.0 Hz | 3''-H |
| 2.52 | singlet | 3''-N-CH$_3$ |
| 1.22 | singlet | 4''-C-CH$_3$ |
| 1.07 | triplet | 1-N-CH$_2$-CH$_3$ |

C. Other 1-N-Alkyl-5-Episisomicin Derivatives

1. In a manner similar to that described in Example XII-A treat an equivalent quantity of each of the following 1-N-alkylsisomicin derivatives (prepared from the corresponding 1-N-alkylsisomicins via the procedures of Examples I – IV) with dimethylformamide in the presence of tetra-n-butylammonium acetate.

1. 1-N-propyl-1,3,2',6'-tetra-N-benzyloxycarbonyl-5-O-methanesulfonyl-2''-O-benzoyl-3'',4''-N,O-carbonylsisomicin, 2. 1-N-(n-butyl)-1,3,2',6'-tetra-N-benzyloxycarbonyl-5-O-methanesulfonyl-2''-O-benzoyl-3'',4''-N,O-carbonylsisomicin, 3. 1-N-(δ-benzyloxycarbonylaminobutyl)-1,3,2',6'-tetra-N-benzyloxycarbonyl-5-O-methanesulfonyl-2''-O-benzoyl-3'',4''-N,O-carbonylsisomicin, 4. 1-N-(γ-benzyloxycarbonylaminopropyl)-1,3,2',6'-tetra-N-benzyloxycarbonyl-5-O-methanesulfonyl-2''-O-benzoyl-3'',4''-N,O-carbonylsisomicin, 5. 1-N-(β-methylpropyl)-1,3,2',6'-tetra-N-benzyloxy-carbonyl-5-O-methanesulfonyl-2''-O-benzoyl-3'',4''-N,O-carbonylsisomicin, 6. 1-N-(n-pentyl)-1,3,2',6'-tetra-N-benzyloxycarbonyl-5-O-methanesulfonyl-2''-O-benzoyl-3'',4''-N,O-carbonylsisomicin, 7. 1-N-(γ-methylbutyl)-1,3,2',6'-tetra-N-benzyloxycarbonyl-5-O-methanesulfonyl-2''-O-benzoyl-3'',4''-N,O-carbonylsisomicin, 8. 1-N-(β-methylbutyl)-1,3,2',6'-tetra-N-benzyloxycarbonyl-5-O-methanesulfonyl-2''-O-benzoyl-3'',4''-N,O-carbonylsisomicin, 9. 1-N-(β,β-dimethylpropyl)-1,3,2',6'-tetra-N-benzyloxycarbonyl-5-O-methanesulfonyl-2''-O-benzoyl-3'',4''-N,O-carbonylsisomicin, 10. 1-N-(β-ethylbutyl)-1,3,2',6'-tetra-N-benzyloxycarbonyl-5-O-methanesulfonyl-2''-O-benzoyl-3'',4''-N,O-carbonylsisomicin, 11. 1-N-(N-octyl)-1,3,2',6'-tetra-N-benzyloxycarbonyl-5-O-methanesulfonyl-2''-O-benzoyl-3'',4''-N,O-carbonylsisomicin, 12. 1-N-(β-propenyl)-1,3,2',6'-tetra-N-benzyloxycarbonyl-5-O-methanesulfonyl-2''-O-benzoyl-3'',4''-N,O-carbonylsisomicin, 13. 1-N-(β-ethyl-β-hexenyl)-1,3,2',6'-tetra-N-benzyloxycarbonyl-5-O-methanesulfonyl-2''-O-benzoyl-3'',4''-N,O-carbonylsisomicin, 14. 1-N-benzyl-1,3,2',6'-tetra-N-benzyloxycarbonyl-5-O-methanesulfonyl-2''-O-benzoyl-3'',4''-N,O-carbonylsisomicin, 15. 1-N-phenethyl-1,3,2',6'-tetra-N-benzyloxycarbonyl-5-O-methanesulfonyl-2''-O-benzoyl-3'',4''-N,O-carbonylsisomicin, 16. 1-N-cyclohexylmethyl-1,3,2',6'-tetra-N-benzyloxycarbonyl-5-O-methanesulfonyl-2''-O-benzoyl-3'',4''-N,O-carbonylsisomicin, 17. 1-N-(δ-benzoyloxybutyl)-1,3,2',6'-tetra-N-benzyloxycarbonyl-5-O-methanesulfonyl-2''-O-benzoyl-3'',4''-N,O-carbonylsisomicin, 18. 1-N-(ω-benzoyloxyoctyl)-1,3,2',6'-tetra-N-benzyloxycarbonyl-5-O-methanesulfonyl-2''-O-benzoyl-3'',4''-N,O-carbonylsisomicin, 19. 1-N-(β-benzyloxycarbonylaminoethyl)-1,3,2',6'-tetra-N-benzyloxycarbonyl-5-O-methanesulfonyl-2''-O-benzoyl-3'',4''-N,O-carbonylsisomicin, 2. Isolate the corresponding 5-epi-O-acetyl derivative in the described manner followed by treatment thereof with aqueous potassium hydroxide and isolation of the resultant product in the manner of Example XII-A(2) to obtain, respectively, 1. 1-N-propyl-5-episisomicin,
2. 1-N-(n-butyl)-5-episisomicin,
3. 1-N-(δ-aminobutyl)-5-episisomicin,
4. 1-N-(γ-aminopropyl)-5-episisomicin,
5. 1-N-(β-methylpropyl)-5-episisomicin,
6. 1-N-(n-pentyl)-5-episisomicin,
7. 1-N-(γ-methylbutyl)-5-episisomicin,
8. 1-N-(β-methylbutyl)-5-episisomicin,
9. 1-N-(β,β-dimethylpropyl)-5-episisomicin,
10. 1-N-(β-ethylbutyl)-5-episisomicin,
11. 1-N-(n-octyl)-5-episisomicin,
12. 1-N-(β-propenyl)-5-episisomicin,
13. 1-N-(β-ethyl-β-hexenyl)-5-episisomicin,
14. 1-N-benzyl-5-episisomicin,
15. 1-N-phenethyl-5-episisomicin,
16. 1-N-cyclohexylmethyl-5-episisomicin,
17. 1-N-(δ-hydroxybutyl)-5-episisomicin,
18. 1-N-(ω-hydroxyoctyl)-5-episisomicin,
19. 1-N-(β-aminoethyl)-5-episisomicin,

EXAMPLE XIII

OTHER 1-N-ALKYL-5-EPI-4,6-DI-O-(AMINOGLYCOSYL)-2-DEOXYSTREPTAMINES

A. 1-N-Ethyl Derivatives

1. In the manner of Example XII-A treat an equivalent quantity of the 1-N-ethyl derivatives of the per-N-benzyloxycarbonyl-5-O-methanesulfonyl-2''-O-benzoyl-3'',4''-N,O-carbonyl intermediates of Example IV-A and B with dimethylformamide in the presence of tetra-n-butylammonium acetate followed by treatment of the thereby formed 5-epi-O-acetyl-N-protected-O-protected intermediate with aqueous potassium hydroxide in dimethylformamide followed by isolation and purification in the described manner to obtain, respectively, 1. 1-N-ethyl-5-epigentamicin $C_{1a}$,
2. 1-N-ethyl-5-epigentamicin $C_1$,
3. 1-N-ethyl-5-epigentamicin $C_2$,
4. 1-N-ethyl-5-epigentamicin $C_{2a}$,
5. 1-N-ethyl-5-epigentamicin $C_{2b}$, 6. 1-N-ethyl-5-epi-Antibiotic G-52,
7. 1-N-ethyl-5-epiverdamicin,
8. 1-N-ethyl-5-epi-Antibiotic 66-40D.

2. In the manner of Example XII-A(1) treat an equivalent quantity of the 1-N-ethyl derivative of each of the 5-O-methanesulfonyl-2''-O-benzoyl-O-ylidene-N-benzyloxycarbonyl intermediates of Example VII with dimethylformamide in the presence of tetra-n-butylammonium acetate followed by treatment of the resulting 5-epi-O-acetyl-N-protected-O-protected intermediate with aqueous potassium hydroxide in the manner of Example XII-A(2) followed by treatment of the O-ylidene-5-epi-4,6-di-O-(aminoglycosyl)-2-deoxystreptamines thereby obtained with 50% aqueous acetic acid in a manner similar to that described in Example IX-C(1) to obtain, respectively, 1. 1-N-ethyl-5-epi-3',4'-dideoxykanamycin B,
2. 1-N-ethyl-5-epigentamicin B,
3. 1-N-ethyl-5-epigentamicin $B_1$,
4. 1-N-ethyl-5-epi-Antibiotic JI-20A,
5. 1-N-ethyl-5-epi-Antibiotic JI-20B,
6. 1-N-ethyl-5-epikanamycin B,
7. 1-N-ethyl-5-epitobramycin,
8. 1-N-ethyl-5-epi-Antibiotic 66-40B,
9. 1-N-ethyl-5-epigentamicin $X_2$,
10. 1-N-ethyl-5-epi-Antibiotic G-418,
11. 1-N-ethyl-5-epikanamycin A,
12. 1-N-ethyl-5-epigentamicin A.

B. Other 1-N-Alkyl-5-Epi-4,6-Di-O-(Aminoglycosyl)-2-Deoxystreptamines

In the procedures of above Examples XIII-A(1) and (2) substitute for the 1-N-ethyl-N-protected-O-protected intermediates listed therein other 1-N-alkyl derivatives of th aminoglycosides listed therein, i.e. derivatives corresponding to the 1-N-substituted sisomicin starting compounds of Example XII-C to obtain the corresponding 1-N-alkyl-5-epi-4,6-di-O-(aminoglycosyl)-2-deoxystreptamines.

PREPARATION OF 1-N-ALKYL-5-EPI-4,6-DI-O-(AMINOGLYCOSYL)-1,3-DIAMINOCYCLITOLS VIA REDUCTION OF THE CORRESPONDING 1-N-ACYL DERIVATIVES

EXAMPLE XIV

1N-Acyl-5-Epi-4,6-Di-O-(Aminoglycosyl)-1,3-Diaminocyclitols

A. 1-N-Acetyl-5-Episisomicin

Dissolve 1.25 gm. of 5-episisomicin sulfate in 200 ml. of water/methanol (2:3 v/v) and chill the solution. Add 1.5 ml. of acetic anhydride and after approximately 10 minutes, add 0.125 ml. of triethylamine in 10 ml. of methanol over a 15 minute interval. Allow the reaction mixture to warm to room temperature over a 2 hour interval, then evaporate the solvent in vacuo. Dissolve the residue in water, and convert the product to the free base by passage of an aqueous solution thereof through Amberlite IRA-401S resin in the hydroxide ion cycle. Lyophilize the column eluate and chromatograph the residue on 50 gm. of silica gel using the lower phase of (2:1:1) chloroform:methanol: 7% ammonium hydroxide solvent system as eluant. Monitor the fractions via thin layer chromatography and combine like fractions and evaporate to a residue comprising 1-N-acetyl-5-episisomicin.

B. In similar manner treat an equivalent quantity of the sulfate salt of the following 5-epiaminoglycosides to the process of Example XIV-A.

1. 5-epigentamicin $C_1$,
2. 5-epigentamicin $C_{1a}$,
3. 5-epigentamicin $C_2$,
4. 5-epigentamicin $C_{2a}$,
5. 5-epigentamicin $C_{2b}$,
6. 5-epigentamicin $X_2$,
7. 5-epigentamicin A,
8. 5-epigentamicin B,
9. 5-epigentamicin $B_1$,
10. 5-epi-Antibiotic G-418,
11. 5-epi-Antibiotic 66-40B,
12. 5-epi-Antibiotic 66-40D,
13. 5-epi-Antibiotic JI-20A,
14. 5-epi-Antibiotic JI-20B,
15. 5-epi-Antibiotic G-52,
16. 5-epiverdamicin,
17. 5-epitobramycin.

Isolate and purify the respective resultant products in the manner described in Example XIV-A to obtain, respectively, 1. 1-N-acetyl-5-epigentamicin $C_1$,
2. 1-N-acetyl-5-epigentamicin $C_{1a}$,
3. 1-N-acetyl-5-epigentamicin $C_2$,
4. 1-N-acetyl-5-epigentamicin $C_{2a}$,
5. 1-N-acetyl-5-epigentamicin $C_{2b}$,
6. 1-N-acetyl-5-epigentamicin $X_2$,
7. 1-N-acetyl-5-epigentamicin A,
8. 1-N-acetyl-5-epigentamicin B,
9. 1-N-acetyl-5-epigentamicin $B_1$,
10. 1-N-acetyl-5-epi-Antibiotic G-418,
11. 1-N-acetyl-5-eip-Antibiotic 66-40B,
12. 1-N-acetyl-5-epi-Antibiotic 66-40D,
13. 1-N-acetyl-5-epi-Antibiotic JI-20A,
14. 1-N-acetyl-5-epi-Antibiotic JI-20B,
15. 1-N-acetyl-5-epi-Antibiotic G-52,
16. 1-N-acetyl-5-epiverdamicin,
17. 1-N-acetyl-5-epitobramycin.

C. In the procedures of Examples XIV-A and B buy substituting other acid anhydrides, e.g. propionic acid anhydride, N-octanoic acid anhydride, phenyl acetic acid anhydride and trans-β-phenylacrylic acid anhydride there is obtained the corresponding 1-N-acyl derivatives, e.g. 1-N-propionyl, 1-N-(n-octanoyl), 1-N-phenylacetyl and 1-N-(trans-β-phenylpropenoyl) of the 5-epi-4,6-di-O-(aminoglycosyl)-2-deoxystreptamine starting compounds listed therein, respectively.

D.
1-N-(5-Aminopentanoyl)-5-Epi-4,6-Di-O-(Aminoglycosyl)2-Deoxystreptamines 1. 1-N-(5-Aminopentanoyl)-5-Epigentamicin $C_1$ a. 1-N-(5-Phthalimidopentanoyl)-5-Epigentamicin $C_1$ Dissolve 2.5 g. of 5-epigentamicin $C_1$ sulfate in 250 ml. of water and add 100 ml. of methanol. Add 0.35 g. of triethylamine and stir for 10 minutes. Add a solution of 1.2 g. N-(5-phthalimidopentanoyloxy)succinimide in 20 ml. of dry dimethylformamide dropwise with stirring to the solution of the antibiotic. Stir the mixture at ambient temperature for 16 hours. Concentrate the reaction mixture to a residue in vacuo and triturate the residue with methanol to yield 3.4 g. of white solids. Chromatograph the residue on 200 g. of silica gel in the lower phase of a chloroform:methanol:7% ammonium hydroxide (2:1:1) system to give 1-N-(5-phthalimidopentanoyl)-5-epigentamicin $C_1$.

b. 1-N-(5-Aminopentanoyl)-5-Epigentamicin $C_1$

Heat 0.4 g. of 1-N-(5-phthalimidopentanoyl)gentamicin $C_1$ in 5 ml. of 5% ethanolic hydrazine hydrate under reflux for 4 hours. Concentrate the solution and add tetrahydrofuran to precipitate 1-N-(5-aminopentanoyl)-5-epigentamicin $C_1$ which is collected by filtration.

2. In similar manner treat an equivalent quantity of acid addition salt of the following 5-epiaminoglycosides to the process of Example XIV-D(1).
1. 5-epigentamicin $C_{1a}$,
2. 5-epigentamicin $C_2$,
3. 5-epigentamicin $C_{2a}$,
4. 5-epigentamicin $C_{2b}$,
5. 5-epigentamicin $X_2$,
6. 5-epigentamicin A,
7. 5-epigentamicin $B_1$,
8. 5-epiverdamicin,
9. 5-epitobramycin,
10. 5-episisomicin.

Isolate the resultant products in a manner similar to that described in Example XIV-D(1) to obtain the corresponding 1-N-(5-aminopentanoyl)-5-epiaminoglycoside derivative to obtain the 1-N-(5-aminopentanoyl) derivative of each of said 5-epiaminoglycoside starting compounds.

E.
1-N-(5-Hydroxypentanoyl)-5-Epi-4,6-Di-O-(Aminoglycosyl)-2-Deoxystreptamines 1. 1-N-(5-Hydroxypentanoyl)-5-Epigentamicin $C_1$ Dissolve 2.5 g. of 5-epigentamicin $C_1$ in 250 ml. of water and add 100 ml. of methanol. Add 0.35 g. of triethylamine and stir for fifteen minutes. Add a solution of 1.0 g. of N-(5-acetoxypentanoyloxy)succinimide with stirring to the solution of the antibiotic, and stir at ambient temperature for 16 hours. Evaporate the solution in vacuo to leave a solid residue. Dissolve the residue in 5 ml. of 5% ethanolic hydrazine hydrate and heat under reflux for 15 minutes. Concentrate the solution in vacuo to leave an oily residue and chromatograph it on 200 g. silica gel in the lower phase of a solvent system consisting of chloroform:methanol:7% ammonium hydroxide (2:1:1) to give 1-N-(5-hydroxypentanoyl)-5-epigentamicin $C_1$.

2. In similar manner, treat an equivalent quantity of the acid addition salt of those 5-epiaminoglycoside starting compounds set forth in Example XIV-D(2) to the procedure of above Example XIV-E(1). Isolate and purify the resultant products in a manner similar to that described in Example XIV-E(1) to obtain the following.
1. 1-N-(5-hydroxypentanoyl)-5-epigentamicin $C_{1a}$,
2. 1-N-(5-hydroxypentanoyl)-5-epigentamicin $C_2$,
3. 1-N-(5-hydroxypentanoyl)-5-epigentamicin $C_{2a}$,
4. 1-N-(5-hydroxypentanoyl)-5-epigentamicin $C_{2b}$,
5. a-N-(5-hydroxypentanoyl)-5-epigentamicin $X_2$,
6. 1-N-(5-hydroxypentanoyl)-5-epigentamicin A,
7. 1-N-(5-hydroxypentanoyl)-5-epigentamicin $B_1$,
8. 1-N-(5-hydroxypentanoyl)-5-epiverdamicin,
9. 1-N-(5-hydroxypentanoyl)-5-epitobramycin,
10. 1-N-(5-hydroxypentanoyl)-5-episisomicin.

F.
1-N-Formyl-5-Epi-4,6-Di-O-(Aminoglycosyl)-2-Deoxystreptamines 1. 1-N-Formyl-5-Epigentamicin $C_1$ Dissolve 2.5 gm. of 5-epigentamicin $C_1$ sulfate in 250 ml. of water and add 100 ml. of methanol. Add 0.35 g. of triethylamine and stir for 10 minutes. Add a solution of 2.0 gm. of N-formyloxysuccinimide in 20 ml. of dry dimethylformamide dropwise with stirring. Stir the reaction mixture at room temperature for 16 hours. Concentrate the reaction mixture in vacuo to a residue. Triturate the residue with methanol, filter and dry the resultant solid to obtain 1-N-formyl-5-epigentamicin $C_1$. (2) In similar manner treat an equivalent quantity of the acid addition salt of those 5-epiaminoglycoside starting compounds of Example XIV-D(2) to the process described in Example XIV-F(1). Isolate and purify the resultant products in a manner similar to that described to obtain the corresponding 1-N-formyl derivatives.

G.
1-N-(Aminohydroxyacyl)-5-epi-4,6-Di-O-(Aminoglycosyl)1,3-Diaminocyclitols (1) 1-N-(S-4-Amino-2-Hydroxybutyryl)-5-Epigentamicin $C_{1a}$ (a) 1-N-(S-4-Benzyloxycarbonylamino-2-Hydroxybutyryl)-5-Epigentamicin $C_{1a}$ Dissolve 2.8 g. (4 mmoles) of 5-epigentamicin $C_{1a}$ sulfate in 30 ml. of water and add 15 ml. of methanol. Add 0.56 ml. (4 mmoles) of triethylamine and stir for 10 minutes. Add a solution containing 4 mmoles of N-(S-4-benzyloxycarbonylamino-2-hydroxybutyryloxy)succinimide in 20 ml. of dry dimethylformamide dropwise with stirring to the antibiotic solution. Stir the mixture overnight (16 hours) at ambient temperature. Thin layer chromatography of the reaction mixture on silica gel using the lower phase of a solvent system consisting of chloroform:methanol:ammonium hydroxide (1:1:1), shows the presence of a plurality of minor components and one major component. Concentrate the reaction mixture to a residue in vacuo and triturate the residue with methanol to yield 3.2 g. of white solids containing all the components previously observed by chromatography.

Chromatograph 150 mg. of the product on 50 g. of silica gel using the lower phase of a solvent system consisting of chloroform:methanol:ammonium hydroxide (2:1:1). Pool the fractions containing the major component and lyophilize to give 1-N-(S-4-benzyloxycarbonylamino-2-hydroxybutyryl)-5-epigentamicin $C_{1a}$.

b. 1-N-(S-4-Amino-2-Hydroxybutyryl)-5-Epigentamicin $C_{1a}$

Dissolve the product of Example XIV-G(1a) in a mixture consisting of 12 ml. of methanol and 3 ml. of water, add 20 mg. of 10% palladium on carbon and hydrogenate at 4 atmospheres at room temperature. After 3 hours the reaction is essentially complete. Remove the catalyst by filtration and lyophilize the filtrate and obtain 46 mg. of 1-N-(S-4-amino-2-hydroxybutyryl)5-epigentamicin $C_{1a}$.

2. 1-N-(S-4-Amino-2-Hydroxybutyryl)-5-Epigentamicin B a. 1-N-(S-4-Benzyloxycarbonylamino-2-hydroxybutyryl)-5-epigentamicin B Dissolve 3.39 g. of 5-epigentamicin B sulfate in 48.4 ml. of water and dilute with 23.7 ml. of methanol. Add 0.7 ml. of triethylamine dropwise with stirring. Dissolve 1.67 g. of N-(S-4-benzyloxycarbonylamino-2-hydroxybutyryloxy)succinimide in dimethylformamide and add the solution dropwise with stirring to the antibiotic solution. Stir the resulting solution at room temperature for 18 hours, then concentrate to a residue in vacuo. Dissolve the residue in water and treat with dilute barium hydroxide solution with stirring until the pH reaches about 8.0. Remove the precipitated barium sulfate by filtration using a filter aid. Wash the precipitate with water, combine the filtrate and washings and concentrate to dryness in vacuo. Chromatograph the residue on a column containing 600 g. of silica gel using the lower phase of a solvent system consisting of chloroform:methanol:ammonium hydroxide (1:1:1) as the eluant. Combine the like fractions containing the 1-N-(S-4-benzyloxycarbonylamino-2-hydroxybutyryl)-5-epigentamicin B as determined by thin layer chromatography and concentrate the combined fractions to a residue comprising 1-N-(S-4-benzyloxycarbonylamino-2-hydroxybutyryl)-5-epigentamicin B.

b. 1-N-(S-4-Amino-2-Hydroxybutyryl)-5-Epigentamicin B

Dissolve the product of above Example XIV-G(2a) in a mixture consisting of 20 ml. of water and 8 ml. of methanol. Hydrogenate the product in the presence of 60 mg. of 5% palladium-on-carbon at 3.5 atmospheres and room temperature for 3 hours. Remove the catalyst by filtration through a filter aid. Wash the filter pad with water and combine the filtrate and washings. Concentrate the combined filtrate and washings to dryness in vacuo. Chromatograph the residue on a silica gel column containing 100 g. of silica gel using a solution consisting of chloroform:methanol:ammonium hydroxide (1:2:1) as the eluant. Fractions containing the most polar component are pooled, concentrated and lyophilized to give 1-N-(S-4-amino-2-hydroxybutyryl)-5-epigentamicin B.

3. 1-N-(S-4-Amino-2-Hydroxybutyryl)-5-Epiverdamicin a. 1-N-(S-4-Phthalimido-2-Hydroxybutyryl)-5-Epiverdamicin Dissolve 5.00 g. of 5-epiverdamicin sulfate in 50 ml. of water and add 25 ml. of methanol. Add 0.50 ml. of triethylamine and stir for 10 minutes. Add a solution containing 2.5 g. of N-(S-4-phthalimido-2-hydroxybutyryloxy)succinimide in 10 ml. of dimethylformamide dropwise with stirring. Stir the mixture overnight at ambient temperature then concentrate to a residue in vacuo. Chromatograph the residue over 160 g. of silica gel, eluting with the lower phase of a chloroform:methanol:concentrated ammonium hydroxide (1:1:1) solvent mixture. Combine and evaporate fractions containing the major component of the reaction (determined by TLC on silica gel plates) and obtain thereby the compound of this example as a white amorphous solid.

b. 1-N-(S-4-Amino-2-Hydroxybutyryl)-5-Epiverdamicin

Dissolve the product of Example XIV-G(3a) in 40 ml. of ethanol and add 0.2 g. of hydrazine hydrate. Reflux the solution for 3 hours, then evaporate to dryness in vacuo. Chromatograph the residue over 160 g. of silica gel, eluting with the lower phase of a chloroform:methanol:concentrated ammonium hydroxide (1:1:1) solvent mixture. Combine and evaporate fractions containing the major component of the reaction (determined by TLC on silica gel plates) and obtain thereby the compound of this example as a white amorphous solid. (4) In the procedures of Examples XIV-G(1-3) the sulfate salts of other 5-epi-4,6-di-O-(aminoglycosyl)-1,3-diaminocyclitols may be substituted for 5-epigentamicin $C_{1a}$, 5-epigentamicin B and 5-epiverdamicin, and other N-(S-benzyloxycarbonylaminohydroxyacyloxy)succinimides may be substituted for N-(S-4-benzyloxycarbonylamino-2-hydroxybutyryloxy)succinimide or N-(S-4-phthalimide-2-hydroxybutyryloxy)succinimide, and there will be obtained the corresponding 1-N-aminohydroxyacyl)-5-epi-4,6-di-O-(aminoglycosyl)-1,3-diaminocyclitols.

EXAMPLE XV

1-N-ALKYL-5-EPI-4,6-DI-O-(AMINOGLYCOSYL)-1,3-DI-AMINOCYCLITOLS PREPARED BY HYDRIDE REDUCTION OF THE CORRESPONDING 1-N-ACYL DERIVATIVES

A.

1-N-(S-δ-Amino-β-Hydroxyalkyl)-5-Epiaminoglycosides 1. 1-N-(S-δ-Amino-β-Hydroxybutyl)-5-Epigentamicin $C_1$ Suspend 98 mg. of 1-N-(S-4-amino-2-hydroxybutyryl)-5-epigentamicin $C_1$ in 8 ml. of tetrahydrofuran. Add 14 ml. of 1 M diborane in tetrahydrofuran and heat at reflux temperature for 6 hours under an atmosphere of nitrogen. Carefully add 2 ml. of water to decompose any excess diborane and evaporate. Dissolve the resultant residue in hydrazine hydrate and heat at reflux temperature under an atmosphere of nitrogen for 16 hours. Evaporate the solution and extract the residue with hot aqueous ethanol. Evaporate the combined ethanol extracts and chromatograph the resultant residue over 10 ml. of silica gel eluting with the lower phase of a chloroform:methanol:concentrated ammonium hydroxide (2:1:1) solvent system. Combine and evaporate the like fractions as determined by thin layer chromatography to obtain 1-N-(S-δ-amino-β-hydroxybutyl)-5-epigentamicin $C_1$.

2. In the above procedure, substitute 1-N-(S-3-amino-2-hydroxypropionyl)-5-epigentamicin $C_1$ for 1-N-(S-4-amino-2-hydroxybutyryl)-5-epigentamicin $C_1$ to obtain 1-N-(S- δ-amino-β-hydroxypropyl)-5-epigentamicin $C_1$.

3. Treat each of the following 1-N-(S-4-amino-2-hydroxybutyryl)-5-epi-4,6-di-O-(aminoglycosyl)-1,3-diaminocyclitols with diborane in tetrahydrofuran in the manner described in Example XV-A(1).

1. 1-N-(S-4-amino-2-hydroxybutyry)-5-epigentamicin A,
2. 1-N-(S-4-amino-2-hydroxybutyryl)-5-epigentamicin B,
3. 1-N-(S-4-amino-2-hydroxybutyryl)-5-epigentamicin $B_1$,
4. 1-N-(S-4amino-2-hydroxybutyryl)-5-epigentamicin $C_{1a}$,
5. 1-N-(S-4-amino-2-hydroxybutyryl)-5-epigentamicin $C_2$,
6. 1-N-(S-4-amino-2-hydroxybutyryl)-5-epigentamicin $C_{2a}$,
7. 1-N-(S-4-amino-2-hydroxybutyryl)-5-epigentamicin $C_{2b}$,
8. 1-N-(S-4-amino-2-hydroxybutyryl)-5-epigentamicin $X_2$,
9. 1-N-(S-4-amino- b 2-hydroxybutyryl)-5-epitobramycin,
10. 1-N-(S-4-amino-2-hydroxybutyryl)-5-epi-Antibiotic G-418,
11. 1-N-(S-4-amino-2-hydroxybutyryl)-5-epi-Antibiotic JI-20A,
12. 1-N-(S-4-amino-2-hydroxybutyryl)-5-epi-Antibiotic JI-20B.

Isolate and purify each of the resultant products in a manner similar to that described in Example XV-A(1) to obtain, respectively, 1. 1-N-(S-δ-amino-βhydroxybutyl)-5-epigentamicin A,
2. 1-N-(S-δ-amino-β-hydroxybutyl)-5-epigentamicin B,
3. 1-N-(S-δ-amino-β-hydroxybutyl)-5-epigentamicin $B_1$,
4. 1-N-(S-δ-amino-β-hydroxybutyl)-5-epigentamicin $C_{1a}$,
5. 1-N-(S-δ-amino-β-hydroxybutyl)-5-epigentamicin $C_2$,
6. 1-N-(S-δ-amino-β-hydroxybutyl)-5-epigentamicin $C_{2a}$,
7. 1-N-(S-δ-amino-β-hydroxybutyl)-5-epigentamicin $C_{2b}$,
8. 1-N-(S-δ-amino-β-hydroxybutyl)-5-epigentamicin $X_2$,
9. 1-N-(S-δ-amino-β-hydroxybutyl)-5-epitobramycin,
10. 1-N-(S-δ-amino-β-hydroxybutyl)-5-epi-Antibiotic G-418,
11. 1-N-(S-δ-amino-β-hydroxybutyl)-5-epi-Antibiotic JI-20A,
12. 1-N-(S-δ-amino-β-hydroxybutyl)-5-epi-Antibiotic JI-20B.

4. In the procedure of Example XV-A(2) hereinabove utilize as starting compounds the corresponding 1-N-(S-3-amino-2-hydroxypropionyl) derivatives to obtain the corresponding 1-N-(S-δ-amino-β-hydroxypropyl) derivatives, i.e.

1. 1-N-(S-γ-amino-β-hydroxypropyl)-5-epigentamicin A,
2. 1-N-(S-γ-amino-β-hydroxypropyl)-5-epigentamicin B,
3. 1-N-(S-γ-amino-β-hydroxypropyl)-5-epigentamicin $B_1$,
4. 1-N-(S-γ-amino-β-hydroxypropyl)-5-epigentamicin $C_{1a}$,
5. 1-N-(S-γ-amino-β-hydroxypropyl)-5-epigentamicin $C_2$,
6. 1-N-(S-γ-amino-β-hydroxypropyl)-5-epigentamicin $C_{2a}$,
7. 1-N-(S-γ-amino-β-hydroxypropyl)-5-epigentamicin $C_{2b}$,
8. 1-N-(S-γ-amino-β-hydroxypropyl)-5-epigentamicin $X_2$,
9. 1-N-(S-γ-amino-β-hydroxypropyl)-5-epigentamicin,
10. 1-N-(S-γ-amino-β-hydroxypropyl)-5-epi-Antibiotic G-418,
11. 1-N-(S-γ-amino-β-hydroxypropyl)-5-epi-Antibiotic JI-20A,
12. 1-N-(S-γ-amino-β-hydroxypropyl)-5-epi-Antibiotic JI-20B.

B. 1-N-Alkyl-5-Epiaminoglycosides 1. 1-N-Ethyl-5-Epigentamicin $C_1$

In a manner similar to that described in Example XV-A(1) treat 1-N-acetyl-5-epigentamicin $C_1$ with diborane in tetrahydrofuran. Isolate and purify the resultant products in a manner similar to that described in Example XV-A(1) to obtain 1-N-ethyl-5-eipgentamicin $C_1$.

2. Treat the following 1-N-acetyl-5-epi-4,6-di-O-(aminoglycosyl)-1,3-diaminocyclitols in the manner of above Example XV-B(1).

1. 1-N-acetyl-5-epigentamicin A,
2. 1-N-acetyl-5-epigentamicin B,
3. 1-N-acetyl-5-epigentamicin $B_1$,
4. 1-N-acetyl-5-epigentamicin $C_{1a}$,
5. 1-N-acetyl-5-epigentamicin $C_2$,
6. 1-N-acetyl-5-epigentamicin $C_{2a}$,
7. 1-N-acetyl-5-epigentamicin $C_{2b}$,
8. 1-N-acetyl-5-epigentamicin $X_2$,
9. 1-N-acetyl-5-epitobramycin,
10. 1-N-acetyl-5-epi-Antibiotic G-418,
11. 1-N-acetyl-5-epi-Antibiotic JI-20A,
12. 1-N-acetyl-5-epi-Antibiotic JI-20B.

Isolate and purify each of the resultant products in the manner similar to that described to obtain, respectively, 1. 1-N-ethyl-5-epigentamicin A,
2. 1-N-ethyl-5-epigentamicin B,
3. 1-N-ethyl-5-epigentamicin $B_1$,
4. 1-N-ethyl-5-epigentamicin $C_{1a}$,
5. 1-N-ethyl-5-epigentamicin $C_2$,
6. 1-N-ethyl-5-epigentamicin $C_{2a}$,
7. 1-N-ethyl-5-epigentamicin $C_{2b}$,
8. 1-N-ethyl-5-epigentamicin $X_2$,
9. 1-N-ethyl-5-epitobramycin,
10. 1-N-ethyl-5-epi-Antibiotic G-418,
11. 1-N-ethyl-5-epi-Antibiotic JI-20A,
12. 1-N-ethyl-5-epi-Antibiotic JI-20B.

3. 1-N-Ethyl-5-Episisomicin

Suspend 1 gm. of 1-N-acetyl-5-episisomicin in 100 ml. of tetrahydrofuran. Add 1 gm. of lithium aluminum hydride, then sir the resultant suspension at reflux temperature for 24 hours under an atmosphere of nitrogen. Cool and decompose the excess hydride by careful addition of ethyl acetate. Evaporate the reaction mixture to a small volume and dilute with water. Separate the insoluble solids by filtration and wash well with acetic acid. Evaporate the combined filtrate and washings and dissolve the resultant residue in water. Adjust the pH of the aqueous solution to about 7 by addition of ammonium hydroxide. Pass the solution through a column of IRC-50 resin in the ammonium cycle and wash the column well with water. Elute with 0.5 N ammonium hydroxide, evaporate the eluate, and chromatograph the resultant residue over 20 gm. of silica gel eluting with the lower phase of a 2:1:1 chloroform:methanol:concentrated ammonium hydroxide solvent system. Combine and evaporate the like fractions as determined by thin layer chromatography to obtain 1-N-ethyl-5-episisomicin.

4. Treat the following 5-epi-4,6-di-O-(aminoglycosyl)-1,3-diaminocyclitols in the manner described in the procedure of Example XV-B(3).

1. 1-N-acetyl-5-epiverdamicin,
2. 1-N-acetyl-5-acetyl-5-epi-Antibiotic 66-40B,
3. 1-N-acetyl-5-epi-Antibiotic 66-40D,
4. 1-N-acetyl-5-epi-Antibiotic G-52.

Isolate and purify each of the resultant products to obtain, respectively, 1. 1-N-ethyl-5-epiverdamicin,
2. 1-N-ethyl-5-epi-Antibiotic 66-40B,
3. 1-N-ethyl-5-epi-Antibiotic 66-40D,
4. 1-N-ethyl-5-epi-Antibiotic G-52.

EXAMPLE XVI

PREPARATION OF 1-N-ALKYL-4,6-DI-O-(AMINOGLYCOSYL)-1,3-DIAMINOCYCLITOLS VIA REACTION OF THE SULFATE SALT OF THE CORRESPONDING 1-N-UNSUBSTITUTED COMPOUND WITH AN ALDEHYDE FOLLOWED BY SODIUM CYANOBOROHYDRIDE

A. 1-N-Ethylsisomicin

To a solution of 5 gm. of sisomicin in 250 ml. of water add 1 N sulfuric acid until the pH of the solution is adjusted to about 5. To the solution of sisomicin sulfuric acid addition salt thereby formed, add 2 ml. of acetaldehyde, stir for 10 minutes, then add 0.85 gm. of sodium cyanoborohydride. Continue stirring at room temperature for 15 minutes, then concentrate solution in vacuo to a volume of about 100 ml., treat the solution with a basic ion exchange resin (e.g. Amberlite IRA 401S (OH$^-$)), then lyophilize to a residue comprising 1-N-ethylsisomicin.

Purify by chromatographing on 200 gm. of silica gel, eluting with lower phase of a chloroform-methanol-7% aqueous ammonium hydroxide (2:1:1) system. Combine the like eluates as determined by thin layer chromatography and concentrate the combined eluates of the major component in vacuo to a residue comprising 1-N-ethylsisomicin (yield 1.25 gm.). Further purify by again chromatographing on 100 gm. of silica gel eluting with a chloroform-methanol-3.5% ammonium hydroxide (1:2:1) system. Pass the combined, like eluates (as determined by thin layer chromatography) through a column of basic ion exchange resin and lyophilize the eluate to obtain 1-N-ethylsisomicin (yield 0.54 gm.); $[\alpha]_D^{26} + 164°$ (0.3%, $H_2O$); pmr (ppm) ($D_2O$): $\delta$ 1.05 (3H, t, J=7Hz, —$CH_2CH_3$); 1.19 (3H, s, —C—$CH_3$); 2.5 (3H, s, N—$CH_3$); 4.85 (1H, m, =$CH$—); 4.95 (1H, d, J=4Hz, $H_1''$); 5.33 (1H, d, J=2.5 Hz, $H_1'$).

Mass Spectrum: (M+1)$^+$m/e 476 also m/e 127, 154, 160, 173, 191, 201, 219, 256, 299, 317, 332, 345, 350, 360, 378, 390, 400.

B. In the procedure of Example XVI-A, by substituting for sisomicin equivalent quantities of each of the 5-epiaminoglycosides prepared as described in Example XI-B and C to obtain, respectively, 1. 1-N-ethyl-5-epigentamicin $C_1$,
2. 1-N-ethyl-5-epigentamicin $C_2$,
3. 1-N-ethyl-5-epigentamicin $C_{2a}$,
4. 1-N-ethyl-5-epigentamicin $C_{2b}$,
5. 1-N-ethyl-5-epi-Antibiotic G-52,
6. 1-N-ethyl-5-epiverdamicin,
7. 1-N-ethyl-5-episisomicin,
8. 1-N-ethyl-5-epi-Antibiotic 66-40D,
9. 1-N-ethyl-5-epigentamicin A,
10. 1-N-ethyl-5-epigentamicin B,
11. 1-N-ethyl-5-epigentamicin $B_1$,
12. 1-N-ethyl-5-epigentamicin $X_2$,
13. 1-N-ethyl-5-epi-Antibiotic G-418,
14. 1-N-ethyl-5-epi-Antibiotic JI-20A,
15. 1-N-ethyl-5-epi-Antibiotic JI-20B,
16. 1-N-ethyl-5-epikanamycin B,
17. 1-N-ethyl-5-epitobramycin,
18. 1-N-ethyl-5-epikanamycin A,
19. 1-N-ethyl-5-epi-3',4'-dideoxykanamycin B.

C. In the precedures of Examples XVI-A and B by substituting for acetaldehyde equivalent quantities of other aldehydes, e.g. propenal, butanal and $\delta$-acetamidobutanal, there is obtained the corresponding 1-N-propyl, 1-N-butyl and 1-N-$\delta$-acetamidobutyl derivatives of the 5-epiaminoglycosides listed therein. Treatment of the 1-N-($\delta$-acetamidobutyl) derivative with base yields the corresponding 1-N-($\delta$-aminobutyl) derivative.

EXAMPLE XVII

ACID ADDITION SALTS

A. Sulfate Salts (Sulfuric acid addition salts)

Dissolve 5.0 gm. of 5-epigentamicin $C_1$ in 25 ml. of water and adjust the pH of the solution to 4.5 with 1 N sulfuric acid. Pour into about 300 ml. of methanol with vigorous agitation, continue the agitation for about 10-20 minutes and filter. Wash the precipitate with methanol and dry at about 60° C in vacuo to obtain 5-epigentamicin $C_1$ sulfate.

In like manner, the sulfate salt of the compounds of Examples VIII to XVI are prepared.

B. Hydrochloride Salts

Dissolve 5.0 gm. of 5-epigentamicin $C_{1a}$ in 25 ml. of water. Acidify with 2 N hydrochloric acid to pH 5. Lyophilize to obtain 5-epigentamicin $C_{1a}$ hydrochloride.

In like manner, the hydrochloride salt of the compounds of Examples VIII to XVI are prepared.

The present invention includes within its scope pharmaceutical compositions comprising my novel 5-epi-4,6-di-O-(aminoglycosyl)-2-deoxystreptamines with a compatible, pharmaceutically acceptable carrier or coating. Also included within my invention is the method of eliciting an antibacterial response in a warm-blooded animal having a susceptible bacterial infection which comprises administering to said animal a non-toxic, antibacterially effective amount of a member selected from the group consisting of a 5-epigentamicin A, 5-epigentamicin B, 5-epigentamicin $B_1$, 5-epigentamicin $C_1$, 5-epigentamicin $C_{1a}$, 5-epigentamicin $C_2$, 5-epigentamicin $C_{2a}$, 5-epigentamicin $C_{2b}$, 5-epigentamicin $X_2$, 5-epiverdamicin, 5-epitobramycin, 5-epi-Antibiotic G-418, 5-epi-Antibiotic 66-40B, 5-epi-Antibiotic 66-40D, 5-epi-Antibiotic JI-20A, 5-epi-Antibiotic JI-20B, 5-epi-Antibiotic G-52, 5-epikanamycin A, 5-epikanamycin B, 5-epi-3',4'-dideoxykanamycin B, and the 1-N-K derivatives of the foregoing, wherein K is as hereinabove defined and the non-toxic pharmaceutically acceptable acid addition salts thereof.

As discussed hereinabove, the 5-epi-4,6-di-O-(aminoglycosyl)-2-deoxystreptamines of this invention such as defined by formulae I, II, III and IV, their 1-N-alkyl derivatives and the non-toxic, pharmaceutically acceptable acid addition salts thereof are broad spectrum antibacterial agents which, advantageously, exhibit activity against organisms which are resistant to their 5-hydroxy precursors. Thus, the 5-epi-compounds of this invention can be used alone or in combination with other antibiotic agents to prevent the growth or reduce the number of bacteria in various environments. They may be used, for example, to disinfect laboratory glassware, dental and medical equipment contaminated with *Staphylococcus aureus* or other bacteria inhibited by the 5-epi- derivatives of this invention. The activity of the 5-epi-4,6-di-O-(aminoglycosyl)-2-deoxystreptamines against gram negative bacteria renders them useful for combating infections caused by gram negative organisms, e.g. species of Proteus and Pseudomonas. My 5-eip-4,6-di-O-(aminoglycosyl)-2-deoxystreptamines, e.g. 5-epigentamicin $C_1$ and 5-epigentamicin $C_{1a}$ have veterinary applications, particularly in the treatment of mastitis in cattle and Salmonella induced diarrhea in domestic animals such as the dog and the cat.

In general, the dosage administered of the 5-epi-4,6-di-O-(aminoglycosyl)-2-deoxystreptamines will be dependent upon the age and weight of the animal species being treated, the mode of administration, and the type and severity of bacterial infection being prevented or reduced. In general, the dosage of 5-epi-4,6-di-O-(aminoglycosyl)-2-deoxystreptamines employed to combat a given bacterial infection will be similar to the dosage requirements of the corresponding 4,6-di-O-(aminoglycosyl)-2-deoxystreptamines. Additionally, many of the 5-epi-4,6-di-O-(aminoglycosyl)-2-deoxystreptamines of formula I are also advantageously cidal against certain gram negative organisms which are resistant to the 5-hydroxy precursors.

The 5-epi-4,6-di-O-(aminoglycosyl)-2-deoxystreptamines of formulae I, II, III and IV and their 1-N-alkyl devivatives and the pharmaceutically acceptable acid addition salts thereof may be administered orally. They may also be applied topically in the form of ointments, both hydrophilic and hydrophobic, in the form of lotions which may be aqueous, non-aqueous or of the emulsion type or in the form of creams. Pharmaceutical carriers useful in the preparation of such formulations will include, for example, such substances as water, oils, greases, polyesters, polyols and the like.

For oral administration the 5-epi-4,6-di-O-(aminoglycosyl)-2-deoxystreptamine antibacterials of this invention may be compounded in the form of tablets, capsules, elixirs or the like or may even be admixed with animal feed. It is in these dosage forms that the antibacterials are most effective for treating bacterial infections of the gastrointestinal tract, which infections cause diarrhea.

In general, the topical preparations will contain from about 0.1 to about 3.0 gms. of 5-epi-4,6-di-O-(aminoglycosyl)-2-deoxystreptamine of formulae I, II, III and IV and their 1-N-alkyl derivatives per 100 gms. of ointment, creams or lotion. The topical preparations are usually applied gently to lesions from about 2 to about 5 times a day.

The antibacterials of this invention may be utilized in liquid form such as solutions, suspensions and the like for otic and optic use and may also be administered parenterally via intramuscular injection. The injectable solution or suspension will usually be administered at from about 1 mg. to about 10 mgs. of antibacterial per kilogram of body weight per day divided into about 2 to about 4 doses. The precise dose depends on the stage and severity of the infection, the susceptibility of the infecting organism to the antibacterial and the individual characteristics of the animal species being treated.

The following formulations are to exemplify some of the dosage forms in which the antibacterial agents of this invention and their derivatives may be employed:

| Tablet | Formulation 1 | | |
|---|---|---|---|
| | 10 mg. Tab. | 25 mg. Tab. | 100 mg. Tab. |
| 5-epigentamicin $C_1$ | 10.5 * mg. | 26.25 * mg. | 105.0 * mg. |
| Lactose, impalpable powder | 197.50 mg. | 171.25 mg. | 126.00 mg. |
| Corn Starch | 25.00 mg. | 25.00 mg. | 35.00 mg. |

| Tablet | -continued Formulation 1 | | |
|---|---|---|---|
| | 10 mg. Tab. | 25 mg. Tab. | 100 mg. Tab. |
| Polyvinylpyrrolidone | 7.50 mg. | 7.50 mg. | 7.50 mg. |
| Magnesium Stearate | 2.50 mg. | 2.50 mg. | 3.50 mg. |
| *5% excess | | | |

Procedure

Prepare a slurry consisting of the 5-epigentamicin $C_1$ lactose and polyvinylpyrrolidone. Spray dry the slurry. Add the corn starch and magnesium stearate. Mix and compress into tablets.

| Formulation 2 | |
|---|---|
| Ointment | |
| 5-epi-5-deoxygentamicin $C_{1a}$ | 1.9 gm. |
| Methylparaben U.S.P. | 0.5 gm. |
| Propyl paraben U.S.P. | 0.1 gm. |
| Petrolatum | to 1000 gm. |

Procedure

1. Melt the petrolatum.
2. Mix the 5-epigentamicin $C_{1a}$, methylparaben and propylparaben with about 10% of the molten petrolatum.
3. Pass the mixture through a colloid mill.
4. Add the remainder of the petrolatum with agitation and cool the mixture until it becomes semi-solid. At this stage the product may be put into suitable containers.

Ointments of 5-epi-4,6-di-O-(aminoglycosyl)-2-deoxystreptamines of formulae I, II, III and IV, their 1-N-alkyl derivatives, and the acid addition salts thereof, are prepared by substituting an equivalent quantity of 5-epi-4,6-di-O-(aminoglycosyl)-2-deoxystreptamine or an acid addition salt thereof, for 5-epi-5-deoxygentamicin $C_{1a}$ in the foregoing example and by following substantially the procedure of the example.

| Injectable Solution | Formulation 3 | |
|---|---|---|
| | Per 2.0 ml. vial* | Per 50 Liters |
| 5-epigentamicin $C_1$ sulfate | 84 * mgs. | 2100 * gms. |
| Methyl paraben, U.S.P. | 3.6 mgs. | 90.0 gms. |
| Propyl paraben, U.S.P. | 0.4 mgs. | 10.0 gms. |
| Sodium bisulfite, U.S.P. | 6.4 mgs. | 160.0 gms. |
| Disodium Ethylenediamine tetraacetate dihydrate, R.G. | 0.2 mgs. | 5.0 gms. |
| Water, U.S.P. q.s. | 2.0 ml. | 50.0 liters |

*Includes a 5% manufacturing overcharge

Procedure: For a 50.0 liter batch

Charge approximately 35 liters of water for injection to a suitble stainless steel jacketed vessel and het to about 70° C. Charge the methyl paraben and propyl paraben to the heated water for injection and dissolve with agitation. When the parabens are completely dissolved, cool the contents of the tank to 25°–30° C by circulating cold water through the tank jacket. Sparge the solution with nitrogen gas for at least 10 minutes and keep covered with nitrogen during subsequent processing. Charge and dissolve the disodium EDTA and sodium bisulfite. Charge and dissolve the 5-epigentamicin C₁ sulfate. Bring the batch volume up to 50.0 liters with water for injection and agitate until homogeneous.

Under sterile conditions, filter the solution through a suitble bacteria retentive filter collecting the filtrate in a filling tank.

Fill the filtrate aseptically into sterile pyrogen-free multiple dose vials, stopper and seal.

In like manner, injectable solutions of other 5-epi-4,6-di-O-(aminoglycosyl)-2-deoxystreptamines and especially acid addition salts of such antibacterial agents, may be prepared by substituting an equivalent quantity of such compounds for 5-epigentamicin C$_{1a}$ sulfate and by following the procedure set forth above.

I claim:

1. A compound selected from the group consisting of a 5-epi-4,6-di-O-(aminoglycosyl)-2-deoxystreptamine selected from the group consisting of 5-epigentamicin A, 5-epigentamicin B, 5-epigentamicin B₁, 5-epigentamicin C₁, 5-epigentamicin C$_{1a}$, 5-epigentamicin C₂, 5-epigentamicin C$_{2a}$, 5-epigentamicin C$_{2b}$, 5-epigentamicin X₂, 5-epitobramycin, 5-epiverdamicin, 5-epikanamycin A, 5-epikanamycin B, 5-epi-3',4'-dideoxykanamycin B, 5-epi-Antibiotic G-52, 5-epi-Antibiotic 66-40B, 5-epi-Antibiotic 66-40D, 5-epi-Antibiotic G-418, 5-epi-Antibiotic JI-20A, 5-epi-Antibiotic JI-20B;

the 1-N-K-derivatives of the foregoing, wherein K is an alkyl substituent selected from the group consisting of alkyl, alkyl cycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; and the pharmaceutically acceptable acid addition salts thereof.

2. A compound of claim 1 wherein said 5-epi-4,6-di-O-(aminoglycosyl)-2-deoxystreptamine is a 5-epi-4-O-aminoglycosyl-6-O-garosaminyl-2-deoxystreptamine.

3. A compound of claim 2 which is 5-epigentamicin B.

4. A compound of claim 2 which is 5-epigentamicin B₁.

5. A compound of claim 2 which is 5-epigentamicin C₁.

6. A compound of claim 2 which is 5-epigentamicin C$_{1a}$.

7. A compound of claim 2 which is 5-epigentamicin C₂.

8. A compound of claim 2 which is 5-epigentamicin C$_{2a}$.

9. A compound of claim 2 which is 5-epigentamicin C$_{2b}$.

10. A compound of claim 2 which is 5-epigentamicin X₂.

11. A compound of claim 2 which is 5-epiverdamicin.

12. A compound of claim 2 which is 5-epi-Antibiotic G-52.

13. A compound of claim 2 which is 5-epi-Antibiotic G-418.

14. A compound of claim 2 which is 5-epi-Antibiotic JI-20A.

15. A compound of claim 2 which is 5-epi-Antibiotic JI-20B.

16. A compound of claim 1 which is 5-epi-Antibiotic 66-40D.

17. A 1-N-K derivative of claim 1 wherein K is an alkyl substituent having up to 4 carbon atoms.

18. A 1-N-K derivative of claim 1 wherein K is ethyl.

19. A compound selected from the group consisting of a 1-N-acyl derivative of a 5-epi-4,6-di-O-(aminoglycosyl)-2-deoxystreptamine selected from the group consisting of 5-epigentamicin A, 5-epigentamicin B, 5-epigentamicin B₁, 5-epigentamicin C₁, 5-epigentamicin C$_{1a}$, 5-eipgentamicin C₂, 5-epigentamicin C$_{2a}$, 5-epigentamicin C$_{2b}$, 5-epigentamicin X₂, 5-epitobramycin, 5-epiverdamicin, 5-epikanamycin A, 5-epikanamycin B, 5-epi-3',4'-dideoxykanamycin B, 5-epi-Antibiotic G-52, 5-epi-Antibiotic 66-40B, 5-epi-Antibiotic 66-40D, 5-epi-Antibiotic G-418, 5-epi-Antibiotic JI-20A, 5-epi-Antibiotic JI-20B;

wherein said acyl is

with K' being hydrogen or an alkyl substituent selected from the group consisting of alkyl, cycloalkyl, alkenyl, aralkyl, hydroxyalkyl, aminoalkyl, alkylaminoalkyl, aminohydroxyalkyl, and alkylaminohydroxyalkyl, said alkyl substituent having up to 7 carbon atoms, and when said alkyl substituent is substituted by both hydroxyl and amino functions, only one of said functions can be attached at any one carbon atom;

and the acid addition salts thereof.

20. A compound of claim 19 wherein said 1-N-acyl is 1-N-acetyl.

21. The process for preparing a 5-epi-4,6-di-O-(aminoglycosyl)-2-deoxystreptamine selected from the group consisting of 5-epigentamicin A, 5-epigentamicin B, 5-epigentamicin B₁, 5-epigentamicin C₁, 5-epigentamicin C$_{1a}$, 5-epigentamicin C₂, 5-epigentamicin C$_{2a}$, 5-epigentamicin C$_{2b}$, 5-epigentamicin X₂, 5-epitobramycin, 5-episisomicin, 5-epiverdamicin, 5-epikanamycin A, 5-epikanamycin B, 5-epi-3',4'-dideoxykanamycin B, 5-epi-Antibiotic G-52, 5-epi-Antibiotic 66-40B, 5-epi-Antibiotic 66-40D, 5-epi-Antibiotic G-418, 5-epi-Antibiotic JI-20A, 5-epi-Antibiotic JI-20B;

and the 1-N-K derivatives thereof, wherein K is an alkyl substituent selected from the group consisting of alkyl, alkyl cycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom;

which comprises the reaction of the corresponding 5-O-R-4,6-di-O-(aminoglycosyl)-2-deoxystreptamine wherein R is a hydrocarbonsulfonyl or a halogeno derivative thereof, said hydrocarbon having up to 8 carbon atoms, or a nitrobenzenesulfonyl; and wherein all other hydroxyl functions and all amino functions are protected by groups susceptible to reductive cleavage or to basic or mild acid hydrolysis; with dimethylformamide at temperatures in the range of from about 80° C to about 155° C;

followed by removal of the protecting groups in the resulting N-protected-O-protected intermediate with aqueous base or, when protecting groups susceptible to reductive cleavage are present, by reaction of said resulting intermediate with hydrogen in the presence of a catalyst or with an alkali metal in liquid ammonia, followed by treatment with aqueous base; thence, when any of said protecting groups are acetals or ketals, reaction of the resulting O-protected intermediate with aqueous acid.

22. The process of claim 21 wherein R is methanesulfonyl.

23. The process of claim 21 when carried out in the presence of a tetraalkylammonium alkanoate.

24. The process of claim 21 when carried out in the presence of tetra-n-butylammonium acetate.

25. The process for preparing a 5-epi-4,6-di-O-(aminoglycosyl)-2-deoxystreptamine selected from the group consisting of 5-epigentamicin A, 5-epigentamicin B, 5-epigentamicin $B_1$, 5-epigentamicin $C_1$, 5-epigentamicin $C_{1a}$, 5-epigentamicin $C_2$, 5-epigentamicin $C_{2a}$, 5-epigentamicin $C_{2b}$, 5-epigentamicin $X_2$, 5-epitobramycin, 5-epiverdamicin, 5-episisomicin, 5-epikanamycin A, 5-epi-3',4'-dideoxykanamycin B, 5-epi-Antibiotic G-52, 5-epi-Antibiotic 66-40B, 5-epi-Antibiotic 66-40D, 5-epi-Antibiotic G-418, 5-epi-Antibiotic JI-20A, 5-epi-Antibiotic JI-20B;

and the 1-N-K-derivatives of the foregoing, wherein K is an alkyl substituent selected from the group consisting of alkyl, alkyl cycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent ajacent to the aminoglycoside nitrogen being unsubstituted, and when said alkyl substituent is substituted by both hydroxyl and amino functions, only one of said functions can be attached at any one carbon atom;

which comprises the reaction of the corresponding 4,6-di-O-(aminoglycosyl)-2-deoxystreptamine wherein the amino functions and hydroxyl functions other than the 5-hydroxyl function are protected by groups susceptible to reductive cleavage or to basic or mild acid hydrolysis, with an oxidizing agent selected from the group consisting of ruthenium tetroxide, chromic acid in acetone, or chromium trioxide-pyridine complex in methylene chloride;

the reaction of the resulting N-protected-O-protected-5-dehydro-4,6-di-O-(aminoglycosyl)-2-deoxystreptamine with an alkali metal borohydride;

followed by removal of the protecting groups by treatment of the thereby produced N-protected-O-protected-5-epi-4,6-di-O-(aminoglycosyl)-2-deoxystreptamine with aqueous base or, when protecting groups susceptible to reductive cleavage are present, by treatment with a reducing agent selected from the group consisting of hydrogen in the presence of a catalyst and an alkali metal in liquid ammonia, followed by treatment with base; thence, when any of said protecting groups are ketals or acetals, treatment of the resulting O-protected intermediate with aqueous acid.

26. The process of claim 25 wherein said alkali metal borohydride is lithium tri-secondary butyl borohydride.

27. A 5-dehydro-4,6-di-O-(aminoglycosyl)-2-deoxystreptamine selected from the group consisting of:

1,3,2',3''-tetra-N-Y-3',2'',4'''-tri-O-Z-4',6'-O-W-5-dehydrogentamicin A, 1,3-di-N-Y-2',3'-O-W-6',4'; 3'', 4''-di-N,O-carbonyl-2''-O-Z-5-dehydrogentamicin B, 1,3-di-N-Y-2',3'-O-W-6',4';3'',4''-di-N,O-carbonyl-2''-O-Z-5-dehydrogentamicin $B_1$, 1,3,2',6'-tetra-N-Y-2''-O-Z-3'',4''-N,O-carbonyl-5-dehydrogentamicin $C_1$, 1,3,2',6'-tetra-N-Y-2''-O-Z-3'',4''-N,O-carbonyl-5-dehydrogentamicin $C_{1a}$, 1,3,2',6'-tetra-N-Y-2''-O-Z-3'',4''-N,O-carbonyl-5-dehydrogentamicin $C_2$, 1,3,2',6'-tetra-N-Y-2''-O-Z-3'',4''-N,O-carbonyl-5-dehydrogentamicin $C_{2a}$, 1,3,2',6'-tetra-N-Y-2''-O-Z-3'',4''-N,O-carbonyl-5-dehydrogentamicin $C_{2b}$, 1,3,2'-tri-N-Y-3',2''-di-O-Z-4', 6'-O-W-3'',4''-N,O-carbonyl-5-dehydrogentamicin $X_2$, 1,3,2',6'-3''-penta-N-Y-4',2''-di-O-Z-4'',6''-O-W-5-dehydrotobramycin, 1,3,2',6'-tetra-N-Y-2''-O-Z-3'',4''-N,O-carbonyl-5-dehydroverdamicin, 1,3,2',6'-tetra-N-Y-2''-O-Z-3'',4''-N,O-carbonyl-5-dehydrosisomicin, 1,3,6',3''-tetra-N-Y-2',2''-di-O-Z-3',4'; 4'',6''-di-O-W-5-dehydrokanamycin A, 1,3,6',3''-tetra-N-Y-4',2''-di-O-Z-2',3';4'',6''-di-O-W-5-dehydrokanamycin A, 1,3,2',6',3''-penta-N-Y-3',4';4'',6''-di-O-W-2''-O-Z-5-dehydrokanamycin B, 1,3,2',6',3''-penta-N-Y-2''-O-Z-4'', 6''-O-W-3',4'-dideoxy-5-dehydrokanamicin B, 1,3,2',6'-tetra-N-Y-2''-O-Z-3'',4''-N,O-carbonyl-5-dehydro-Antibiotic G-52, 1,3,2',6',3''-penta-N-Y-2'',4''-di-O-Z-5-dehydro-Antibiotic 66-40B, 1,3,2',6'-tetra-N-Y-2''-O-Z-3'',4''-N,O-carbonyl-5-dehydro-Antibiotic 66-40D, 1,3,2'-tri-N-Y-3',2''-di-O-Z-4'',6'-O-W-3'',4''-N,O-carbonyl-5-dehydro-Antibiotic G-418, 1,3,2',6'-tetra-N-Y-3',4'-O-W-2''-O-Z-3'',4''-N,O-carbonyl-5-dehydro-Antibiotic JI-20A, and 1,3,2',6'-tetra-N-Y-3',4'-O-W-2''-O-Z-3'',4''-N,O-carbonyl-5-dehydro-Antibiotic JI-20B, wherein W is a member selected from the group consisting of alkylidene, cycloalkylidene and arylakylidene;

Y is a member selected from the group consisting of benzyloxycarbonyl, alkoxybenyzloxycarbonyl, alkoxycarbonyl, and provided said 5-dehydro-4,6-di-O-(aminoglycosyl)-2-deoxystreptamine is devoid of N,O-carbonyl protecting groups, lower alkanoyl;

Z is hydrocarboncarbonyl, said hydrocarbon having up to 8 carbon atoms;

and the 1-N-K'' derivatives of the foregoing wherein K'' is an alkyl substituent selected from the group consisting of alkyl, alkyl cycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; any amino function being substituted by said group, Y, and any hydroxyl being converted to an ester OZ or, when said hydroxyl group is alpha or beta to an amino protecting group Y, the hydroxyl group together with said protecting group Y is converted to an oxazolidinone or a tetrahydro-1,3-oxazin-2-one, respectively, Y and Z being as hereinabove defined.

28. A compound of claim 27 wherein Y is benzyloxycarbonyl and Z is benzoyl.

29. A compound of claim 27 which is 1,3,2',6'-tetra-N-benzyloxycarbonyl-2''-O-benzoyl-3'',4''-N,O-carbonyl-5-dehydrogentamicin $C_{1a}$.

30. A method of eliciting an antibacterial response in a warm blooded animal having a susceptible bacterial infection, which comprises administering to said animal a nontoxic, antibacterially effective amount of a member selected from the group consisting of 5-epigentamicin A, 5-epigentamicin B, 5-epigentamicin $B_1$, 5-epigentamicin $C_1$, 5-epigentamicin $C_{1a}$, 5-epigentamicin $C_2$, 5-epigentamicin $C_{2a}$, 5-epigentamicin $C_{2b}$, 5-epigentamicin $X_2$, 5-epitobramycin, 5-epiverdamicin, 5-epikanamycin A, 5-epikanamycin B, 5-epi-3',4'-dideoxykanamycin B, 5-epi-Antibiotic G-52, 5-epi-Antibiotic 66-40B, 5-epi-Antibiotic 66-40D, 5-epi-Antibiotic G-418, 5-epi-Antibiotic JI-20A, 5-epi-Antibiotic JI-20B;

the 1-N-K-derivatives of the foregoing wherein K is an alkyl substituent selected from the group consisting of alkyl, alkyl cycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only one of said functions can be attached at any one carbon atom; and the pharmaceutically acceptable acid addition salts thereof.

31. A pharmaceutical composition comprising an inert carrier and, an antibacterially effective amount of a compound selected from the group consisting of 5-epigentamicin A, 5-epigentamicin B, 5-epigentamicin $B_1$, 5-epigentamicin $C_1$, 5-epigentamicin $C_{1a}$, 5-epigentamicin $C_2$, 5-epigentamicin $C_{2a}$, 5-epigentamicin $C_{2b}$, 5-epigentamicin $X_2$, 5-epitobramycin, 5-epiverdamicin, 5-epikanamycin A, 5-epikanamycin B, 5-epi-3',4'-dideoxykanamycin B, 5-epi-Antibiotic G-52, 5-epi-Antibiotic 66-40B, 5-epi-Antibiotic 66-40D, 5-epi-Antibiotic G-418, 5-epi-Antibiotic JI-20A, 5-epi-Antibiotic JI-20B;

the 1-N-K-derivatives of the foregoing, wherein K is an alkyl substituent selected from the group consisting of alkyl, alkyl cycloalkyl, alkenyl, aralkyl, hydroxyalkyl, aminoalkyl, alkylaminoalkyl, aminohydroxyalkyl, and alkylaminohydroxyalkyl, said alkyl substituent having up to 8 carbon atoms, the carbon in said alkyl substituent adjacent to the aminoglycoside nitrogen being unsubstituted, and when said alkyl substituent is substituted by both hydroxyl and amino functions, only of said functions can be attached at any one carbon atom; and the pharmaceutically acceptable acid addition salts thereof.

32. A comound of claim 19 wherein said 1-N-acyl is 1-N-(S-4-amino-2-hydroxybutyryl).

33. A compound of claim 9 wherein said 1-N-acyl is 1-N-(S-3-amino-2-hydroxypropionyl).

* * * * *

UNITED STATES PATENT OFFICE
CERTIFICATE OF CORRECTION

Patent No. 4,000,261  Dated December 28, 1976

Inventor(s) Peter J. L. Daniels  Page 1 of 2

It is certified that error appears in the above-identified patent and that said Letters Patent are hereby corrected as shown below:

Columns 3 and 4, lines 1-30 should read:

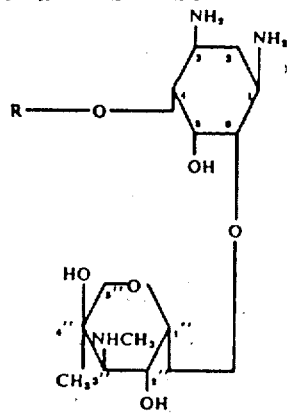

and the 1-N-K derivatives thereof, K being as hereinabove defined;
wherein R is an aminoglycosyl function selected from the group consisting of:

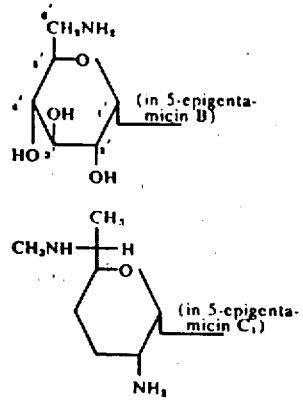

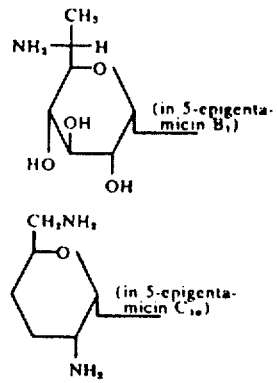

Columns 3 and 4, lines 30-60 should read:

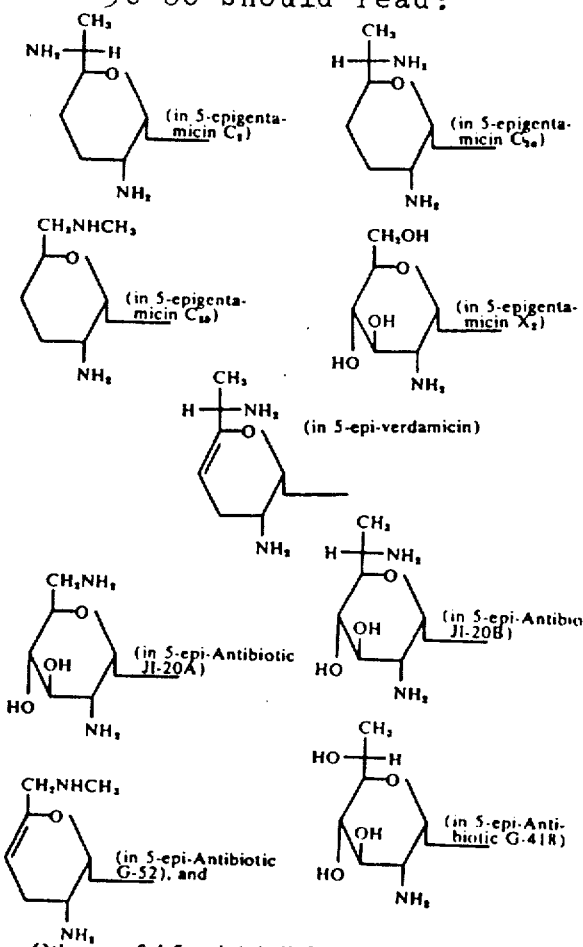

Other useful 5-epi-4,6-di-O-(aminoglycosyl)-2-deoxystreptamines of this invention include 5-epi-tobramycin, 5-epi-kanamycin A, 5-epi-kanamycin B and 5-epi-3',4'-dideoxykanamycin B of following formula II:

UNITED STATES PATENT OFFICE
CERTIFICATE OF CORRECTION

Patent No. 4,000,261  Dated December 28, 1976

Inventor(s) Peter J. L. Daniels  Page 2 of 2

It is certified that error appears in the above-identified patent and that said Letters Patent are hereby corrected as shown below:

Column 2, lines 31-34, "-5-epitobramycin, 5-epitobramycin, 5-epi-Antibiotic G-418, 5-epi-Antibiotic 66-B, 5-epi-Antibiotic 66-40D, 66-40D, 5-epi-Antibiotic 66-40JI-20A," should read ---5-epi-tobramycin, 5-epi-Antibiotic G-418, 5-epi-Antibiotic 66-40B, 5-epi-Antibiotic 66-40D, 5-epi-Antibiotic JI-20A,---; line 62, "-tamicin $C_2$5-epigentamicin $C_{2b}$, 5-epi-gentamicin $C_{2b}$," should read ---tamicin $C_2$, 5-epi-gentamicin $C_{2a}$, 5-epigentamicin $C_{2b}$,---. Column 20, line 12, ", 3'-penta-" should read ---,3"-penta---. Column 32, lines 36 and 37, "A. 1,3.2',6',3"-Penta-N-benzyloxy-carbonylgentamicin $C_{12}$" should read ---A. 1,3,2',6',3"-Penta-N-benzyloxycarbonylgentamicin $C_{1a}$---; line 58, "N)" should read ---H)---. Column 38, lines 60-65, "(3"-N-$CH_3$), (5-$\overset{O}{\underset{O}{\parallel}}$-S-$CH_3$)," should read ---(3"-N-$CH_3$), 3.04 (5-$\overset{O}{\underset{O}{\parallel}}$-S-$CH_3$),---. Column 39, line 27, "JI-2CA." should read ---JI-20A.---; line 52, "; 4'$\lambda$-" should read ---; 4"---. Column 40, line 38, "; 4'$\lambda$-" should read ---; 4"---; line 58, "; 4'$\lambda$-" should read ---; 4"---. Column 41, line 18, "-3",2"-" should read ---3',2"---; line 24, "-2",2"-" should read ---2',2"---; line 40, ", 2'$\lambda$-" should read ---, 2"---. Column 53, lines 24 and 25, after the Table, should read ---CMR ($D_2O$): PPM: $\delta$ 149.8, 102.9, 97.4, 97.0, 83.9, 80.5, 73.2, 70.1, 69.6, 68.5, 63.9, 54.5, 47.1, 47.0, 43.1, 40.8, 37.5, 33.0, 25.6, 22.4, 14.6.---. Column 61, line 28, "-1-N-(S-$\xi$-amino-" should read ---1-N-(S-$\gamma$-amino---; line 46, "-5-epigentamicin," should read ---5-epitobramycin,---. Column 66, line 47, "Per 2.0 ml. vial✗" should read ---Per 2.0 ml. vial---.

Signed and Sealed this

Nineteenth Day of April 1977

[SEAL]

Attest:

RUTH C. MASON
Attesting Officer

C. MARSHALL DANN
Commissioner of Patents and Trademarks

UNITED STATES PATENT OFFICE
CERTIFICATE OF CORRECTION

Patent No. 4,000,261                    Dated December 28, 1976

Inventor(s) Peter J. L. Daniels

It is certified that error appears in the above-identified patent and that said Letters Patent are hereby corrected as shown below:

Column 72, line 33, Claim 33, "A compound of claim 9" should read ---A compound of claim 19---.

Signed and Sealed this

Twenty-eighth Day of November 1978

[SEAL]

Attest:

RUTH C. MASON
Attesting Officer

DONALD W. BANNER
Commissioner of Patents and Trademarks